(12) United States Patent
Stolowitz et al.

(10) Patent No.: US 7,208,322 B2
(45) Date of Patent: Apr. 24, 2007

(54) SENSOR SURFACES FOR DETECTING ANALYTES

(75) Inventors: Mark L. Stolowitz, Woodinville, WA (US); Jean P. Wiley, Woodinville, WA (US); Guisheng Li, Bothell, WA (US); Kevin Lund, Lynnwood, WA (US)

(73) Assignee: Agilent Technologies, Inc., Santa Clara, CA (US)

( * ) Notice: Subject to any disclaimer, the term of this patent is extended or adjusted under 35 U.S.C. 154(b) by 666 days.

(21) Appl. No.: 10/116,013

(22) Filed: Apr. 2, 2002

(65) Prior Publication Data

US 2002/0192722 A1    Dec. 19, 2002

Related U.S. Application Data

(60) Provisional application No. 60/281,094, filed on Apr. 2, 2001, provisional application No. 60/281,093, filed on Apr. 2, 2001, provisional application No. 60/281,085, filed on Apr. 2, 2001, provisional application No. 60/360,798, filed on Mar. 1, 2002.

(51) Int. Cl.
*G01N 33/553*    (2006.01)
*G01N 27/00*    (2006.01)
*G01N 33/567*    (2006.01)
*G01N 33/566*    (2006.01)

(52) U.S. Cl. ............................ 436/525; 435/6; 435/7.2; 435/7.5; 436/86; 436/94; 436/501; 436/528; 436/149; 436/151; 436/806; 436/829

(58) Field of Classification Search .................... 435/6, 435/7.5, 7.2; 436/149, 151, 806, 525, 86, 436/528, 829, 501, 94

See application file for complete search history.

(56) References Cited

U.S. PATENT DOCUMENTS

| | | |
|---|---|---|
| 4,889,427 A | 12/1989 | Van Veen et al. |
| 5,164,589 A | 11/1992 | Sjodin |
| 5,242,828 A | 9/1993 | Bergstrom et al. |
| 5,436,161 A | 7/1995 | Bergstrom et al. |
| 5,492,840 A | 2/1996 | Malmqvist et al. |
| 5,554,541 A | 9/1996 | Malmqvist et al. |
| 5,561,069 A | 10/1996 | Brigham-Burke et al. |
| 5,641,640 A | 6/1997 | Hanning |
| 5,663,790 A | 9/1997 | Ekstrom et al. |
| 5,716,854 A | 2/1998 | Lofas et al. |
| 5,898,503 A | 4/1999 | Keller et al. |
| 5,912,456 A | 6/1999 | Melendez et al. |
| 5,946,083 A | 8/1999 | Melendez et al. |
| 5,955,729 A | 9/1999 | Nelson et al. |
| 5,965,456 A | 10/1999 | Malmqvist et al. |
| 5,972,612 A | 10/1999 | Malmqvist et al. |
| 6,002,954 A | 12/1999 | Van Antwerp et al. |
| 6,008,893 A | 12/1999 | Roos et al. |
| 6,011,984 A | 1/2000 | Van Antwerp et al. |
| 6,111,248 A | 8/2000 | Melendez et al. |
| 6,111,652 A | 8/2000 | Melendez et al. |
| 6,127,183 A | 10/2000 | Ivarsson et al. |
| 6,143,513 A | 11/2000 | Lofas |
| 6,143,574 A | 11/2000 | Karlsson et al. |
| 6,183,696 B1 | 2/2001 | Elkind et al. |
| 6,191,847 B1 | 2/2001 | Melendez et al. |
| 6,200,814 B1 | 3/2001 | Malmqvist et al. |
| 6,207,381 B1 | 3/2001 | Larsson et al. |
| 6,289,286 B1 | 9/2001 | Andersson et al. |
| 2001/0026943 A1 | 10/2001 | Dickopf et al. |
| 2002/0074513 A1 | 6/2002 | Abel et al. |
| 2004/0046128 A1 | 3/2004 | Abel et al. |

FOREIGN PATENT DOCUMENTS

| | | |
|---|---|---|
| EP | 0863395 A2 | 9/1998 |
| EP | 0973023 A1 | 1/2000 |
| EP | 1186881 A1 | 3/2002 |
| WO | WO 98/22808 A1 | 5/1998 |
| WO | WO 00/43534 A1 | 7/2000 |
| WO | WO 00/75644 A1 | 12/2000 |
| WO | WO 01/63256 A1 | 8/2001 |

OTHER PUBLICATIONS

Baird, C. and Myszka, D., "Current and emerging commercial optical biosensors" J. Mol. Recognition 14:261-268 (2001).
Carey, R. et al., "Self-assembled monolayers containing ω-mercaptoalylboronic acids adsorbed onto gold form a highly cross-linked, thermally stable borate glass surface" Langmuir 10:2228-2234 (1994).
Kanayama, N. et al., "Interfacial recognition of sugars by boronic acid-carrying self-assembled monoloayer" Langmuir 16:577-583 (2000).
Lee, M. et al., "Formation of a self-assembled phenylboronic acid monolayer and its application toward developing a surface plasmon resonance-based monosaccharide sensor" Analytical Biochemistry 310:163-170 (2002).
Löfäs, S. et al., "A novel hydrogel matrix on gold surfaces in surface plasmon resonance sensors for fast and efficient covalent immobilization of ligands" J. Chem. Soc., Chem. Commun., pp. 1526-1528 (1990).
Rich, R. and Myszka, D., "Survey of the year 2000 commercial optical biosensor literature" J. Mol. Recognition 14:273-294 (2001).
Shumaker-Parry, J. et al., "Probing Protein: DNA interactions using a uniform monolayer of DNA and surface plasmon resonance" Proceedings of the SPIE 3922:158-166 (2000).
Spinke, J. et al., "Molecular recognition at self-assembled monolayers: Optimization of surface functionalization" J. Chem. Phys. 99:7012-7019 (1993).

(Continued)

Primary Examiner—Mary E. Ceperley

(57) ABSTRACT

The present invention provides a sensor surface comprising: a substrate coated with a free electron metal; and a matrix layer disposed on the free electron metal, wherein the matrix layer comprises an organic compound having a boronic acid complexing moiety. The matrix is preferably a self-assembled monolayer (SAM), a mixed self-assembled monolayer (mSAM), or combinations thereof.

37 Claims, 11 Drawing Sheets

OTHER PUBLICATIONS

Taiji, O., Applicant: Toto Ltd., "Surface Plasmon Resonance Sensor Apparatus" English Language Abstract of Japanese Patent Application No. JP 09 257806 A, published Oct. 3, 1997.

Valina-Saba, M. et al., "A self assembled shell of 11-mercaptoundecanoic aminophenylboronic acids on gold nanoclusters" Materials Science and Engineering C 8-9:205-209 (1999).

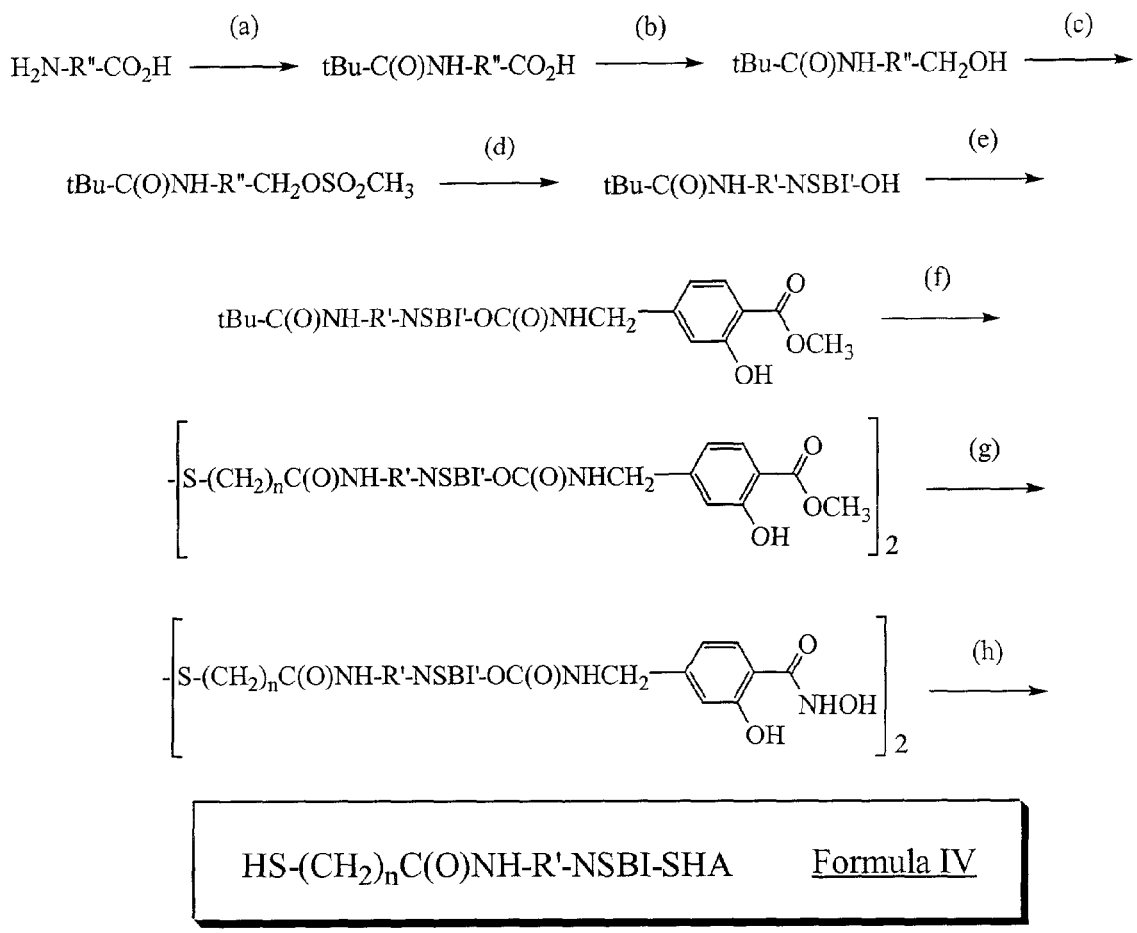

(a) Di-*tert*-butyldicarbonate, water/methanol, aqueous sodium hydroxide; then hydrochloric acid (b) Borane, tetrahydrofuran (c) Methanesulfonyl chloride, dichloromethane, triethylamine (d) Hexa(ethylene glycol), sodium hydroxide, 110°C (e) N,N'-Carbonyldiimidazole, N,N-dimethylformamide; then 4-aminomethyl-2-hydroxybenzoic acid methyl ester, triethylamine, 60-65°C (f) Hydrogen chloride, 1,4-dioxane; then dithiopropionic acid, N-hydroxysuccinimide, N,N'-dicyclohexylcarbodiimide, N,N-diisopropylethylamine (g) Sodium methoxide, hydroxylamine hydrochloride, methanol (h) Tris-carboxyethylphosphine hydrochloride, water (pH 5)

*FIG. 3*

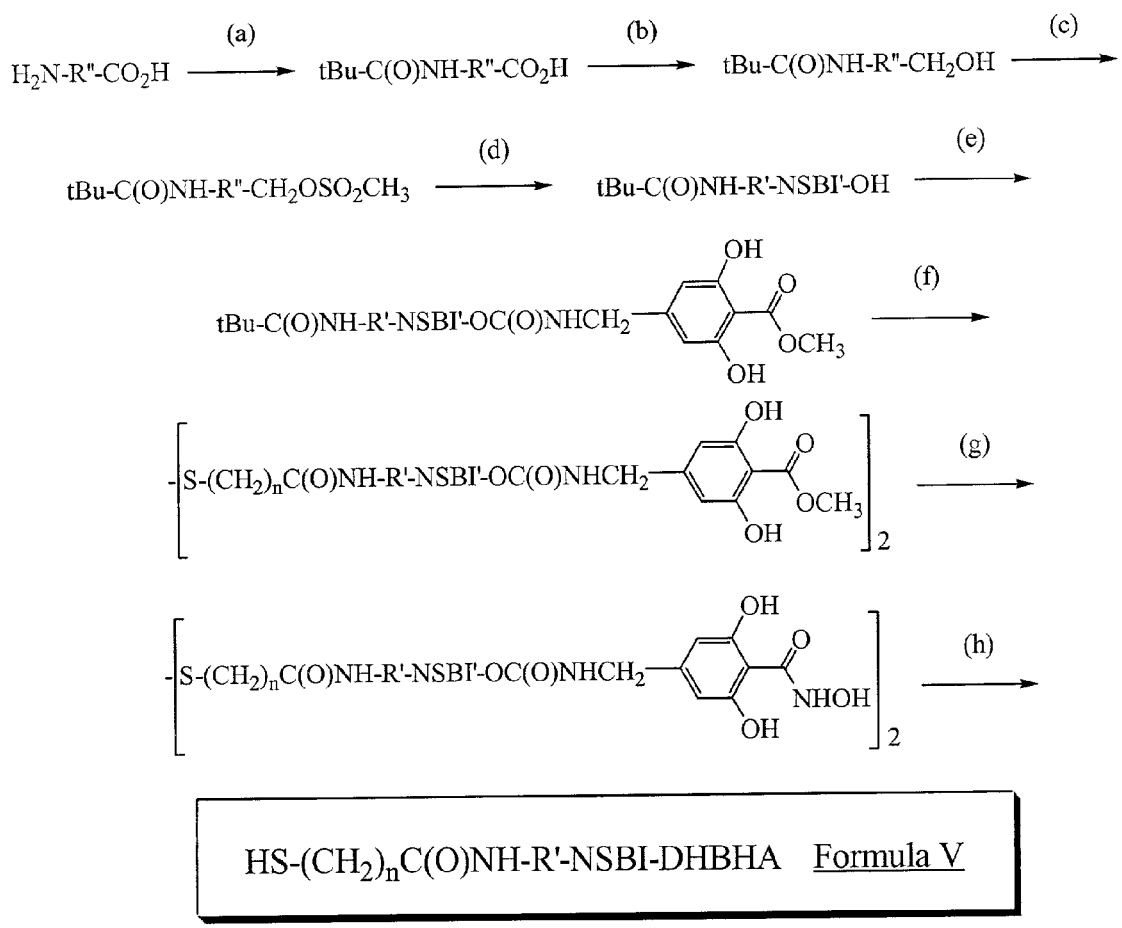

(a) Di-*tert*-butyldicarbonate, water/methanol, aqueous sodium hydroxide; then hydrochloric acid (b) Borane, tetrahydrofuran (c) Methanesulfonyl chloride, dichloromethane, triethylamine (d) Hexa(ethylene glycol), sodium hydroxide, 110°C (e) N,N'-Carbonyldiimidazole, N,N-dimethylformamide; then 4-aminomethyl-2,6-dihydroxybenzoic acid methyl ester, triethylamine, 60-65°C (f) Hydrogen chloride, 1,4-dioxane; then dithiopropionic acid, N-hydroxysuccinimide, N,N'-dicyclohexylcarbodiimide, N,N-diisopropylethylamine (g) Sodium methoxide, hydroxylamine hydrochloride, methanol (h) Tris-carboxyethylphosphine hydrochloride, water (pH 5)

FIG. 4

SENSOR SURFACES FOR DETECTING ANALYTES

CROSS-REFERENCES TO RELATED APPLICATIONS

This application claims the benefit of U.S. Provisional Patent Application Ser. Nos. 60/281,085, 60/281,093, and 60/281,094, all filed on Apr. 2, 2001. This application further claims the benefit of U.S. Provisional Application No. 60/360,798, filed Mar. 1, 2002. Each of the foregoing applications are hereby incorporated by reference in their entirety for all purposes. This application further incorporates by reference, U.S. Application No. 10/115,721, filed on Apr. 2, 2002.

FIELD OF THE INVENTION

The present invention relates, inter alia, to surface chemistries for immobilizing biomolecules on sensor surfaces. More particularly, it relates to novel boronic compound complexing agents useful for the preparation of a self-assembled molecular monolayer on a metal surface, and the method of making and using such reagents.

BACKGROUND OF THE INVENTION

There are two approaches to solving biological questions at the molecular level: structural analysis and functional analysis. Both approaches make use of independent technologies that have been optimized to provide particular types of information. Traditionally, the principal techniques employed for structural analysis are microscopy (optical, electron, and force), optical spectroscopy (infrared, visible and ultraviolet), nuclear magnetic resonance spectrometry, mass spectrometry, x-ray crystallography, sequencing, and molecular modeling. These techniques provide information about the size of the molecule in question, the kinds of functional groups that are present in the molecule, and the relative orientation of those functional groups in one, two and three dimensions.

Although researchers have been able to collect a wealth of structural information about a wide diversity of molecules using the techniques mentioned above, the relationship between structure and function is still largely obscure. Most biologically interesting molecules fulfill their natural function through interaction(s) with other molecules. Thus, analytical techniques used for the study of the interactions between and among biologically interesting molecules will significantly advance the understanding of their function(s), as well as begin to more completely connect structural information with functionality. The interactions of interest can be described in terms of rate constants (association, dissociation, mass transport, diffusion and the like), equilibrium constants (measures of the affinities of the various molecules for each other) and the stoichiometry of the interaction. The ability to accurately measure and compare these fundamental parameters is critical to the characterization and understanding of molecular interactions.

Bioconjugation is a descriptive term for the joining of two or more different molecular species by chemical or biological means, in which at least one of the molecular species is preferably a biological macromolecule. These biological macromolecules include, but are not limited to, conjugation of proteins, peptides, polysaccharides, hormones, nucleic acids, lipid bilayers, liposomes and cells, with each other or with any other molecular species that add useful properties, including, but not limited to, drugs, radionuclides, toxins, haptens, inhibitors, chromophores, fluorophores, ligands, and the like. Immobilization of biological macromolecules is also considered a special case of bioconjugation in which the macromolecule is conjugated, either reversibly or irreversibly, to an insoluble support, such as a chromatographic matrix, microwell plate, porous membrane, polymer bead, glass microscope slide, silicon chip, and the like. Bioconjugation is utilized extensively in biochemical, immunochemical and molecular biological research. Major applications of bioconjugation include, but are not limited to, detection of gene probes, enzyme-linked immunological solid-phase assays, affinity purification, monoclonal antibody-drug targeting and medical imaging.

Bioconjugates are generally classed either as direct or indirect conjugates. Direct conjugates encompass those in which two or more components are joined by direct covalent chemical linkages. Alternatively, indirect conjugates encompass those in which two or more components are joined via an intermediary complex involving a biological macromolecule.

Although numerous methods of indirect bioconjugate preparation have been described, a significant number of those reported in the literature have been prepared by exploiting the biotin-avidin interaction. In this system, the binding specificity of the protein avidin (purified from egg white) or streptavidin (purified from the bacterium *Streptomyces avidinii*) toward the cofactor biotin (vitamin H) is utilized to connect a (strept)avidin-conjugated macromolecule with a biotin-conjugated macromolecule. Both avidin and streptavidin possess four biotin binding sites of very high affinity ($K_d=10^{-15}$ mol$^{-1}$).

The avidin-biotin system has been utilized extensively for enzyme-linked immunological solid-phase assays (ELISA), in which an enzyme-avidin conjugate (useful for sensitive detection by reaction with a substrate of the enzyme to produce a colored or luminescent product) is employed to detect the presence of biotin-conjugated antibody, after first binding that antibody conjugate to an immobilized hapten or antigen. Applications of the avidin-biotin system number in the hundreds, and have recently been reviewed (see, Wilchek, M. and Bayer, E. A. (1990) *Methods in Enzymology*, volume 184).

While utilized extensively, several limitations are known to be associated with avidin-biotin system. These include nonspecific binding of assay components due predominantly to the basicity of the avidin molecule or to the presence of carbohydrate chains on the avidin molecule, and background interference associated with the presence of endogenous biotin, which is ubiquitous in both eukaryotic and prokaryotic cells.

An alternative indirect bioconjugation system designed to circumvent the limitations of the avidin-biotin system has been recently developed for the detection of gene probes using and enzyme-linked approach (see, Kessler, C., Hôltke, H.-J., Seibl, R., Burg, J. and Mühlegger, K. (1990) *Biol. Chem. Hoppe-Seyler* 371, 917–965). This system involves the use of the steroid hapten digoxigenin, an alkaloid occurring exclusively in digitalis plants, and the Fab fragments derived from polyclonal sheep antibodies directed against digoxigenin (α-digoxigenin). The high specificity of the various a-digoxigenin antibodies for digoxigenin affords low backgrounds and eliminates the nonspecific binding often observed in the avidin-biotin system. Digoxigenin-conjugated DNA and RNA probes can detect single-copy sequences in human genomic Southern blots. The development of the digoxigenin-α-digoxigenin system has been reviewed (see, Kessler, C. (1990) in *Advances in Mutagenesis Research* (Obe, G., ed.) pp. 105–152, Springer-Verlag, Berlin and Heidelberg). The digoxigenin-α-digoxigenin system is the most recent representative of several hapten-antibody-based indirect conjugation systems now routinely used for bioconjugation.

Phenylboronic acids are known to interact with a wide range of polar organic molecules having certain requisite functionalities. Complexes of varying stabilities involving 1,2-diols, 1,3-diols, 1,2-hydroxy acids, 1,3-hydroxy acids, 1,2-hydroxylamines, 1,3-hydroxylamines, 1,2-diketones and 1,3-diketones are known to form with either neutral phenylboronic acid or phenylboronate anion. Consequently, immobilized phenylboronic acids have been exploited as chromatographic supports to selectively retain, from complex biological samples, those molecular species having the requisite functionalities. Many important biological molecules including carbohydrates, catecholamines, prostaglandins, ribonucleosides and steroids contain such functionalities, and have been either analyzed or purified in this manner. The use of phenylboronic acid chromatographic media for the separation and isolation of biological molecules has been discussed in several reviews (see, Singbal, R. P. and DeSilva, S. S. M. (1989) *Adv. Chromatog.* 31, 293–355; Mazzeo, J. R. and Krull, I. S. (1989) *BioChromatog.* 4, 124–130; and Bergold, A. and Scouten, W. H. (1983) in *Solid Phase Biochemistry* (Scouten, W. H., ed.) pp. 149–187, John Wiley and Sons, New York).

Phenylboronic acid, like boric acid, is a Lewis acid, and ionizes not by direct protonation, but rather by hydration to give the phenylboronate anion ($pK_a$=8.86). Phenylboronic acid is three times as strong an acid as boric acid. Ionization of phenylboronic acid is an important factor in complex formation, in that, upon ionization, the boron nucleus changes from trigonal coordination (having average bond angles of 120° and average bond lengths of 1.37 angstroms) to tetrahedral coordination (having average bond angles of 109° and average bond lengths of 1.48 angstroms).

Molecular species having cis or coaxial 1,2- or 1,3-diol functionalities (notably carbohydrates) are known to complex with immobilized phenylboronate anions, forming cyclic esters, under alkaline aqueous conditions (see, Lorand, J. P. and Edwards, J. O. (1959) *J. Org. Chem.* 24, 769). Acidification of 1,2- and 1,3-diol complexes with phenylboronic acid to neutral pH is known to release the diol-containing species, presumably due to hydrolysis of the cyclic ester. Coplanar aromatic 1,3-diols, such as 1,8-dihydroxynaphthalene, are known to form stable complexes even under acidic conditions, due to the hydrolytic stability of six-membered cyclic boronic acid esters (see, Sienkiewicz, P. A. and Roberts, D. C. (1980), *J. Inorg. Nucl. Chem.* 42, 1559–1571).

Molecular species having pendant 1,2-hydroxylamine, 1,3-hydroxylamine, 1,2-hydroxyamide, 1,3-hydroxyamide, 1,2-hydroxyoxime and 1,3-hydroxyoxime functionalities are also known to reversibly complex with phenylboronic acid under alkaline aqueous conditions similar to those associated with the retention of diol-containing species (see, Tanner, D. W. and Bruice, T. C. (1967) *J. Amer. Chem. Soc.* 89, 6954).

2-Acetamidophenylboronic acids have been proposed as potential linkers for selective bioconjugation via the vicinal diol moieties of the carbohydrate residues associated with glycoproteins (see, Cai, S. X. and Keana, J. F. W. (1991) *Bioconjugate Chem.* 2, 317–322). Phenylboronic acid bioconjugates derived from 3-isothiocyanatophenylboronic acid have been successfully utilized for appending radioactive technetium dioxime complexes to monoclonal antibodies for use in medical imaging (see, Linder, K. E., Wen, M. D., Nowotnik, D. P., Malley, M. F., Gougoutas, J. Z., Nunn, A. D., and Eckelman, W. C. (1991) *Bioconjugate Chem.* 2, 160–170; Linder, K. E., Wen, M. D., Nowotnik, D. P., Ramalingam, K., Sharkey, R. M., Yost, F., Narra, R. K. and Eckelman, W. C. (1991) *Bioconjugate Chem.* 2, 407–414).

3-Aminophenylboronic acid has been covalently appended to proteins by a variety of chemical methods and the resulting phenylboronic acid bioconjugates tested for their binding of D-sorbitol, D-mannose and glycated hemoglobin (GHb). The interactions proved to be reversible and of very low affinity, rendering the bioconjugates of very limited practical use. Similarly, an alkaline phosphatase-phenylboronate used in an attempted enzyme-linked assay for the detection of GHb failed to detect the presence of glycated protein (see, Frantzen, F., Grimsrud, K., Heggli, D. and Sundrehagen, E. (1995) *Journal of Chromatography B* 670, 37–45).

A novel class of phenylboronic acid reagents and boronic acid compound complexing reagents have been developed for conjugating biologically active species (BAS) (also known as "bioactive species") and exploiting indirect bioconjugation through reversible formation of a boronic acid complex. These reagents and associated conjugates can be used in a manner analogous to the avidin-biotin and digoxigenin-α-digoxigenin systems. However, unlike either of these two biological systems wherein the functional viability of the biological macromolecule (protein) must be maintained to preserve the requisite binding properties, the bioconjugate formed through the boron complex is generally insensitive to significant variations in ionic strength, temperature, the presence of organic co-solvents, and the presence of chaotropic agents (protein and nucleic acid denaturants). Additionally, the complex between the boronic acid and the boronic compound complexing reagent is facilely reversible, using a combination of low or high pH, elevated temperature, and/or competitive releasing reagents. These phenylboronic acid reagents and boronic compound complexing reagents, their bioconjugates and complexes as well as methods for their preparation and use are the subject of U.S. Pat. Nos. 5,594,111, 5,623,055, 5,668,258, 5,648,470, 5,594,151, 5,623,055, 5,668,257, 5,668,258, 5,688,928, 5,677,431, 5,744,727, 5,777,148, 5,837,878, 5,847,192, 5,852,178, 5,859,210, 5,869,623, 5,872,224, 5,876,938, 5,877,297, 6,008,406, 6,075,126, 6,124,471 and 6,156,884, the teachings of each of which are incorporated herein by reference.

Phosphoramidite reagents containing protected phenylboronic acid and 1,3-phenyldiboronic acid moieties for the preparation of modified synthetic oligonucleotides are the subject of U.S. Pat. No. 6,031,117. Oligonucleotides and polynucleotides containing phenylboronic acid and 1,3-phenyldiboronic acid, prepared from the aforementioned phosphoramidite reagents, are the subject of U.S. Pat. No. 6,013,783. 2'-Deoxyuridine triphosphate and uridine triphosphate containing phenylboronic acid and 1,3-phenyldiboronic acid moieties for the preparation of modified polydeoxyribonucleotides (DNA) and polyribonucleotides (RNA) are the subject of U.S. Pat. No. 5,831,046. Polydeoxyribonucleotides (DNA) and polyribonucleotides (RNA) containing phenylboronic acid and 1,3-phenyldiboronic acid, prepared from the aforementioned 2'-deoxyuridine triphosphate and uridine triphosphate reagents, are the subject of U.S. Pat. No. 5,831,045. The teachings of each these patents are incorporated herein by reference.

In recent years, an increasing number of techniques have become available for functional studies at the molecular level, enabling examination of the way(s) molecules interact to carry out their specific biological purpose(s). One of the techniques that has made a major contribution in this regard is real-time biomolecular interaction analysis, also termed BIA. BIA measures interactions between two or more molecules without the use of labels. Molecules that have been studied using this technique include proteins, peptides, nucleic acids, oligonucleotides, carbohydrates, lipids, small molecule metabolites and pharmaceuticals. Additionally, BIA has been used to study the binding of biomolecules to cell surfaces. A recent review of BIA technologies and commercial instrumentation has been published (see, Baird, C. L. and Myszka, D. G. (2001) *J. Mol. Recognit.* 14, 261–268), as has a recent review of BIA applications (Rich, R. L. and Myszka, D. G. (2001) *J. Mol. Recognit.* 14, 273–294).

One commonly used technology for performing BIA relies on the surface optical phenomenon called surface plasmon resonance (SPR), which detects minute changes in the refractive index of a medium in contact with a sensor surface. Surface plasmon resonance is the oscillation of free electrons at the surface of a thin metal film. These oscillations are affected by changes in the refractive index of the medium very near to the surface of the film. The general method for use of SPR in BIA is to immobilize one member of a biological binding pair (the ligand) on the surface of the metal film, and then to introduce the other member of the binding pair (the analyte) in solution. As the interaction progresses, mass accumulates on the sensor surface due to binding of the analyte to the ligand. This accumulation of mass is accompanied by a proportional change in refractive index at the metal surface, which is monitored by SPR in real time. The rate at which mass is gained or lost from the surface provides important functional information about the interaction. Various types of instrumentation for the implementation of SPR as a biosensor detection technique have been described (for examples, see, Liedberg, B. et al. (1983) *Sensors and Actuators* 4, 299–304; U.S. Pat. No. 6,127,183; U.S. Pat. No. 5,965,456; U.S. Pat. No. 5,374,563; U.S. Pat. No. 5,770,462; U.S. Pat. No. 5,064,619; U.S. Pat. No. 5,815,278; and U.S. Pat. No. 5,912,456).

An essential part of BIA using SPR detection is the means by which the ligand is tethered to the metal film surface. Common metals for SPR detection include gold, silver and copper, as well as others; the most common metal is gold, which is usually deposited in a thin layer on a material having a high index of refraction, such as glass. A common and extremely useful technique for the chemical modification of gold surfaces for the immobilization of biomolecules is the use of ω-functionalized alkanethiols to form self-assembled monolayers presenting reactive sites for the attachment of biological ligands. Several methods have been described. In one (see, Lofas, S. et al. (1990) *J. Chem. Soc., Chem. Commun.*, 1526–1528), long-chain hydroxyalkanethiols are used to form a monolayer of exposed hydroxyl groups on a gold biosensor surface; carboxymethyldextran polymers are then covalently attached to the hydroxyl groups to provide a matrix in which ligands may be chemically immobilized. In another (see, Shumaker-Parry, J. S. et al. (2000) *Proceedings of the SPIE* 3922, 158–166; Spinke et al. (1993) *J. Chem. Phys.* 99, 7012–7019), a binary mixed monolayer composed of hydroxyl-terminated and biotin-terminated alkanethiols is deposited on a gold biosensor surface; streptavidin is next bound to the exposed biotin moieties to provide an intermediary proteinaceous layer; and finally, biotinylated ligands are contacted with the streptavidin-modified surface and immobilized. In yet another method (U.S. Pat. No. 6,197,515), a self-assembled monolayer of alkanethiols terminally modified to provide a metal chelating functionality for the coordination of a metal ion is prepared on the gold biosensor surface; ligands having an accessible, partially coordinated metal ion are then immobilized following contact with the chelating monolayer surface.

The above methods for chemically modifying a gold surface and subsequently using the surface for the immobilization of a ligand suffer from several inadequacies when applied to BIA using SPR detection. Use of covalent immobilization of the ligand within a dextran matrix can frequently compromise the biological viability of the ligand, rendering it unsuitable for highly accurate interaction analysis. Additionally, this method distributes the ligand at varying distances from the metal surface throughout the thickness of the matrix layer; since SPR detection sensitivity decreases rapidly as the distance from the surface increases, this approach seriously reduces the observed detection sensitivity of the analysis, requiring more ligand to be immobilized to observe adequate SPR responses. This method also requires that the analyte penetrate the dextran matrix in order to find its immobilized biological binding partner; the kinetics of this process can often severely complicate the overall interaction analysis. Finally, the use of covalent chemistry renders the immobilization process irreversible. The use of the biotin-streptavidin system for immobilization as described in the previous paragraph suffers from the problems of functional irreversibility due to the very high dissociation constant of the biotin-streptavidin complex, the complicating effects of endogenous biotin in biological samples, and the need to covalently label the ligand with biotin and subsequently purify the biotinylated ligand prior to immobilization. The metal chelate technique requires that an appropriate metal chelating functionality be introduced into the ligand; for genetically engineered proteins, this can be accomplished using known recombinant DNA techniques to insert a stretch of multiple histidine amino acids at a desired location in the polypeptide chain, but for non-protein ligands, incorporation of a metal coordinating functionality into the ligand is considerably challenging.

In view of the foregoing, it would be advantageous to develop an immobilization chemistry for SPR-based BIA that exploits the benefits and advantages associated with the aforementioned class of phenylboronic acid reagents and boronic compound complexing reagents, which have been developed for conjugating biologically active species and for exploiting indirect bioconjugation through reversible formation of a boronic acid complex. The present invention fulfills this and other needs.

SUMMARY OF THE INVENTION

Biomolecular interaction analysis (BIA) is the measurement of the interaction or binding of one or more analytes to a biologically active species or ligand. One method for measuring such biomolecular interactions is to immobilize the biologically active species on the surface of a sensor, and monitor changes at the surface due to interaction with the analyte using some suitable detection methodology. Advantageously, the present invention provides an immobilization chemistry for use in BIA that exploits the benefits associated with phenylboronic acid reagents and boronic acid compound complexing reagents, which have been developed for conjugating biologically active species and for exploiting indirect bioconjugation through reversible formation of a boronic acid complex.

As such, in one embodiment, the present invention provides a sensor surface, the sensor surface comprising: a substrate coated with a free electron metal; and a matrix layer disposed on the free electron metal, wherein the matrix layer comprises an organic compound having a boronic acid complexing moiety. The matrix can be for example, a self-assembled monolayer (SAM) or, a mixed self-assembled monolayer (mSAM). In one aspect, the organic compound having the boronic acid complexing moiety is of the formula:

$$X-R-Y \quad (I)$$

In Formula I, X is an anchor group that forms a complex with a free electron metal. R, in Formula I, is an optionally substituted alkylene group optionally interrupted by one or more members selected from the group of a heteroatom, an amido group, and combinations thereof Y, in Formula I, is a boronic acid complexing moiety.

In another aspect, the organic compound having the boronic acid complexing moiety is of the formula:

$$X-(CH_2)_nC(O)NHR'-(NSBI)_m-Y \quad (IIa)$$

or $$X-(CH_2)_nNHC(O)R'-(NSBI)_m-Y \quad (IIb)$$

In Formulae IIa and IIb, X is an anchor group that forms a complex with a free electron metal. The index "n", in Formulae IIa and IIb, is an integer from 1 to about 5. R', in Formulae IIa and IIb, is an optionally substituted alkylene group optionally interrupted by a heteroatom. NSBI, in Formulae IIa and IIb, is a nonspecific binding inhibitor including, but not limited to, an oligo(ethylene glycol) [OEG], a poly(ethylene glycol) [PEG], a branched OEG, a branched PEG, an oligo(peptide), an oligo(propylene sulfoxide), a sugar, a sugar alcohol, and a dendrimer. The index "m", in Formulae IIa and IIb, is 0 or 1. Y, in Formulae IIa and IIb, is a boronic acid complexing moiety.

In a preferred embodiment, the boronic acid complexing moiety has the formula:

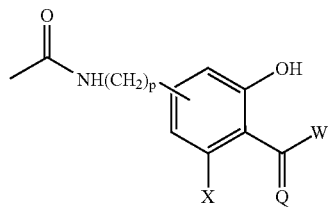

(III)

W, in Formula III, is a functional group including, but not limited to, H, OH, $NH_2$, $NHCH_3$, NHOH and $NHOCH_3$. Q, in Formula III, is a functional group including, but not limited to, O, S and NH. X, in Formula III, is either H or OH. The index "p", in Formula III, is an integer from 0 to 3. In a preferred embodiment, Q is O (oxygen), X is H (hydrogen) and W is NHOH.

In another aspect of the invention, the organic compound having the boronic acid complexing moiety is of the formula:

$$HS(CH_2)_nC(O)NHR'-NSBI-SHA \quad (IV)$$

In Formula IV, the index "n" is an integer from 1 to about 5. R', in Formula IV, is an optionally substituted alkylene group optionally interrupted by a heteroatom. NSBI, in Formula IV, is a nonspecific binding inhibitor including, but not limited to, an oligo(ethylene glycol), a poly(ethylene glycol), a branched OEG, a branched PEG, an oligo(propylene sulfoxide), a sugar, a sugar alcohol, and a dendrimer. SHA, in Formula IV, is salicylhydroxamic acid, which is a boronic acid complexing moiety.

In another aspect of the invention, the organic compound having the boronic acid complexing moiety is of the formula:

$$HS(CH_2)_nC(O)NHR'-NSBI-DHBHA \quad (V)$$

In Formula V, the index "n" is an integer from 1 to about 5. R', in Formula V, is an optionally substituted alkylene group optionally interrupted by a heteroatom. NSBI, in Formula V, is a nonspecific binding inhibitor including, but not limited to, an oligo(ethylene glycol), a poly(ethylene glycol), a branched OEG, a branched PEG, an oligo(propylene sulfoxide), a sugar, a sugar alcohol, and a dendrimer. DHBHA, in Formula V, is dihydroxybenzohydroxamic acid, which is a boronic acid complexing moiety.

In certain aspects, the matrix comprises a mixture of organic compounds, one of Formulae I, IIa, or IIb and an organic compound having the formula:

$$X-(CH_2)_nC(O)NHR'-(NSBI)_m-Z \quad (VIa)$$

or $$X-(CH_2)_nNHC(O)R'-(NSBI)_m-Z \quad (VIb)$$

In Formulae VIa and VIb, X is an anchor group that forms a complex with a free electron metal. The index "n", in Formulae VIa and VIb, is an integer from 1 to about 5. R', in Formulae VIa and VIb, is an optionally substituted alkylene group optionally interrupted by a heteroatom. NSBI, in Formulae VIa and VIb, is a nonspecific binding inhibitor including, but not limited to, an oligo(ethylene glycol), a poly(ethylene glycol), a branched OEG, a branched PEG, an oligo(propylene sulfoxide), a sugar, a sugar alcohol, and a dendrimer. The index "m", in Formulae VIa and VIb, is 0 or 1. Z, in Formulae VIa and VIb, is an unreactive, uncharged chain-terminating group including, but not limited to, H, $CH_3$, OH, $OCH_3$, $CO_2CH_3$, $C(O)NH_2$, $C(O)NHCH_3$, $C(O)N(CH_3)_2$ or $SO_2NH_2$.

In certain embodiments, the sensor surface further comprises: a substrate coated with a free electron metal; a matrix layer disposed on the free electron metal, wherein the matrix layer comprises an organic compound having a boronic acid complexing moiety; and a boronic acid moiety complexed to the boronic acid complexing moiety. Preferably, the boronic acid moiety comprises a boronic acid reagent conjugated to a biologically active species.

In certain aspects, the boronic acid moiety has the formula:

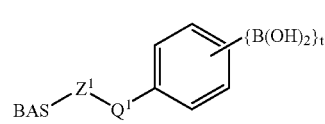

(VII)

In Formula VII, BAS is a bioactive species including, but not limited to, a protein, a polypeptide, a polypeptide fragment, a nucleic acid, a carbohydrate, a receptor, a hormone, a toxin, a vesicle, a liposome, and a cell. $Z^1$, in Formula VII, is a spacer group including, but not limited to, a saturated or unsaturated aliphatic chain of 0 to about 6 carbon equivalents in length, an unbranched saturated or unsaturated aliphatic chain of from about 6 to about 18 carbon equivalents in length with at least one intermediate amide or disulfide moiety, and an oligo(ethylene glycol) chain of from about 3 to about 12 carbon equivalents in length. When $Z^1$ is 0 it is absent. $Q^1$, in Formula VII, is a linkage including, but not limited to, an amide, methyl amide, methylene, ether, thioether, methylene ether and methylene thioether moiety. The index "t", in Formula VII, is an integer from 1 to 3.

In another embodiment, the present invention provides a process for immobilizing a biologicaly active species or ligand on the sensor surface, the method comprising: admixing a boronic acid reagent having a reactive group with a ligand to form a boronic acid-ligand conjugate; and contacting the boronic acid-ligand conjugate with the sensor surface; and incubating the boronic acid-ligand conjugate and the sensor surface, thereby immobilizing the ligand on the sensor surface.

In still yet another embodiment, the present invention provides a method for detecting an analyte, the method comprising: providing a sensor comprising a substrate coated with a free electron metal, a matrix layer disposed on the free electron metal, the matrix layer comprising an organic compound, wherein the organic compound has a boronic acid complexing moiety and, a boronic acid moiety complexed to the boronic acid complexing moiety; and contacting the sensor with the analyte to elicit a response; and measuring the response, thereby detecting the analyte.

Numerous benefits and advantages are achieved by way of the present invention over conventional sensor surfaces and methods of preparation. In certain aspects, using the sensor surfaces and methods of the present invention, there is no need to purify the boronic acid-ligand conjugate from the conjugation reaction mixture prior to contacting the boronic acid-ligand conjugate with the sensor surface. In other aspects, it is possible to adjust the quantity of ligand immobilized on the sensor surface up to the complexing capacity of the surface, by simple sequential addition of small quantities of boronic acid-ligand conjugate to the sensor surface. In this way, optimal surface loadings with a ligand may be achieved for any particular application. In other aspects, it is possible to take advantage of the reversibility of the boronic acid complex to remove the immobilized ligand from the sensor surface. In this way, spent or degraded ligands on the sensor surface can be facilely removed and replaced with fresh ligand. Other benefits and advantages will become more apparent when considered with the accompanying detailed description, drawings and examples that follow.

DESCRIPTION OF THE DRAWINGS

FIG. 3 depicts a reaction scheme for the preparation of a compound of Formula IV.

FIG. 4 depicts a reaction scheme for the preparation of a compound of Formula V.

I. DEFINITIONS

Figure 1:
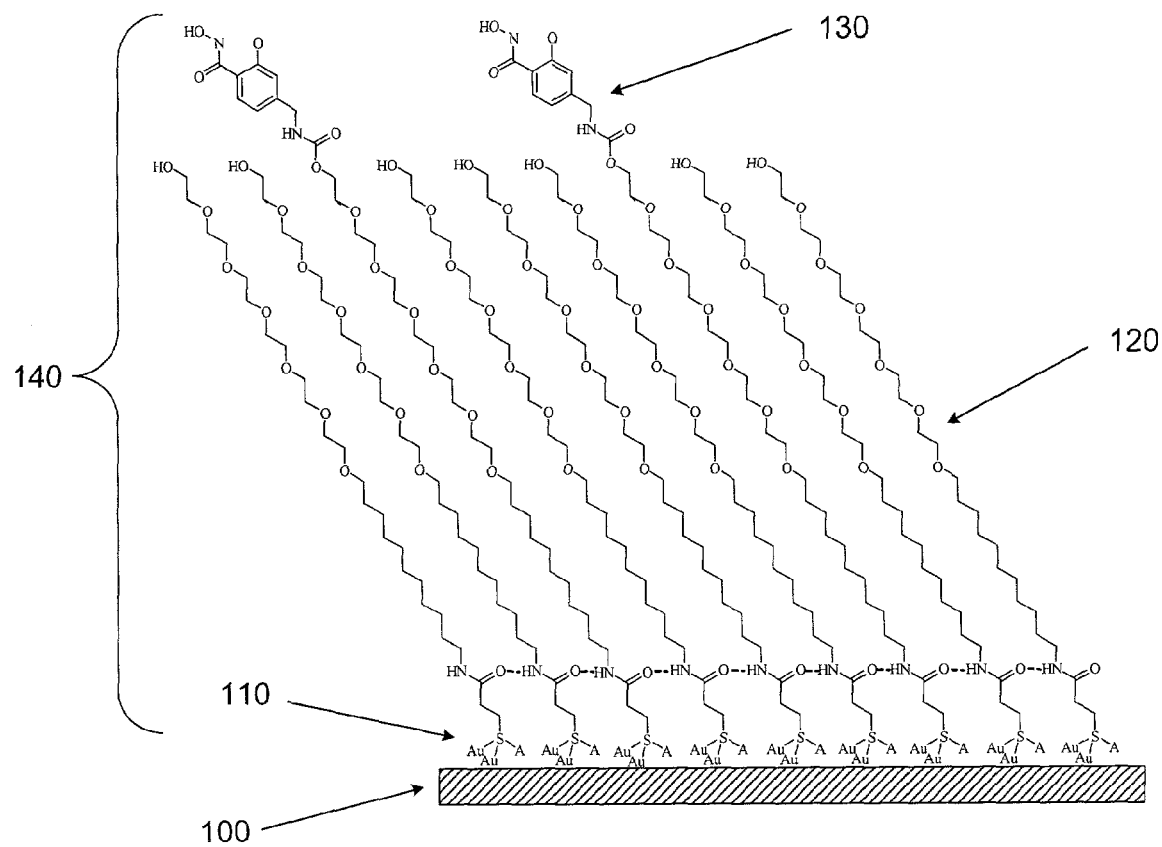
FIG. 1 illustrates one embodiment of a sensor substrate coated with a thin coating of gold, which is then reacted with a pair of thiol-containing compounds. In this embodiment, the treatment results in the formation of a binary self-assembled monolayer on the gold coating.

The term "biological binding pair" refers to any two molecules that exhibit mutual affinity or binding capability, including biochemical, physiological and/or pharmaceutical interactions. Often the pair will be referred to as a "ligand-analyte" pair in the context of BIA. Typical examples of biological binding pairs include: antibody/antigen, antibody/hapten, enzyme/substrate, enzyme/inhibitor, enzyme/cofactor, DNA/DNA, DNA/RNA, RNA/RNA, protein/nucleic acid, lectin/carbohydrate, receptor/hormone, receptor/effector, ligand/cell surface receptor, ligand/virus, and the like.

The term "BAS" refers to a bioactive species or a biologically active species or a ligand including, but not limited to, a protein, a polypeptide, a polypeptide fragment, a nucleic acid, a carbohydrate, a receptor, a hormone, a toxin, a vesicle, a liposome, and a cell.

The term "BACM" refers to any member of a broad class of boronic acid complexing moieties.

The term "PBA" refers to a broad class of boron-containing compounds which complex with a BACM. In certain preferred aspects, it refers to a phenylboronic acid moiety.

The term "self-assembled monolayer" refers to a relatively ordered assembly of molecules spontaneously chemisorbed on a surface, in which the molecules are ordered roughly parallel to each other and roughly perpendicular to the surface. Each of the molecules includes a functional group that adheres to the surface, and a portion that interacts with the neighboring molecules in the monolayer to form the relatively ordered array. See Laibinis, P. E., Hickman, J., Wrighton, M. S. and Whitesides, G. M. (1989) *Science* 245, 845; Bain, C., Evall, J. and Whitesides, G. M. (1989) *J. Am. Chem. Soc.* 111, 7155–7164; and Bain, C. and Whitesides, G. M. (1989) *J. Am. Chem. Soc.* 111, 7164–7175, each of which is incorporated herein by reference.

The term "SAM" refers to a self-assembled monolayer of a single organic compound.

The term "mSAM" refers to a self-assembled monolayer of two or more organic compounds.

The term "OEG" refers to an oligo(ethylene glycol), which is a polymer of about 1 to about 50 ethylene oxide units.

The term "PEG" refers to a poly(ethylene glycol), which is a polymer of greater than about 50 ethylene oxide units.

The term "immobilized", used with respect to a species, an art recognized meaning and refers to a condition in which the species is attached to a surface with an attractive force stronger than the attractive forces that are present in the intended environment of use of the surface and that act on the species, for example, solvating and turbulent forces. Coordinate and covalent bonds are representative of attractive forces stronger than typical environmental forces.

The term "non-specific binding" or "NSB" refers to interaction between any species, present in a medium from which a biological molecule or analyte is desirably captured, and a binding partner or other species immobilized at a surface, or the surface itself, other than the desired biological binding between the biological molecule and the binding partner.

DETAILED DESCRIPTION OF THE INVENTION AND PREFERRED EMBODIMENTS

II. Sensor Surface Chemistry

Biomolecular interaction analysis is the measurement of interaction or binding of one or more analytes to a biologically active species or ligand on a sensor surface. If the sensor is based on surface plasmon resonance, the interaction of an analyte with a ligand changes the refractive index at the surface. This change is detected for example, as a shift in the angle or wavelength of light at which surface plasmon resonance occurs. The magnitude of the shift in angle or wavelength is an indication of the strength of the interaction (affinity). The rate-of-change of the angle or wavelength with respect to time is used to determine the rate at which the binding occurs.

In one embodiment, the present invention provides a sensor surface, the sensor surface comprising: a substrate coated with a free electron metal; and a matrix layer disposed on the free electron metal, wherein the matrix layer comprises an organic compound having a boronic acid complexing moiety. In certain aspects, the organic compound "presents" a boronic acid complexing moiety for complexation with a phenylboronic acid. The matrix is preferably a self-assembled monolayer (SAM) or, more preferably, a mixed self-assembled monolayer (mSAM).

In certain aspects, the matrix layer comprises an organic compound having a boronic acid complexing moiety (BACM). The BACM complexes with a boronic acid, such as a phenylboronic acid or derivatives thereof. The term "BACM", as used herein, includes a broad class of boronic acid complexing moieties. The phrase "phenylboronic acid" (or "PBA") is used herein to include a broad class of boron-containing compounds which complex with the BACM.

In the present invention, boronic acid complexing moieties are utilized with a boronic acid moiety, such as PBA, to facilitate chemical immobilization of a biologically active species (BAS) to a sensor surface. The interaction between a BACM and a PBA-conjugated BAS results in, for example, a reversible, non-covalent coordination complex. Suitable BAS include, but are not limited to, a protein, a polypeptide, a polypeptide fragment, a nucleic acid, a carbohydrate, a receptor, a hormone, a toxin, a vesicle, a liposome, a cell, and the like. In sensor operation, the BAS has an affinity for an analyte of interest. Using the boronic acid chemistry of the present invention, it is possible to accurately measure the interaction of one or more analytes to a PBA-conjugated BAS immobilized on the sensor surface by virtue of complex formation with a BACM.

FIG. 1 depicts a typical embodiment of the present invention. This diagram is merely an illustration and should not be assumed to limit the scope of the claims herein. One of ordinary skill in the art will recognize other variations, modifications, and alternatives to the specifics of this diagram. As shown therein, the sensor substrate 100 is coated with a thin coating of free electron metal such as gold 110. The gold coating is then reacted, such as simultaneously, sequentially, or the like, with a pair of thiol-containing compounds, one of which terminates in a hydroxyl group 120 and the other in a boronic acid complexing moiety 130 (e.g., salicylhydroxamic acid (SHA)). This treatment results in the formation of a self-assembled monolayer 140 (such as a binary SAM) on the gold coating and provides a matrix for immobilization of a biologically active species. It should be recognized that either of the two thiol-containing compounds, 120 or 130, may be used by itself to form a unitary self-assembled monolayer. Additionally, it is possible to use mixtures of three or more thiol-containing compounds to form ternary, quaternary, and the like, SAMs.

As described above, the sensor surface of the present invention comprises a matrix layer, preferably a self-assembled monolayer, of one or more organic compounds, at least one of which, in turn, comprises a boronic acid complexing moiety (BACM). In one aspect, the organic compound having the BACM is of the formula:

X—R—Y (I)

wherein X, R and Y are as defined previously. The anchor group X forms a stable coordination complex with the free electron metal (e.g., Au coating on the sensor substrate). Suitable free electron metals include, but are not limited to, gold, silver, aluminum, copper, palladium and platinum. Those of skill in the art will know of other free electron metals suitable for use in the present invention.

In certain instances, the choice of metal depends upon the particular detection technology employed with the sensor. In the case of surface plasmon resonance sensors, the free electron metal is preferably gold. Anchor groups for free electron metals include, but are not limited to, thiol, disulfide and phosphine functional groups. The adsorption of the organic compound to the free electron metal is dependent upon the correct pairing of anchor group X with the free electron metal of choice. Thus, thiol or disulfide anchor groups are particularly suited for gold- or silver-coated surfaces, while phosphine anchor groups are suitable for a palladium-coated surface. If the free electron metal has an oxide coating, then a carboxylate, a sulfonate, a phosphate, an alkoxysilane or a chlorosilane group is suitable as an anchor group.

In certain preferred embodiments, the anchor group is not attached directly to the BACM, but can be linked via a spacer molecule, R. Preferably, the spacer molecule is flexible. Thus, R preferably contains an alkylene group of formula $(CH_2)_n$, optionally interrupted by a heteroatom, and is at least about 8 carbon equivalents in length. More preferably, R is an optionally substituted alkylene group, optionally interrupted by a heteroatom, which is about 8 to about 40 carbon equivalents in length.

In certain aspects, one end of the spacer group R comprises the anchor group X. The other end of the spacer group R, which faces away from the free electron metal following self-assembled monolayer formation, comprises one or several linking groups by which the BACM or a component thereof, is attached to R. These linking groups include, but are not limited to, groups that inhibit nonspecific binding of ligands or analytes to the matrix layer, such as an OEG, a PEG, a branched OEG, a branched PEG, an oligo(peptide), an oligo(propylene sulfoxide), a sugar (e.g., monosaccharide, disaccharide, and the like), a sugar alcohol (e.g., an alditol), and a dendrimer.

In a preferred embodiment, R includes an amide bond, as in the formula:

X—(CH$_2$)$_n$—NHC(O)—R'—Y     (Ia)

or

X—(CH$_2$)$_n$—C(O)NH—R'—Y     (Ib)

wherein X and Y are as defined previously. R', in Formulae Ia and Ib, is an optionally substituted alkylene group, optionally interrupted by a heteroatom, which is about 8 to about 30 carbon equivalents in length. The index "n" of the oligo(methylene) group in Formulae IIa and IIb is an integer from 1 to 5. Advantageously, the presence of this amide bond substantially increases the thermal stability of matrix layer.

In certain other aspects, the organic compound comprising a BACM is of the formula:

X—R-NSBI-Y     (II)

wherein n, R, NSBI and Y are as previously defined. As discussed above, in a preferred embodiment, R includes the presence of an amide bond, as in the formula:

X—(CH$_2$)$_n$—NHC(O)—R'-NSBI-Y     (IIa)

or

X—(CH$_2$)$_n$—C(O)NH—R'-NSBI-Y     (IIb)

As discussed above, in Formulae IIa and IIb, the R of Formula II comprises an amide bond, an oligo(methylene) group and R'. The index "n" of the oligo(methylene) group in Formulae IIa and IIb is an integer from 1 to about 5. R', in Formulae Ia and Ib, is an optionally substituted alkylene group, optionally interrupted by a heteroatom, which is about 8 to about 30 carbon equivalents in length. The nonspecific binding inhibitor, NSBI, is preferably an oligo(ethylene glycol) moiety containing form about 1 to about 15 ethylene oxide units, and is terminated in a hydroxyl or amino group to facilitate attachment of Y, the BACM.

The BACM interacts with a boronic acid, such as PBA or derivatives thereof, to form a boronic acid complex. This is accomplished by contacting the BACM and the boronic acid and incubating for a period of time. In general, for immobilization of a PBA-conjugated ligand on the matrix layer on the sensor, the ligand will be in aqueous solution. Advantageously, the complexation reaction is insensitive to variations in the ionic strength and the pH of the solution, as well as to the presence of organic co-solvents (e.g., used to help dissolve analytes of low water solubility), detergents (e.g., used to solubilize and stabilize solutions of hydrophobic analytes such as membrane proteins), and chaotropic agents (e.g., protein and nucleic acid denaturants). This is in contrast to systems such as biotin-avidin and digoxigenin-α-digoxigenin, which are more limited in the solution conditions under which effective immobilization can be obtained due to the need to maintain the three-dimensional structure of the biological macromolecule.

In one embodiment, the BACM has the formula:

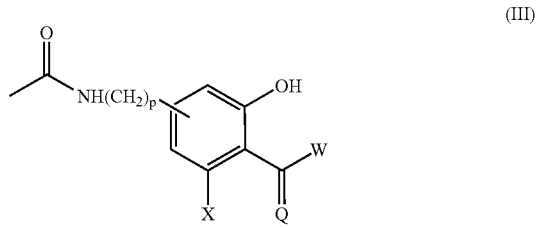

(III)

wherein p, Q, W and X are as previously defined. Compounds of Formula III can be made by a variety of methods. In preferred embodiments, Q is O (oxygen), X is H or OH, W is NHOH, and the index "p" is 1. The compounds of Formula III may be derived from either 4- or 5-methylsalicylic acid (X═H) or 3- or 4-methyl-2,6-dihydroxybenzoic acid (X═OH). In each instance, the compound may be prepared from a synthetic intermediate which is either a lower alkyl 4- or 5-methylsalicylate (X═H), or a lower alkyl 3- or 4-methyl-2,6-dihydroxybenzoate (for detailed preparation of these compounds, see, U.S. Pat. Nos. 5,774,627; 5,777,148; 5,837,878; 5,847,192; 5,859,210; 5,869,623; 5,872,224; and 5,877,297; the teachings of each of which are incorporated herein by reference in their entirety for all purposes).

In certain aspects of the invention, the matrix layer is made up of a binary mixture of organic compounds terminated in a BACM such as one of the type depicted in Formulae I, Ia, Ib, II, IIa or IIb, and an organic compound of similar and related structure terminated not in a BACM, but rather in an uncharged, unreactive group, as in the formula:

X—R-Z     (VI)

or

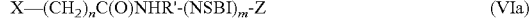

X—(CH$_2$)$_n$C(O)NHR'-(NSBI)$_m$-Z     (VIa)

or

X—(CH$_2$)$_n$NHC(O)R'-(NSBI)$_m$-Z     (VIb)

wherein X, n, R', NSBI, m and Z are as defined previously. Such uncharged, unreactive groups include, but are not limited to, H, CH$_3$, OH, OCH$_3$, CO$_2$CH$_3$, C(O)NH$_2$, C(O)NHCH$_3$, C(O)N(CH$_3$)$_2$ or SO$_2$NH$_2$. Preferred groups in this context include, for example, hydrophilic groups such as OH and OCH$_3$, in order to minimize or eliminate nonspecific binding. In general, the matrix comprising the mixed self-assembled monolayer from such a binary mixture of organic compounds contains from about 1 mole % to about 30 mole % of the BACM-terminated compound; preferably, it contains from about 2 mole % to about 20 mole %; and most preferably, it contains from about 4 mole % to about 10 mole %.

In one embodiment, the sensor surface comprises SCH$_2$C(O)NH(CH$_2$)$_{11}$(OCH$_2$CH$_2$)$_{11}$OC(O)Y (Polymer A) and —SCH$_2$C(O)NH—(CH$_2$)$_{11}$(OCH$_2$CH$_2$)$_3$OH (Polymer B).

In certain aspects, the mole percent of Polymer A is less than about 10% of the total mole percent of Polymer A and Polymer B together. In another aspect, the mole percent of the Polymer A is less than about 5% of the total mole percent of Polymer A and Polymer B.

Use of a binary SAM is advantageous as it provides minimum nonspecific binding to the matrix layer, and allows for optimization of immobilized ligand density for particular applications of the sensor.

In one preferred embodiment, the organic compound having a BACM attached thereto is of the formula:

HS(CH$_2$)$_n$C(O)NHR'—NSBI—SHA    (IV)

wherein n, R', NSBI and SHA are as defined previously. In an especially preferred embodiment, n is 2, R' is (CH$_2$)$_{11}$, NSBI is (OCH$_2$CH$_2$)$_6$, and SHA is bound to NSBI through a carbamate linkage as in Formula III (p=1). FIG. 3 sets forth a preferred compound of Formula IV.

In another preferred embodiment, the organic compound having a BACM attached thereto is of the formula:

HS(CH$_2$)$_n$C(O)NHR'-NSBI-DHBHA    (V)

wherein n, R', NSBI and DHBHA are as defined previously. In an especially preferred embodiment, n is 2, R' is (CH$_2$)$_{11}$, NSBI is (OCH$_2$CH$_2$)$_6$, and DHBHA is bound to NSBI through a carbamate linkage as in Formula III (p=1). FIG. 4 sets forth a preferred compound of Formula V.

In a preferred embodiment, the matrix layer comprises a binary mSAM of organic compound of Formula IV having a BACM bound thereto and a compound of formula:

HS(CH$_2$)$_n$C(O)NHR'-NSBI-Z    (VIII)

wherein n, R', NSBI and Z are as defined previously. In an especially preferred embodiment, n is 2, R' is (CH$_2$)$_{11}$, NSBI is (OCH$_2$CH$_2$)$_6$, and Z is OH. In another preferred embodiment, the matrix layer comprises a binary mSAM of organic compound of Formula V having a BACM thereto affixed and a compound of Formula VIII. In an especially preferred embodiment, n is 2, R' is (CH$_2$)$_{11}$, NSBI is (OCH$_2$CH$_2$)$_6$, and Z is OH.

In certain embodiments, the present invention provides a sensor surface comprising: a substrate coated with a free electron metal; a matrix layer disposed on the free electron metal, wherein the matrix layer comprises an organic compound having a boronic acid complexing moiety; and a boronic acid moiety complexed to the boronic acid complexing moiety. Preferably, the boronic acid moiety comprises a boronic acid reagent conjugated to a biologically active species.

In certain aspects, the boronic acid moiety has the formula:

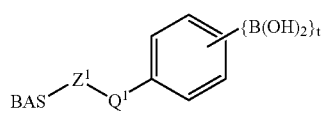

(VII)

In Formula VII, BAS is a bioactive species including, but not limited to, a protein, a polypeptide, a polypeptide fragment, a nucleic acid, a carbohydrate, a receptor, a hormone, a toxin, a vesicle, a liposome, and a cell. Z$^1$, if present, in Formula VII, is a spacer group including, but not limited to, a saturated or unsaturated aliphatic chain of 0 to about 6 carbon equivalents in length, an unbranched saturated or unsaturated aliphatic chain of from about 6 to about 18 carbon equivalents in length with at least one intermediate amide or disulfide moiety, and an oligo(ethylene glycol) chain of from about 3 to about 12 carbon equivalents in length. Q$^1$, in Formula VII, is a linkage including, but not limited to, an amide, methyl amide, methylene, ether, thioether, methylene ether and methylene thioether moiety. The index "t", in Formula VII, is an integer from 1 to 3.

In certain preferred aspects, t is 1. In these aspects, the boronic acid functional group is preferably meta or para to Q$^1$. As such, the present invention provides boronic acid moieties of the following formulae:

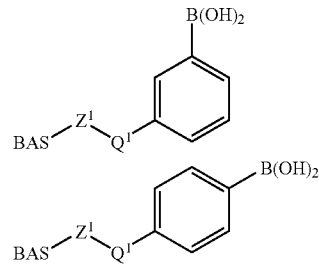

In certain other preferred aspects, t is 2. In these aspects, the boronic acid functional groups are preferably oriented 1,2 or 1,3 on the phenyl ring with respect to Q$^1$. As such, the present invention also provides boronic acid moieties of the following formulae:

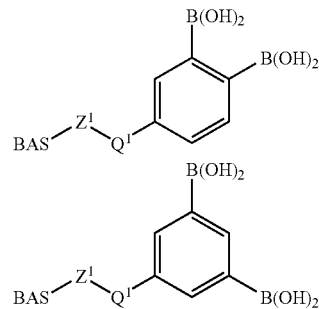

The most popular methods of synthesizing phenylboronic acids and phenylenediboronic acids involve in situ generation of arylmagnesium or aryllithium species from the corresponding aryl halides followed by transmetallation with a trialkoxyborate (see, Todd, M. H., Balasubramanian, S. and Abell, C. (1997) Tetrahedron Lett. 38, 6781–6784; Thompson, W. and Gaudino, J. (1984) J. Org. Chem. 49, 5237–5243; Crisofoli, W. A. and Keay, B. A. (1991) Tetrahedron Lett. 32, 5881–5884; Sharp, M. J., Cheng, W. and Sniekus, V. (1987) Tetrahedron Lett. 28, 5093–5096; and Larson, R. D., King, A. O., Cheng, C. Y., Corley, E. G., Foster, B. S., Roberts, F. E., Yang, C., Lieberman, D. R., Reamer, R. A., Tschaen, D. M, Verhoeven, T. R. and Reider, P. J. (1994) J. Org. Chem. 59, 6391–6394). Recently, transition metal-catalyzed cross-coupling reactions have been developed to produce phenylboronic acids from aryl halides and alkoxydiboron (Ishiyama, T.; Murata, M. and Miyaura, N. (1995) *J. Org. Chem.* 60, 7508–7510; and Giroux, A., Han, Y. and Prasit, P. (1997) *Tetrahedron Lett.* 38, 3841–3844) or bialkoxyhydroborane (Murata, M., Watanabe, S., and Masuda, Y. (1997) *J. Org. Chem.* 62, 6458–6459) using $PdCl_2(dppf)$ as the catalyst. Additionally, a palladium-catalyzed solid-phase boronation reaction, using alkoxydiboron, has been reported using a polymer-bound aryl halide (Piettre, S. R. and Baltzer, S. (1997) *Tetrahedron Lett.* 38, 1197–1200).

The preparation of 1,2-phenylenediboronic acid has been previously described (see, Clement, R. and Thiais, F. (1966) *Hebd. Seances Acad. Sci., Ser. C* 263, 1398–1400). The preparation of 1,2-phenylenediboronate complexes prepared from (1,2-phenylene)bis[(4R,5R)-4,5-diphenyl-1,3,2dioxaborolane], involving addition of either one or two equivalents of benzylamine, has recently been described (see, Nozaki, K., Yoshida, M. and Takaya, H., (1994) *Angew, Chem, Int. Ed. Engl.* 33, 2452–2454; and Nozaki, K., Yoshida, M. and Takaya, H., (1996) *Bull. Chem. Soc. Jpn.* 69, 2043–2052).

Figure 2:
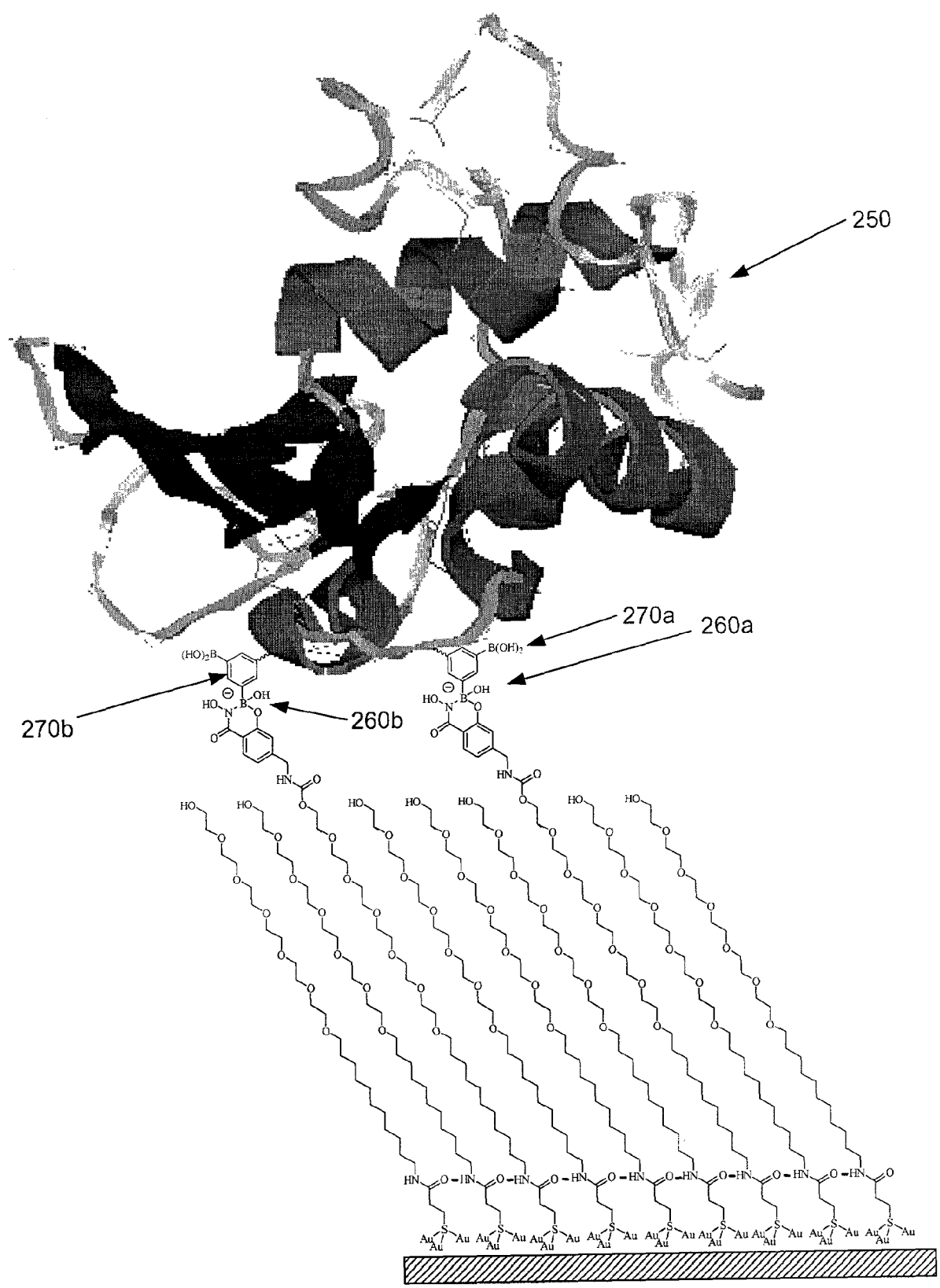
FIG. 2 illustrates one embodiment of a phenylenediboronic acid (PDBA) conjugated protein immobilized on a sensor surface.

FIG. 2 illustrates one embodiment of the present invention, wherein a phenylenediboronic acid (PDBA) conjugated protein 250 is immobilized on a sensor surface by virtue of formation of boronic acid complexes 260a, 260b with boronic acid complexing moieties (e.g., 130 in FIG. 1). The interaction between a boronic acid complexing moiety and a boronic acid moiety preferably results in a reversible, non-covalent coordination complex. In certain applications, boronic acid moieties comprising a boronic acid reagent 270a, 270b conjugated to a bioactive species 250 is complexed or conjugated to the boronic acid complexing moiety (e.g., 130 in FIG. 1) of the matrix of the sensor surface.

It should be noted that, for many BAS, the boronic acid will typically attach to more than one reactive site on the BAS. If, for example, the BAS is a protein 250, multiple boronic acids will react with the protein, each boronic acid reacting at one of several sites on the protein. A complex can be with at least one bioactive species 250 having one or more pendant phenylboronic acid or phenylenediboronic acid moieties comprising boronic acid reagents 270a, 270b, complexed with one or more boronic acid complexing moieties.

The chemical structure of the complex will, of course, depend upon the particular boronic acid moiety conjugated to the bioactive species.

Thus, in certain aspects, the bioconjugate formed by complexation of the boronic acid moiety comprising a phenylboronic acid moiety and a BAS is of the formula:

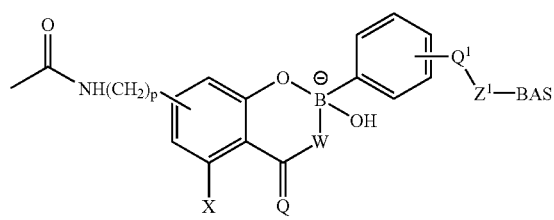

wherein X, Q, W, $Q^1$, $Z^1$, p and BAS are as previously defined. In other aspects, the bioconjugate formed by complexation of the boronic acid moiety comprising a 1,3- or 1,4-phenylenediboronic acid moiety and a BAS is of the formula:

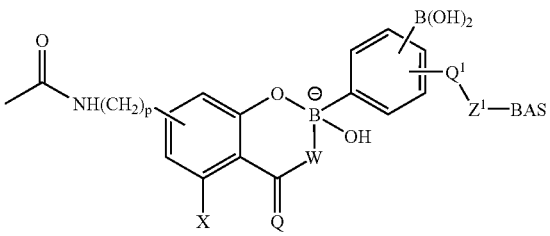

wherein X, Q, W, $Q^1$, $Z^1$, p and BAS are as previously defined. In other aspects, the bioconjugate formed by complexation of the boronic acid moiety comprising a 1,2-phenylenediboronic acid moiety and a BAS is of the formula:

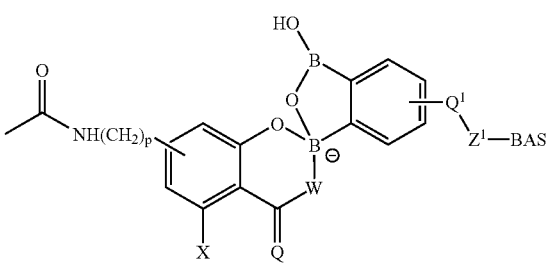

wherein X, Q, W, $Q^1$, $Z^1$, p and BAS are as previously defined.

Advantageously, the bioconjugate complex can be prepared in buffered aqueous solution, or in organic solvents, or in mixtures of aqueous buffers and water-miscible organic solvents. The bioconjugate is formed within a few minutes over a range of temperatures, for example, from about 4° C. to about 70° C. The bioconjugate can be formed over a wide range of pH and ionic strength, and in the presence of detergents or chaotropes (e.g., protein and nucleic acid denaturants). Once formed, the bioconjugate is stable to an even broader range of pH, ionic strength, detergent concentrations and chaotrope concentrations.

As used herein, BAS represents a biologically active species which may or may not contain a portion of a reactive moiety used to attach the bioactive species to a boronic acid moiety, such as a phenylboronic acid moiety. In one aspect, the BAS is typically a ligand for an analyte of interest. The BAS and the analyte of interest specifically interact with one another, thereby forming a biological binding pair. "Specific binding" of the first member pair, e.g., the BAS, to the second member of the binding pair, e.g., the analyte, in a sample is evidenced by the binding of the first member to the second member, or vice versa, with greater affinity (and/or specificity) than to the other components of the sample. The binding between the members of the binding pair is typically non-covalent, although the present invention is not so limited. In sensor applications, any BAS that has an affinity for an analyte of interest can be used with the methods of the present invention.

In certain preferred embodiments, attachment of the boronic acid to the BAS involves the stacking of ligands. For instance, in one embodiment, a boronic acid moiety is covalently attached to avidin or streptavidin which, in turn, is non-covalently attached to a biotinylated ligand that is capable of selectively binding an analyte of interest (e.g., a biotinylated antibody). Using such stacking methodologies, the BAS can be any small molecule that is capable of binding to an analyte of interest.

Exemplary biological binding pairs suitable for use with the methods of the present invention include, but are not limited to, any haptenic or antigenic compound in combination with a corresponding antibody or binding portion or fragment thereof (e.g., digoxigenin and anti-digoxigenin; fluorescein and anti-fluorescein; dinitrophenol and anti-dinitrophenol; bromodeoxyuridine and anti-bromodeoxyuridine; mouse immunoglobulin and goat anti-mouse immunoglobulin) and nonimmunological binding pairs (e.g. biotin and avidin; biotin and streptavidin; hormone (e.g., thyroxine or cortisol) and hormone binding protein; receptor and receptor agonist or antagonist; immunoglobulin G and protein A; lectin and carbohydrate; enzyme and enzyme cofactor; enzyme and enzyme inhibitor; complementary polynucleotide pairs capable of forming nucleic acid duplexes or triplexes; and the like. Those of skill in the art will know of other biological binding pairs suitable for use in the present invention.

III. Use in Sensor Applications

Sensors using the surfaces of the present invention can be used in a variety of applications, including biosensor applications, test assays, and the like. The term "test assay" generally refers to any procedure in which a member of a biological binding pair is to be specifically captured from a medium in which it is dispersed or is expected to be dispersed. For example, "test assay" can be used to describe a diagnostic procedure, analytical procedure, microanalytical procedure, forensic analysis, pharmacokinetic study, cell sorting procedure, affinity chromatographic separation, laboratory or industrial characterization or recovery of one or more species such as toxins, catalysts, starting materials or products, and the like. Biosensing applications include those such as drug screening, environmental monitoring, medical diagnostics, quality control in the pharmaceutical and food industries, and other areas in which it is advantageous to sensitively measure the interaction between biological binding partners.

As such, in one embodiment, the present invention provides a method for detecting an analyte, the method comprising: providing a sensor comprising a substrate coated with a free electron metal, a matrix layer disposed on the free electron metal, the matrix layer comprising an organic compound, wherein the organic compound has a boronic acid complexing moiety and, a boronic acid moiety complexed to the boronic acid complexing moiety; and contacting the sensor with the analyte to elicit a response; and measuring the response, thereby detecting the analyte. In preferred embodiments, the boronic acid moiety comprises a boronic acid conjugated to a BAS that is capable of specifically binding an analyte of interest.

Various responses include, for example, an electrical response, an optical response, a refractive index change, a shift in the angle or wavelength of light such as at which surface plasmon resonance occurs, a fluorescence response, a color change, and combinations thereof.

Information that can be obtained using the sensors of the present invention includes, but is not limited to, kinetic measurements, which provide, for example, information on the rates at which interacting molecules bind to each other and break apart; affinity determinations, which provide details on the way in which a biological process occurs and is controlled; specificity studies, which examine, for example, the ability of one molecule to bind to another molecule to the exclusion of others; and concentration measurements, which determine, for example, the amount of an active molecule that is present in a sample.

Advantages of the sensors of the present invention include, but are not limited to, tailored immobilization of ligands; label-free detection; analysis without purification; continuous monitoring; real-time monitoring; high sensitivity of detection; facile preparation and regeneration; stability at increased temperature; minimal non-specific binding; and the like.

In certain embodiments, the present invention provides for arrays of sensors (e.g., at least two sensors). For example, the sensor array may be a cartridge containing eight individual sensors operating individually or simultaneously. Alternatively, the sensor array may be made up of 96 individual sensors disposed in a multi-well plate. In certain methods, the array of sensors contains the same ligand immobilized on the surface of all sensors in the array; the array is then contacted with a plurality of analytes to analyze their various interactions with the ligand. In certain other methods, a plurality of ligands are immobilized on the surface of the array of sensors, wherein at least two sensors have a different ligand; the array is then contacted with a single analyte of interest to analyze its interaction with the various ligands. Clearly, any combination of ligands and analytes can be utilized with the array, in particular, to make replicate measurements on multiple analytes and ligands. Additionally, certain sensors in the array can be employed as references to determine the level of non-specific responses. As such, the sensor array can be tailored to specific analytes or ligands and to specific assays and applications.

In certain aspects, a single sensor may have an array of differently mixed monolayers patterned on its surface in a spatially distinct manner. Advantageously, this patterning can be used on a single sensor to detect a plurality of analytes by immobilizing different ligands on the spatially distinct elements of the array.

In other aspects, the array of sensors are compositionally different. For example, the sensor array may contain a pH sensor, a temperature probe sensor, a humidity sensor, a color sensor, a sensor as described herein, and the like.

In another aspect, the present invention provides a sensor surface, comprising: a substrate coated with a free electron metal; a matrix layer disposed on the free electron metal, the matrix layer comprising an organic compound, wherein the organic compound has the formula

X—R¹-BAS

X is an anchor group that forms a complex with the free-electron metal; $R^1$ is an optionally substituted alkylene group having an amido group; and BAS is a bioactive species.

IV. EXAMPLES

The following Examples are presented solely to provide a more complete understanding of the invention. The Examples do not in any way limit the scope of the invention disclosed and claimed herein.

Example 1

Synthesis of N-(11-{2-[2-(2-Hydroxy-ethoxy)-ethoxy]-ethoxy}-undecyl)-3-mercaptopropionamide (6)

A) Synthesis of 11-tert-Butoxycarbonylamino-undecanoic acid (1)

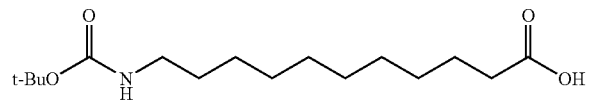

11-Aminoundecanoic acid (20.4 g, 101.3 mmol) and di-tert-butyldicarbonate (24.3 g, 111.0 mmol) are suspended in water (300 mL) and methanol (150 mL). Aqueous sodium hydroxide (3.13 M, 65 mL) is added, and the mixture is stirred at room temperature. After 30 minutes, the mixture became homogenous. After stirring for a total of 6 hours, the methanol was removed in vacuo. Ethyl acetate (500 mL) was added to the aqueous solution. Aqueous hydrochloric acid (1 N, 300 mL) was added slowly to the stirred mixture until the evolution of gas ceased. The pH was tested with pH paper and determined to be 4 to 5 at this point. The layers were separated, and the ethyl acetate solution was extracted sequentially with aqueous hydrochloric acid (1 N, 250 mL, water (250 mL) and brine (150 mL). The organic phase was then dried over anhydrous magnesium sulfate, filtered and evaporated in vacuo to a thick oil. Upon cooling of the oil, a waxy solid was obtained (29.0 g, 95% yield). The material was used in the next step without further purification. $^1$H NMR (300 MHz, DMSO-$d_6$): δ 1.23 (br s, 12H), 1.30–1.38 (m, 11H), 1.43–1.52 (m, 2H), 2.18 (t, J=7.3 Hz, 2H), 2.88 (q, J=6.3 Hz, 2H), 6.73 (t, J=5.4 Hz, 1H), 11.95 (s, 1H). $^{13}$C NMR (75 MHz, DMSO-$d_6$): δ 24.50, 26.27, 28.26, 28.57, 28.72, 28.75, 28.86, 28.97, 29.48, 33.66, 77.23, 155.56, 174.47. HRMS (ESI-pos): calcd for $C_{16}H_{32}NO_4$ 302.2331, obsd 302.2328.

B) Synthesis of (11-Hydroxy-undecyl)carbamic acid tert-butyl ester (2)

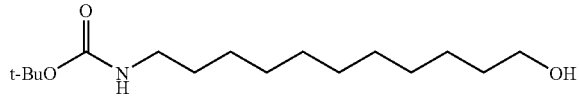

Compound 1 (29.0 g, 96.2 mmol) was dissolved in anhydrous tetrahydrofuran (500 mL). The solution was cooled to 0° C. under a dry inert atmosphere. Borane-tetrahydrofuran complex (1.0 M, 144 mL, 144 mmol) was added dropwise with stirring over 1 hour. The cooling bath was removed and the reaction was allowed to warm to room temperature and stirred an additional 2 hours. The reaction was then quenched by the slow, careful addition of saturated aqueous sodium bicarbonate solution (100 mL). The mixture was diluted with water (400 mL), and the tetrahydrofuran was removed in vacuo. The resulting mixture was extracted three times with ethyl acetate (200 mL portions), and the organic extracts were combined. The ethyl acetate solution was washed with brine (100 mL), dried over anhydrous magnesium sulfate, filtered, and evaporated in vacuo. A white waxy solid was obtained (27.1 g, 98% yield), which was used in the next step without further purification. $^1$H NMR (300 MHz, DMSO-$d_6$): δ 1.23 (m, 14H), 1.30–1.43 (m, 13H), 2.88 (q, J=6.7 Hz, 2H), 3.36 (q, J=6.3 Hz, 2H), 4.31 (t, J=5.1 Hz, 1H), 6.74 (t, J=5.2 Hz, 1H). $^{13}$C NMR (75 MHz, DMSO-$d_6$): δ 25.13, 26.27, 28.25, 28.74, 28.98, 29.03, 29.11, 29.48, 32.56, 60.72, 77.21, 155.55. HRMS (ESI-pos): calcd for $C_{16}H_{34}NO_3$ 288.2539, obsd 288.2535.

C) Synthesis of Methanesulfonic Acid 11-tert-butoxycarbonylamino-undecyl Ester (3)

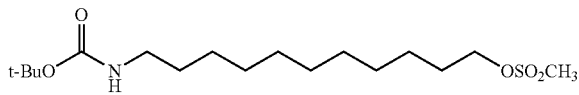

Compound 2 (138.3 mmol) was dissolved in dichloromethane (1.75 L) containing triethylamine (100 mL, 717.5 mmol). The solution was stirred and cooled to 0° C., and methanesulfonyl chloride (52.0 mL, 670.0 mmol) was added dropwise over 3.5 hours. The reaction was stirred for an additional hour, then washed sequentially with aqueous hydrochloric acid (1 N, 750 mL), water (500 mL) and brine (300 mL). The organic layer was dried over anhydrous magnesium sulfate, filtered and the volume reduced to approximately 250 mL in vacuo. The solution was allowed to stand at 4° C. overnight, during which time a white solid formed. The solid was collected by filtration and dried in vacuo (obtained 100.2 g, 57% yield). Additional product was obtained by evaporating the filtrate in vacuo, and crystallizing the resulting material from ethyl acetate and hexanes (obtained 41.2 g, , 23% yield). $^1$H NMR (300 MHz, DMSO-$d_6$): δ 1.24 (br s, 14H), 1.29–1.38 (m, 11H), 1.64 (p, J=7.0 Hz, 2H), 2.88 (q, J=6.3 Hz, 2H), 3.15 (s, 3H), 4.17 (t, J=6.5 Hz, 2H), 6.74 (t, J=5.4 Hz, 1H). $^{13}$C NMR (75 MHz, DMSO-$d_6$): δ 24.89, 26.26, 28.25, 28.46, 28.50, 28.71, 28.88, 28.97, 29.47, 36.51, 70.41, 77.23, 155.55. HRMS (ESI-pos): calcd for $C_{17}H_{36}NO_5S$ 366.2314, obsd 366.2310.

D) Synthesis of (11-{2-[2-(2-hydroxy-ethoxy)-ethoxy]-ethoxy}-undecyl)-carbamic acid tert-butyl ester (4)

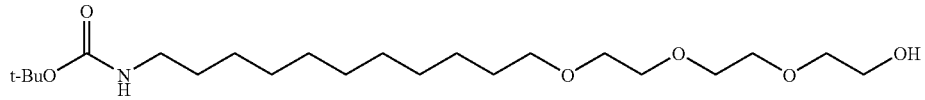

Tri(ethylene glycol) (47.0 mL, 352.0 mmol) was added to a round bottom flask (100 mL) and heated to 110° C. Aqueous sodium hydroxide solution (50% [w/v], 2.80 mL, 35.0 mmol) was added, and the solution was stirred for 45 minutes at 110° C. Compound 3 (12.8 g, 35.0 mmol) was added to the hot solution, and stirring was continued for 8 hours at 110° C. The reaction mixture was then cooled to room temperature, and diluted with water (300 mL). The aqueous solution was extracted three times with ethyl acetate (150 mL portions). The combined ethyl acetate extracts were dried over anhydrous magnesium sulfate, filtered and evaporated in vacuo. The crude product was purified by chromatography on silica gel (200 g, gradient of dichloromethane to 5% [v/v] methanol in dichloromethane). The product containing fractions were pooled and evaporated in vacuo to give an oil (10.6 g, 72% yield). $^1$H NMR (300 MHz, DMSO-$d_6$): δ 1.23 (br s, 14H), 1.30–1.38 (m, 11H), 1.42–1.51 (m, 2H), 2.88 (q, J=6.3 Hz, 2H), 3.32–3.51 (m, 14H), 4.55 (t, J=5.4 Hz, 1H), 6.72 (t, J=5.4 Hz, 1H). $^{13}$C NMR (75 MHz, DMSO-$d_6$): δ 25.65, 26.28, 28.23, 28.74, 28.90, 28.96, 29.02, 29.04, 29.22, 29.47, 60.22, 69.49, 69.78, 69.82, 69.85, 70.33, 72.36, 77.18, 155.53. HRMS (ESI-pos): calcd for $C_{22}H_{46}NO_6$ 420.3325, obsd 420.3331.

E) Synthesis of N-(11-{2-[2-(-hydroxy-ethoxy)-ethoxy]-ethoxy}-undecyl)-3-[2-(11-{2    -[2-(2-hydroxy-ethoxy)-ethoxy]-ethoxy}-undecylcarbamoyl)-ethyldisulfanyl]-propionamide (5)

Dithiopropionic acid (1.65 g, 7.85 mmol) was dissolved in anhydrous 1,4-dioxane (60 mL). The solution was stirred and N-hydroxysuccinimide (1.99 g, 17.3 mmol) was added, followed by N,N'-dicyclohexylcarbodiimide (3.57 g, 17.3 mmol). The reaction mixture was stirred for 16 hours at room temperature, then filtered.

In a separate flask, compound 4 (6.60 g, 15.7 mmol) was dissolved in 1,4-dioxane (40 mL) and a solution of hydrogen chloride in 1,4-dioxane (4 M, 38 mL, 152 mmol) was added. The mixture was stirred for 16 hours at room temperature.

The two reaction mixtures were then combined and N,N-diisopropylethylamine (26 mL) was added. Methanol (5 mL) was added to provide a homogeneous solution, and the reaction was stirred for 3 hours at room temperature. This crude reaction mixture was used without further purification in the next step.

F) Synthesis of N-(11-{2-[2-(-hydroxy-ethoxy)-ethoxy]-ethoxy}-undecyl)-3-mercaptopropionamide (6)

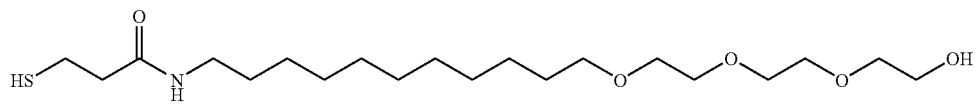

The crude reaction mixture containing compound 5 was treated with water (20 mL) and aqueous hydrochloric acid (4 M, 10 mL). Tris-carboxyethylphosphine hydrochloride (4.10 g, 14.3 mmol) was added, and the solution was stirred for 24 hours at room temperature. The organic solvents were removed in vacuo, and the residue was diluted with water (200 mL). The aqueous mixture was extracted three times with ethyl acetate (150 mL portions). The combined ethyl

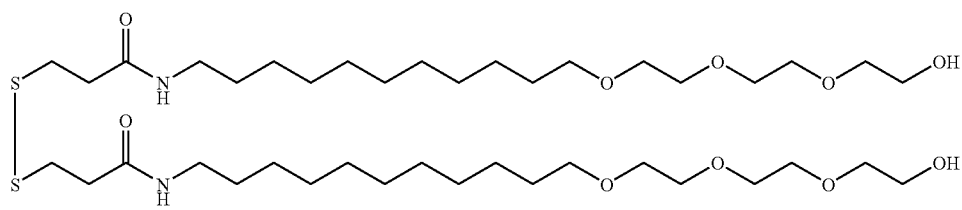

acetate extracts were washed sequentially with water (100 mL) and brine (75 mL), dried over anhydrous magnesium sulfate, filtered, and evaporated in vacuo. The crude product was purified by chromatography on silica gel (150 g, gradient of dichloromethane to 3% [v/v] methanol in dichloromethane). The product containing fractions were pooled and evaporated in vacuo to give a white solid (4.40 g, 75% yield). $^1$H NMR (300 MHz, DMSO-$d_6$): δ 1.43 (br s, 14H), 1.54–1.58 (m, 2H), 1.64–1.68 (m, 2H), 2.42 (t, J=7.5 Hz, 1H), 2.54 (t, J=6.9 Hz, 2H), 2.82 (q, J=7.8 Hz, 2H), 3.21 (q, J=5.7 Hz, 2H), 3.52–3.71 (m, 14H), 4.76 (t, J=5.4 Hz, 1H), 8.02 (t, J=5.4 Hz, 1H). $^{13}$C NMR (75 MHz, CDCl$_3$): 20.68, The product containing fractions were pooled and evaporated in vacuo to give an oil (8.17 g, 67% yield). $^1$H NMR (300 MHz, DMSO-$d_6$): δ 1.23 (br s, 14H), 1.31–1.40 (m, 11H), 1.41–1.53 (m, 2H), 2.88 (q, J=6.3 Hz, 2H), 3.33–3.51 (m, 26H), 4.57 (t, J=5.3 Hz, 1H), 6.74 (t, J=5.4 Hz, 1H). $^{13}$C NMR (75 MHz, DMSO-$d_6$): δ 25.64, 26.25, 28.23, 28.72, 28.88, 28.93, 29.00, 29.02, 29.21, 29.46, 60.20, 69.47, 69.79 (large broad), 70.30, 72.35, 77.20, 155.54. HRMS (ESI-pos): calcd for $C_{28}H_{58}NO_9$ 552.4112, obsd 552.4113.

B) Synthesis of (tert-Butoxy)-N-{11-[2-(2-{2-[2-(2-{2-[N-[{4-[N-( tert-butoxy)carbamoyl]-3-hydroxyphenyl}-methyl)carbamoyloxy]ethoxy}ethoxy)ethoxy]ethoxy}ethoxy)ethoxy]undecyl}-carboxamide (12)

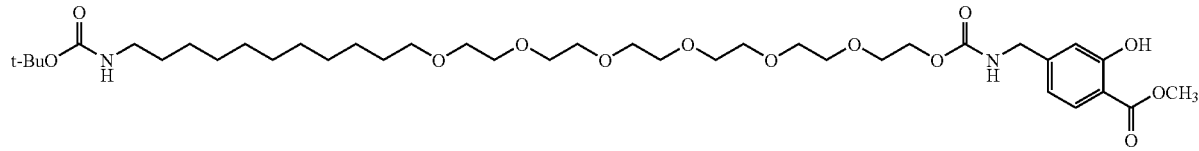

26.19, 27.04, 29.37, 29.56, 29.59, 29.61, 29.65, 29.71, 29.76, 39.78, 40.65, 61.88, 70.17, 70.52, 70.76, 71.70, 72.66, 170.74.. HRMS (ESI-pos): calcd for $C_{20}H_{42}NO_5S$ 408.2784, obsd 408.2783.

Example 2

Synthesis of (3-Hydroxy-4-hydroxycarbamoyl-benzyl)-carbamic Acid 2-(2-{2-[2-(2-{2-[11-(3-mercapto-propionylamino)-undecyloxy]-ethoxy}-ethoxy)-ethoxy]-ethoxy}-ethoxy)-ethyl Ester (14)

A) Synthesis of (11-{2-[2-(2-{2-[2-{2-hydroxy-ethoxy)-ethoxy]-ethoxy }-ethoxy)-ethoxy]-ethoxy}-undecyl)-carbamic Acid Tert-Butyl Ester (11)

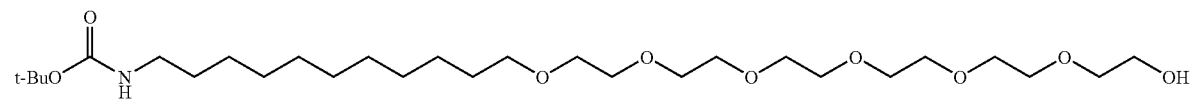

Hexa(ethylene glycol) (75.0 g, 267 mmol was added to a round bottom flask (100 mL) and heated to 110° C. Aqueous sodium hydroxide solution (50% [w/v], 1.80 mL, 22.5 mmol) was added, and the solution was stirred for 45 minutes at 110° C. Compound 3 (12.8 g, 35.0 mmol) was added to the hot solution, and stirring was continued for 8 hours at 110° C. The reaction mixture was then cooled to room temperature, and diluted with water (300 mL). The aqueous solution was extracted three times with ethyl acetate (150 mL portions). The combined ethyl acetate extracts were dried over anhydrous magnesium sulfate, filtered and evaporated in vacuo. The crude product was purified by chromatography on silica gel (200 g, gradient of dichloromethane to 5% [v/v] methanol in dichloromethane).

Compound 11 (10.6 g, 19.2 mmol) was dissolved in anhydrous N,N-dimethylformamide (40 mL) and N,N'-carbonyldiimidazole (3.43, 21.1 mmol) was added. The mixture was stirred at room temperature under a dry nitrogen atmosphere for 2 hours. Triethylamine (3.5 mL, 25.3 mmol) was added, followed by 4-aminomethyl-2-hydroxybenzoic acid methyl ester hydrochloride (6.5 g, 29.9 mmol). The mixture was stirred at 60–65° C. for 20 hours, then cooled to room temperature. The reaction mixture was diluted with water (150 mL) and extracted three times with ethyl acetate (100 mL portions). The combined organic solutions were washed with aqueous hydrochloric acid (1 N, 50 mL) and then twice with brine (50 mL portions). The organic layer was dried over anhydrous magnesium sulfate and filtered. The filtrate was concentrated in vacuo and the crude product was purified by chromatography on silica gel (200 g, gradient of dichloromethane to 5% [v/v] methanol in dichloromethane). The product containing fractions were pooled and evaporated in vacuo to give a yellowish oil (9.8 g, 69% yield). $^1$H NMR (300 MHz, DMSO-$d_6$): δ 10.52 (s, 1H), 7.83 (t, 1H, J=6.0 Hz), 7.73 (d, 1H, J=8.1 Hz), 6.84 (s, 1H), 6.82 (d, 1H, J=8.1 Hz), 6.72 (t, 1H, J=4.0 Hz), 4.18 (d, 2H, J=6.0 Hz), 4.09 (m, 2H), 3.88 (s, 3H), 3.58 (m, 2H), 3.52–1.15 (m, 20H), 3.35 (t, 2H, J=7.2 Hz), 2.88 (m, 2H), 1.55–1.15 (m, 27H).

C) Synthesis of N-(11-{2-[2-(2-{2-[2-(2-{methyl-2-hydroxy-4 -carbamoylmethylbenzoyl}-ethoxy)-ethoxy)-ethoxy]-ethoxy}-ethoxy)ethoxy]-ethoxy}-undecyl)-3-[2-(11-{2-[2-(2-{2-[2-(2-{methyl-2-hydroxy-4-carbamoylmethylbenzoyl}-ethoxy)-ethoxy]-ethoxy}-ethoxy)-ethoxy]-ethoxy}-undecylcarbamoyl)-ethyldisulfanyl]-propionamide (13)

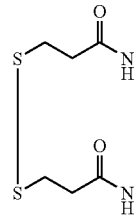 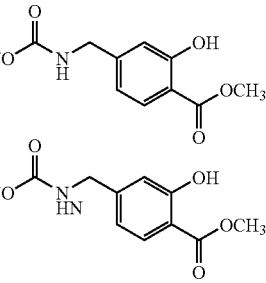

Dithiopropionic acid (1.05 g, 5.0 mmol) was dissolved in anhydrous 1,4-dioxane (20 mL). The solution was stirred and N-hydroxysuccinimide (1.15 g, 10.0 mmol) was added, followed by N,N'-dicyclohexylcarbodiimide (2.06 g, 10.0 mmol). The reaction mixture was stirred for 16 hours at room temperature, then filtered.

In a separate flask, compound 12 (7.68 g, 10.0 mmol) was dissolved in anhydrous 1,4-dioxane (20 mL) and hydrogen chloride in 1,4-dioxane (4 N, 10 mL, 40.0 mmol) was added. The solution was stirred at room temperature for 16 hours. The mixture was then cooled to 4° C., and N,N-diisopropylethylamine (10 mL, 57.0 mmol) was added slowly.

The two reaction mixtures were combined and stirred for 3 hours at room temperature. The solvents were evaporated in vacuo, and the residue was dissolved in dichloromethane. The dichloromethane solution was washed with aqueous hydrochloric acid (1 N, 50 mL), water (100 mL) and brine (50 mL), then dried over anhydrous magnesium sulfate and filtered. The filtrate was evaporated in vacuo, and the product crystallized from ethyl acetate (150 mL) and hexanes (100 mL) to give a white solid (5.60 g, 75% yield). $^1$H NMR (DMSO-d$_6$) δ 10.51 (s, 1H), 7.86 (m, 2H), 7.73 (d, 1H, J=8.7 Hz), 6.84 (s, 1H), 6.82 (d, 1H), J=8.7 Hz), 4.19 (d, 2H, J=6.3 Hz), 4.09 (m, 2H), 3.88 (s, 3H), 3.58 (m, 2H), 3.52–3.40 (m, 20H), 3.36 (t, 2H, J=6.6 Hz), 3.01 (q, 2H, J=6.0 Hz), 2.87 (t, 2H, J =7.2 Hz), 2.46 (t, 2H, J=7.2 Hz), 1.52–1.20 (m, 18H).

D) Synthesis of (3-Hydroxy-4-hydroxycarbamoyl-benzyl)-carbamic acid 2-(2-{2-[2-(2-{2-[11-(3-mercapto-propionylamino)-undecyloxy]-ethoxy}-ethoxy)-ethoxy]-ethoxy}-ethoxy)-ethyl Ester (14)

A solution of sodium methoxide in methanol (0.5 N, 240 mL, 120 mmol) was added to hydroxylamine hydrochloride (5.6 g, 80.4 mmol). The mixture was cooled to 0° C., and stirred for 45 minutes. To the milky suspension was added compound 13 (12.0 g, 8.04 mmol) and the reaction was stirred at room temperature for 30 hours. The mixture was cooled to 0° C., then aqueous hydrochloric acid (6 N, 15 mL) was added and the reaction was stirred a further 10 minutes. Tris-carboxyethylphosphine hydrochloride (2.77 g, 9.65 mmol) was added and the pH of the mixture was adjusted to 5. The solution was stirred at room temperature for 20 hours. Solvents were evaporated in vacuo. The residue was diluted with water (200 mL) and acidified to a pH of about 3 with aqueous hydrochloric acid (1 N). The aqueous solution was extracted three times with ethyl acetate (100 mL portions). The combined organic extracts were washed twice with water (100 mL portions) and then brine (100 mL). The ethyl acetate solution was dried over anhydrous sodium sulfate and filtered. The filtrate was then evaporated in vacuo to give a white solid (10.33 g, 86% yield). $^1$H NMR (300 MHz, DMSO-d$_6$): δ 1.24 (s, 14H), 1.33–1.39 (m, 2H), 1.43–1.48 (m, 2H), 2.23 (t, J=7.9 Hz, 1H), 2.35 (t, J=6.8 Hz, 2H), 2.64 (q, J=7.0 Hz, 2H), 3.02 (q, J=6.3 Hz, 2H), 3.33–3.59 (m, 24H), 4.08 (m, 2H), 4.13 (d, J=6.0 Hz, 2H), 6.73 (d, J=8.2 Hz, 1H), 6.76 (s, 1H), 7.61 (d, J=8.2 Hz, 1H), 7.80 (t, J=6.3 Hz, 1H), 7.83 (t, J=6.3 Hz, 11H), 9.30 (br s, 1H), 11.38 (s, 1H), 12.27 (s, 1H). $^{13}$C NMR (75 MHz, DMSO-d$_6$): δ 20.05, 25.68, 26.42, 28.77, 28.91, 28.99, 29.02, 29.06, 29.14, 29.24, 43.40, 63.39, 68.87, 69.49, 69.81 (large broad), 70.34, 112.31, 115.33, 117.30, 126.90, 145.79, 156.48, 159.56, 166.23, 169.95. HRMS (ESI-pos): calcd for $C_{35}H_{62}N_3O_{12}S$ 748.4054, obsd 748.4061.

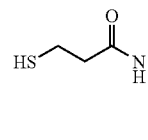 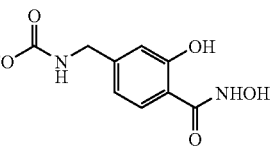

Example 3

Synthesis of N-(11-{2-[2-(2-{2-[2-{2-Hydroxy-ethoxy)-ethoxyl-ethoxy}-ethoxy)-ethoxy]-ethoxy}-undecyl)-3-mercaptopropionamide (15)

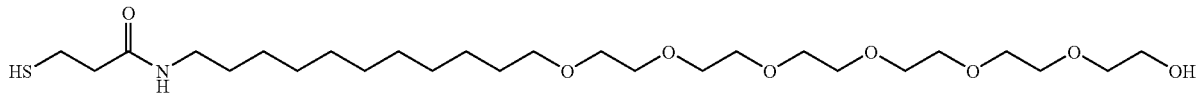

Compound 15 was prepared from compound 11 using methods analogous to the preparation of compound 6 (Example 1, steps E and F). $^1$H NMR (DMSO-$d_6$) δ 7.83 (t, 1H, J=5.5 Hz), 4.58 (t, 1H, J=5.7 Hz), 3.53–3.25 (m, 26H), 3.02 (q, 2H, J=6.3 Hz), 2.63 (m, 2H), 2.35 (t, 2H, J=6.9 Hz), 2.23 (t, 1H, J=7.8 Hz), 1.50–1.20 (m, 18H). $^{13}$C NMR (DMSO-$d_6$) δ 169.90, 72.34, 70.30, 69.78, 69.47, 60.20, 38.43, 29.21, 29.10, 29.02, 28.98, 28.95, 28.88, 28.73, 26.36, 25.65, 20.01. HRMS (ESI-pos) calcd for $C_{26}H_{53}NO_8S$ 539.3492, obsd 539.3486.

Example 4

Synthesis of (3-Hydroxy-4-hydroxycarbamoyl-benzyl)-carbamic acid 2-(2-{2-[2-(2-{2 -[2-(2-{2-[11-(3-mercapto-propionylamino)-undecyloxy}-ethoxy)-ethoxy]-ethoxy}-ethoxy)-ethoxy]-ethoxy}-ethoxyl-ethoxy)-ethyl Ester (18)

A) Synthesis of Methanesulfonic acid 2-{2-[2-(11-tert-butoxycarbonylamino-undecyloxy)-ethoxy]ethoxy}-ethyl ester (16)

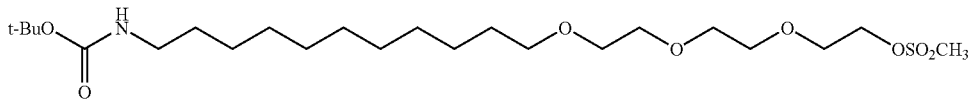

Compound 16 was prepared from compound 4 using methods analogous to the preparation of compound 3 (Example 1, step C). $^1$H NMR (DMSO-$d_6$) δ 6.95 (t, 1H, J=5.5 Hz), 4.50 (m, 2H), 3.86 (m, 2H), 3.75–3.62 (m, 8H), 3.57 (t, 2H, J=7.2 Hz), 3.37 (s, 3H), 3.07 (q, 2H, J=6.0 Hz), 1.70–1.58 (m, 27H).

B) Synthesis of (tert-Butoxy)-N-(1-{2-(2-[2-{2-[2-(2-{2-[2 -hydroxy-ethoxy)-ethoxy]-ethoxy}-ethoxy)-ethoxy]-ethoxy}-ethoxy]-ethoxy)-ethoxy}undecyl)-carbamic acid tert-butyl ester (17)

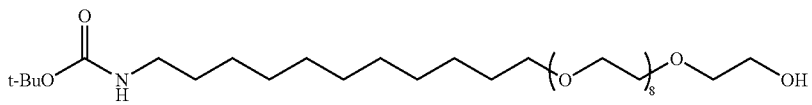

Compound 17 was prepared from compound 16 using methods analogous to the preparation of compound 11 (Example 2, step A). $^1$H NMR (DMSO-$d_6$) δ 6.72 (t, 1H, J=5.0 Hz), 4.58 (t, 1H, J=5.4 Hz), 3.76–3.35 (m, 38H), 2.88 (q, 2H, J=6.6 Hz), 1.52–1.18 (m, 27H). $^{13}$C NMR (DMSO-$d_6$) δ 155.55, 77.20, 72.38, 70.35, 69.83, 69.52, 60.24, 29.50, 29.25, 29.07, 29.05, 28.99, 28.93, 28.77, 28.24, 26.30, 25.68. HRMS (ESI-pos) calcd for $C_{34}H_{69}NO_{12}$ 683.4820, obsd: 683.4829.

C) Synthesis of (3-Hydroxy-4-hydroxycarbamoyl-benzyl)-carbamic acid 2-(2-{2-[2-(2-{2 -[2-(2-{2-[11-(3-mercapto-propionylamino)-undecyloxy}-ethoxy)-ethoxy]-ethoxy}-ethoxy)-ethoxy]-ethoxy}-ethoxy)-ethyl ester (18)

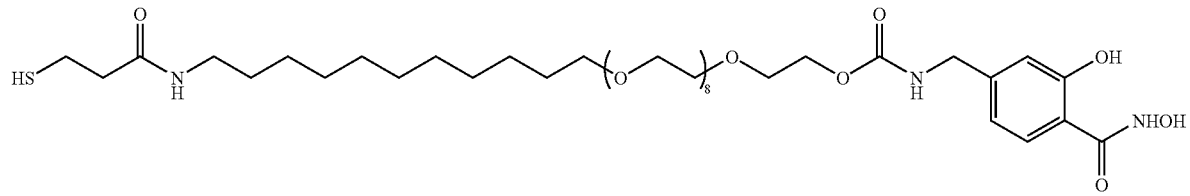

Compound 18 was prepared from compound 17 using methods analogous to the preparation of compound 14 (Example 2, steps B, C and D). $^1$H NMR (DMSO-d$_6$) δ 12.27 (s, 1H), 11.38 (s, 1H), 9.30 (s, 1H), 7.80 (m, 2H), 7.61 (d, 1H,J=8.4 Hz), 6.76 (s, 1H), 6.73 (d, 1H, J=8.4 Hz), 4.13 (d, 2H, J=6.0 Hz), 4.08 (m, 2H), 3.62–3.28 (m, 36H), 3.02 (q, 2H, J=6.6 Hz), 2.65 (q, 2H, J=7.2 Hz), 2.35 (t, 2H, J=6.9 Hz), 2.23 (t, 1H, J=8.1 Hz), 1.52–1.20 (m, 18H). $^{13}$C NMR (DMSO-d$_6$) δ 169.92, 166.29.159.55, 156.46, 145.80, 126.88, 117.28, 115.33, 112.30, 70.31, 69.78, 69.47, 69.84, 63.36, 43.38, 38.44, 29.21, 29.11, 29.03, 28.99, 28.96, 28.88, 28.74, 26.39, 25.65, 20.02. HRMS (ESI-pos) calcd for $C_{41}H_{73}N_3O_{15}S$ 879.4762, obsd: 879.4775.

Example 5

Synthesis of N-(11-{2-[2-(2-Hydroxy-ethoxy)-ethoxyl-ethoxy}-undecyl)-2-mercapto-acetamide (19)

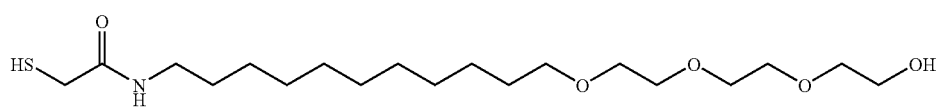

Compound 19 was prepared from compound 4 using methods analogous to the preparation of compound 4 (Example 1, steps E and F), substituting dithiodiglycolic acid for dithiopropionic acid. $^1$H NMR (300 MHz, DMSO-d$_6$): δ 1.24 (br s, 14H), 1.34–1.42 (m, 2H), 1.44–1.52 (m, 2H), 2.67 (t, J=7.9 Hz, 1H), 3.00–3.07 (m, 4H), 3.30–3.50 (m, 14 H), 4.25 (br s, 1H), 7.94 (t, J=5.4 Hz, 1H). $^{13}$C NMR (75 MHz, DMSO-d$_6$): δ 25.65, 26.35, 27.11, 28.74, 28.88, 28.96, 29.03, 29.21, 38.82, 60.21, 69.48, 69.77, 69.80, 69.83, 70.31, 72.34, 169.29. HRMS (ESI-pos): calcd for $C_{19}H_{40}NO_5S$ 394.2627, obsd 394.2628.

Example 6

Synthesis of (3-Hydroxy-4-hydroxycarbamoyl-benzyl)-carbamic acid 2-(2-{2-[2-(2-{2 -[11-(3-mercapto-acetylamino)-undecyloxy]-ethoxy}-ethoxy)-ethoxy]-ethoxy}-ethoxy)-ethyl ester (26)

A) Synthesis of Methyl 2-hydroxy-4-{(benzyloxy)carbonylamino]methyl}benzoate (20)

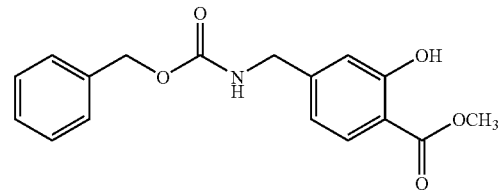

4-Aminomethyl-2-hydroxybenzoic acid methyl ester hydrochloride (21.94 g, 100.8 mmol) was suspended in chloroform (400 mL) and the mixture was stirred while cooling to 0° C. N,N-Diisopropylethylamine (35 mL, 200.9 mmol) was added, followed 5 minutes later by N-(benzyloxycarbonyloxy)succinimide (27.64 g, 110.9 mmol). The cooling bath was removed and the reaction mixture allowed to warm to room temperature. The reaction was then stirred for 1.5 hours at room temperature, then washed sequentially with aqueous hydrochloric acid (1 N, 300 mL), water (200 mL) and brine (150 mL). The organic layer was dried over anhydrous magnesium sulfate, filtered and evaporated in vacuo. The crude product was crystallized from ethyl acetate (100 mL) and hexanes (700 mL), to give a fluffy white solid (24.38 g, 77% yield). $^1$H NMR (300 MHz, DMSO-d$_6$): δ 3.88 (s, 3H), 4.22 (d, J=6.0 Hz, 2H), 5.07 (s, 2H), 6.84 (d, J=8.2 Hz, 1H), 6.87 (s, 1H), 7.28–7.38 (m, 5H), 7.73 (d, J=7.9 Hz, 1H), 7.91 (t, J=6.0 Hz, 1H), 10.53 (s, 1H). $^{13}$C NMR (75 MHz, DMSO-d$_6$): δ 43.52, 52.37, 65.54, 111.36, 115.27, 118.01, 127.77, 127.84, 128.39, 130.05, 137.10, 148.36, 156.46, 160.23, 169.19. HRMS (ESI-pos): calcd for C$_{17}$H$_{17}$NO$_5$Na 338.1004, obsd 338.1003.

B) Synthesis of Methyl 2-(benzyloxy)-4-{(benzyloxy)carbonylamino]methyl}benzoate (21)

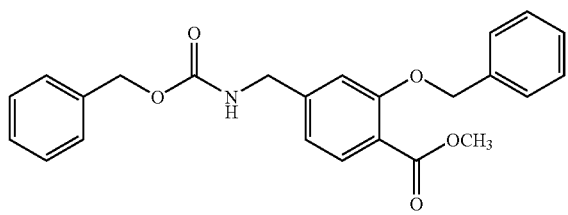

Compound 20 (23.76 g, 75.35 mmol) was dissolved in acetone (250 mL) and anhydrous potassium carbonate (52.0 g, 376.0 mmol) was added, followed by benzyl bromide (18.0 mL, 151.0 mmol). The reaction mixture was heated at reflux for 24 hours. The potassium carbonate was removed by filtration, and the acetone was evaporated in vacuo. The residue was dissolved in ethyl acetate (500 mL), and the organic solution was washed sequentially with aqueous hydrochloric aced (1 N, 250 mL), water (250 mL) and brine (100 mL). The organic layer was dried over anhydrous magnesium sulfate, filtered and evaporated in vacuo. The crude product was crystallized from ethyl acetate (100 mL) and hexanes (600 mL) to give a fluffy white solid (27.11 g, 89%). $^1$H NMR (300 MHz, DMSO-d$_6$): δ 3.79 (s, 3H), 4.25, (d, J=5.7 Hz, 2H), 5.07 (s, 2H), 5.15 (s, 2H), 6.93 (d, J=7.9 Hz, 1H), 7.15 (s, 1H), 7.24–7.51 (m, 10H), 7.67 (d, J=7.6 Hz, 1H), 7.89 (t, J=6.0 Hz, 1H). $^{13}$C NMR (75 MHz, DMSO-d$_6$): δ 43.72, 51.79, 65.50, 69.65, 112.46, 118.70, 118.76, 127.02, 127.67, 127.78, 127.81, 128.37, 128.39, 131.09, 136.81, 137.13, 146.01, 156.42, 157.50, 165.86. HRMS (ESI-pos): calcd for C$_{24}$H$_{23}$NO$_5$Na 428.1474, obsd 428.1465.

C) Synthesis of Methyl 2-(benzyloxy)-4-{(benzyloxy)carbonylamino]methyl}benzoic Acid (22)

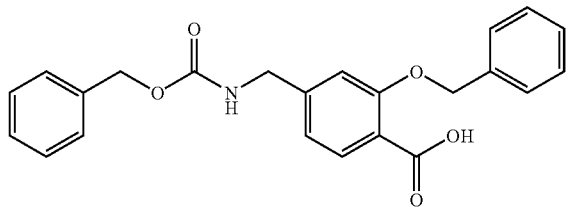

Compound 21 (28.61 g, 66.12 mmol) was dissolved in tetrahydrofuran (250 mL) and the solution was heated to 60° C. Lithium hydroxide monohydrate (3.05 g, 72.7 mmol) dissolved in water (125 mL) was added, and the solution was stirred at 60° C. for 8 hours. The tetrahydrofuran was removed in vacuo, and the resulting suspension was diluted with warm ethyl acetate (400 mL). The layers were separated, and the ethyl acetate solution was sequentially washed twice with aqueous hydrochloric aced (1 N, 200 mL portions), water (200 mL) and brine (100 mL). The organic layer was dried over anhydrous magnesium sulfate, filtered and evaporated in vacuo. The crude product was crystallized from ethyl acetate (350 mL) and hexanes (350 mL) to give a white solid (24.27 g, 94%). $^1$H NMR (300 MHz, DMSO-d$_6$): 4.25 (d, J=6.0 Hz, 2H), 5.07 (s, 2H), 5.15 (s, 2H), 6.92 (d, J=7.9 Hz, =H), 7.13 (s, 1H), 7.29–7.52 (m, 10H), 7.65 (d, J=7.9 Hz, 1H), 7.89 (t, J=6.0 Hz, 1H), 12.59 (s, 1H). $^{13}$C NMR (75 MHz, DMSO-d$_6$): 43.76, 65.51, 69.67,112.36, 118.76, 120.20, 127.20, 127.71, 127.80, 127.86, 128.37, 128.39, 131.03, 136.92, 137.17, 145.37, 156.44, 157.31, 167.18. HRMS (ESI-pos): calcd for C$_{23}$H$_{21}$NO$_5$Na 414.1317, obsd 414.1318.

D) Synthesis of N-(tert-Butoxy)-2-(benzyloxy)-4-{(benzyloxy)carbonylamino]methyl}phenyl)-carboxamide (23)

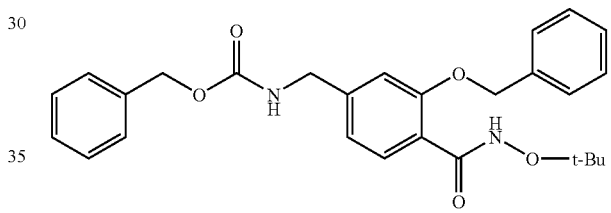

Compound 22 (12.44 g, 31.78 mmol) was dissolved in acetonitrile (250 mL) and N,N-diisopropylethylamine (28.0 mL, 161 mmol) was added. The solution was cooled to 0° C., and isobutyl chloroformate (4.30 mL, 33.2 mL) was added with stirring. The reaction mixture was stirred at 0° C. for 30 minutes, then at room temperature for 1 hour. The solvent was evaporated in vacuo, and the residue was dissolved in ethyl acetate (300 mL). The ethyl acetate solution was washed sequentially with aqueous hydrochloric acid (1 N, 250 mL), water (200 mL) and brine (100 mL). The organic layer was dried over anhydrous magnesium sulfate, filtered and evaporated in vacuo. The crude product was purified by chromatography on silica gel (200 g, gradient of 30% to 50% [v/v] ethyl acetate in hexanes). The product containing fractions were pooled and evaporated in vacuo to give a white foam (14.02 g, 97% yield). $^1$H NMR (300 MHz, DMSO-d$_6$): δ 1.08 (s, 9H), 4.24 (d, J=6.0 Hz, 2H), 5.07 (s, 2H), 5.11 (s, 2H), 6.94 (d, J=7.9 Hz, 1H), 7.13 (s, 1H), 7.27–7.43 (m, 8H), 7.47 –7.51 (m, 3H), 7.90 (t, J=6.0 Hz, 1H), 10.36 (s, 1H). $^{13}$C NMR (75 MHz, DMSO-d$_6$): δ 26.18, 43.73, 65.45, 70.06, 80.87, 111.41, 119.02, 121.90, 127.77, 127.80, 128.14, 128.26, 128.36, 128.43, 129.77, 136.27, 137.16, 143.97, 155.75, 156.37, 164.21.. HRMS (ESI-pos): calcd for C$_{27}$H$_{31}$N$_2$O$_5$ 463.2233, obsd 463.2230.

E) Synthesis of (tert-Butoxy)-N-{11-[2-(2-{2-[2-(2-{2-[N-[{4-[N-(tert-butoxy)carbamoyl]-3-hydroxyphenyl}-methyl)carbamoyloxy]ethoxy}ethoxy)ethoxy]ethoxy}ethoxy)ethoxy]undecyl}-carboxamide (24)

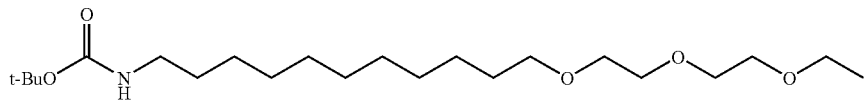

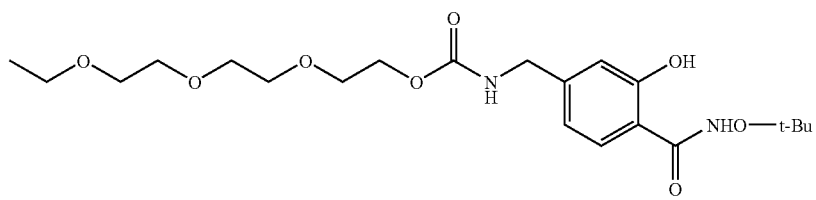

Compound 11 (6.29 g, 11.4 mmol) was dissolved in N,N-dimethylformamide (60 mL) and 1,1'-carbonyldiimidazole (2.03 g, 12.5 mmol) was added. The reaction mixture was stirred for 3.5 hours at room temperature.

At the same time, a hydrogenation bottle (1 L) was charged with compound 23 (6.20 g, 12.7 mmol) dissolved in methanol (300 mL). The atmosphere in the bottle was replaced with nitrogen, and palladium on carbon (10% [w/w], 0.62 g) is added. The bottle was affixed to a Parr hydrogenation apparatus, the bottle evacuated then re-filled with hydrogen to 40 psi, and the reaction was shaken at room temperature for 2 hours. The bottle was then removed from the Parr apparatus, the catalyst removed by filtration, and the methanol evaporated in vacuo. The residue was dissolved in N,N-dimethylformamide (20 mL) and transferred to the reaction flask containing activated compound 11. N,N-Diisopropylethylamine (4.0 mL, 23.0 mmol) was added, and the solution was heated to 70° C. The reaction was allowed to proceed for 24 hours. The solvent was then removed in vacuo, and the residue was dissolved in ethyl acetate (250 mL). The ethyl acetate solution was washed sequentially with aqueous hydrochloric acid (1 N, 150 mL), water (100 mL) and brine (100 mL). The organic layer was dried over anhydrous magnesium sulfate, filtered, and the filtrate was evaporated in vacuo. The crude product was purified by chromatography on silica gel (200 g, gradient of dichloromethane to 5% [v/v] methanol in dichloromethane). The product containing fractions were pooled and evaporated in vacuo to give an oil (5.80 g, 62% yield). $^1$H NMR (300 MHz, DMSO-$d_6$): δ 1.24 (s, 18H), 1.36 (s, 14H), 1.42–1.49 (m, 4H), 2.87 (q, J=6.9 Hz, 2H), 3.35–3.59 (m, 24H), 4.08 (m, 2H), 4.13 (d, J=6.3 Hz, 2H), 6.72–6.78 (m, 3H), 7.66 (d, J=7.9 Hz, 1H), 7.82 (t, J=6.2 Hz, 1H), 11.03 (br s, 1H), 11.86 (br s, 1H). $^{13}$CNMR (75 MHz, DMSO-$d_6$): δ 25.68, 26.30, 26.41, 28.27, 28.76, 28.92, 28.98, 29.01, 29.06, 29.24, 29.50, 43.43, 48.62, 63.39, 68.88, 69.50, 69.82 (large broad), 70.34, 77.26, 81.45, 113.15, 115.24, 117.41, 127.89, 145.94, 155.59, 156.46, 159.04, 167.63. HRMS (ESI-pos): calcd for $C_{41}H_{74}N_3O_{13}$ 816.5222, obsd 816.5217.

F) Synthesis of N-(11-{2-[2-(2-{2-[2-(2-{N-[(4-({N-tert-butoxy}carbamoyl)-3-hydroxyphenyl)methyl]carbamoyloxy}ethoxy)ethoxy]ethoxy}ethoxy)ethoxy]ethoxy}undecyl)-3-({2-[N-(11-{2-[2-(2-{2-[2-(2-{N-[(4-({N-tert-butoxy}carbamoyl)-3-hydroxyphenyl)methyl]-carbamoyloxy}ethoxy)ethoxy]ethoxy}ethoxy)ethoxy]ethoxy}undecyl)carbamoyl]disulfanyl)-acetamide (25)

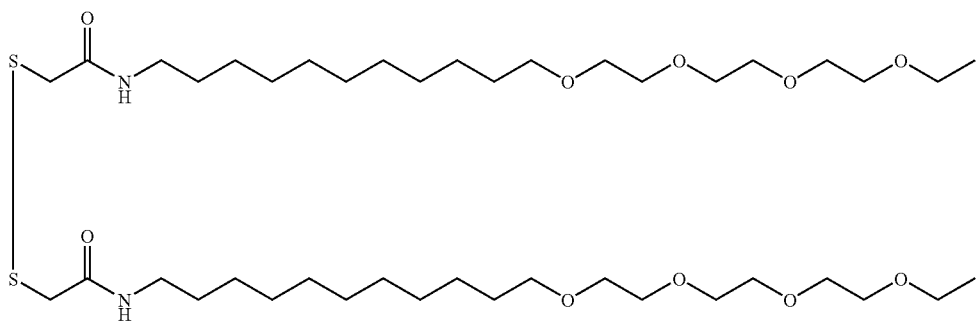

-continued

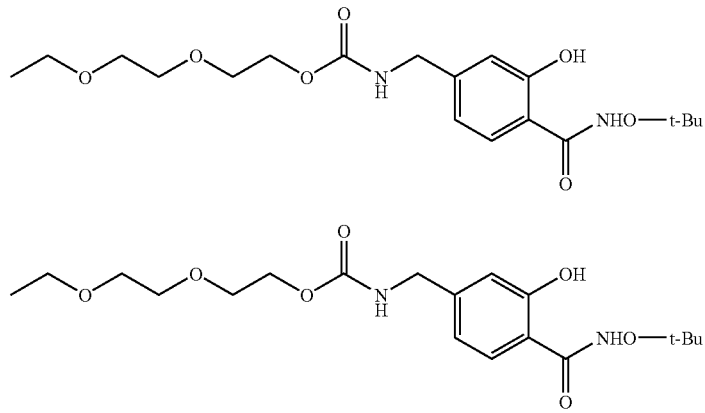

Dithioglycolic acid (0.65 g, 3.54 mmol) was dissolved in tetrahydrofuran (50 mL). The solution was stirred and N-hydroxysuccinimide (0.90 g, 7.79 mmol) was added, followed by N,N'-dicyclohexylcarbodiimide (1.61 g, 7.79 mmol). The reaction mixture was stirred for 16 hours at room temperature, then filtered.

In a separate flask, compound 24 (5.78 g, 7.08 mmol) was dissolved in dichloromethane (25 mL) and trifluoroacetic acid (25 mL) was added. The solution was stirred for 30 minutes at room temperature, and then the solvents were evaporated in vacuo. The resulting oil was dissolved in tetrahydrofuran (50 mL) and N,N-diisopropylethylamine (12.0 mL, 68.9 mmol) was added.

The two reaction mixtures were then combined and stirred for 3 hours at room temperature. The tetrahydrofuran was evaporated in vacuo, and the residue was dissolved in ethyl acetate (300 mL). The ethyl acetate solution was washed sequentially with aqueous hydrochloric acid (1 N, 150 mL), water (100 mL) and brine (100 mL). The organic layer was dried over anhydrous magnesium sulfate, filtered, and the filtrate was evaporated in vacuo. This crude product was used without further purification in the next step. G) Synthesis of (3-Hydroxy-4-hydroxycarbamoyl-benzyl)-carbamic acid 2-(2-{2-[2-(2-{2-[11-(3-mercapto-acetylamino)-undecyloxy]-ethoxy}-ethoxy)-ethoxy]-ethoxy}-ethoxy)-ethyl Ester (26)

The crude compound 25 (3.54 mmol) was dissolved in trifluoroacetic acid (50 mL) and the solution was stirred for 3 days at room temperature. The solvent was then removed in vacuo. The resulting oil was dissolved in methanol (100 mL) and water (10 mL). Tris-carboxyethylphosphine hydrochloride (1.15 g, 4.01 mmol) was added, and the solution was stirred for 2 hours at room temperature. The methanol was removed in vacuo, and ethyl acetate (300 mL) was added. The mixture was washed three times with water (100 mL). The organic layer was dried over anhydrous magnesium sulfate, filtered, and evaporated in vacuo. The crude product was purified by reverse phase HPLC on a Waters Prep LC 2000 preparative chromatography system (Bondapak C18 column, 300 A, 47 mm×300 mm; eluting with 60:40 [v/v] water:methanol containing 0.1% [v/v] trifluoroacetic acid). The product containing fractions were pooled and evaporated in vacuo to give a white solid (0.91 g, 35% yield). $^{1}$H NMR (300 MHz, DMSO-$d_6$): δ 1.24 (s, 14H), 1.33–1.39 (m, 2H), 1.43–1.48 (m, 2H), 2.70 (t, J=7.9 Hz, 1H), 3.03 (q, J=6.3 Hz, 2H), 3.06 (d, J=7.9 Hz, 2H), 3.33–3.59 (m, 24H), 4.08 (m, 2H), 4.13 (d, J=6.0 Hz, 2H), 6.73 (d, J=8.2 Hz, 1H), 6.76 (s, 1H), 7.61 (d, J=8.2 Hz, 1H), 7.80 (t, J=6.3 Hz, 1H), 7.94 (t, J=6.3 Hz, 1H), 9.30 (br s, 1H), 11.38 (s, 1H), 12.27 (s, 1H). $^{13}$C NMR (75 MHz, DMSO-$d_6$): δ 26.54, 27.24, 28.02, 29.62, 29.77, 29.85, 29.89, 29.91, 30.10, 44.28, 64.26, 69.74, 70.36, 70.68 (large broad), 71.21, 113.21, 116.22, 118.17, 127.78, 146.68, 157.35, 160.44, 167.19, 170.20.

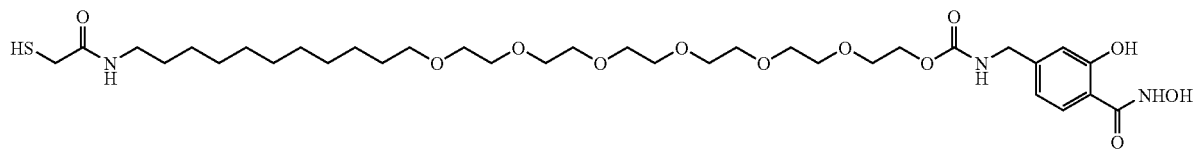

Example 7

Synthesis of 12-{2-[2-(2-Hydroxy-ethoxy)-ethoxy]-ethoxy}-dodecanoic acid (2-mercapto-ethyl)-amide (32)

A) Synthesis of 12-{2-[2-(2-Hydroxy-ethoxy)-ethoxy]-ethoxy}-dodecanoic acid (27)

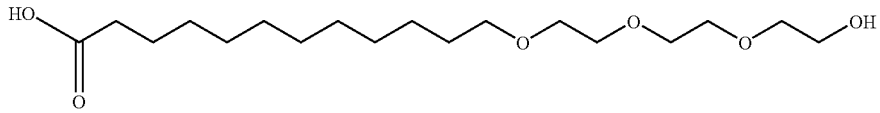

Tri(ethylene glycol) (96.0 mL, 719.0 mmol) was added to a round bottom flask (250 mL) and heated to 110° C. Aqueous sodium hydroxide solution (50% [w/v], 5.75 mL, 71.9 mmol) was added, and the solution was stirred for 45 minutes at 110° C. 12-Bromoundecanoic acid (10.0 g, 35.8 mmol) was added to the hot solution, and stirring was continued for 16 hours at 110° C. The reaction mixture was then cooled to room temperature, and diluted with water (500 mL). The aqueous solution was extracted three times with ethyl acetate (150 mL portions). The combined ethyl acetate extracts were dried over anhydrous magnesium sulfate, filtered and evaporated in vacuo. The crude product was purified by chromatography on silica gel (200 g, gradient of dichloromethane to 5% [v/v] methanol in dichloromethane). The product containing fractions were pooled and evaporated in vacuo to give a white solid (9.82 g, 81% yield). $^1$H NMR (300 MHz, DMSO-$d_6$): δ 1.24 (br s, 14H), 1.47 (m, 4H), 2.17 (t, J=7.3 Hz, 2H), 3.33–3.50 (m, 14H), 4.56 (br s, 1H), 11.96 (br s, 1H). $^{13}$C NMR (75 MHz, DMSO-$d_6$): δ 24.50, 25.66, 28.56, 28.76, 28.89, 28.92, 28.97, 29.03, 29.21, 33.66, 60.22, 69.49, 69.78, 69.81, 69.85, 70.32, 72.36, 174.47. HRMS (ESI-pos): calcd for $C_{18}H_{36}O_6Na$ 371.2410, obsd 371.2416.

B) Synthesis of 12-(2-{2-[2-(2,2-dimethyl-1,1-diphenyl-1-silapropoxy)-ethoxy]-ethoxy}-ethoxy)-dodecanoic acid 2,2-dimethyl-1,1-dipehnyl-1-silapropyl ester (28)

Compound 27 (4.75 g, 13.6 mmol) was dissolved in N,N-dimethylformamide (60 mL). Imidazole (3.72 g, 54.6 mmol) was added to the stirred solution, followed by tert-butylchlorodiphenylsilane (8.90 mL, 34.2 mmol). The reaction was stirred at room temperature for 16 hours. The reaction mixture was then diluted with ethyl acetate (500 mL) and washed twice with water (150 mL portions) and then brine (100 mL). The organic layer was dried over anhydrous magnesium sulfate, filtered, and the solvents were evaporated in vacuo. The crude product was used without further purification in the next step.

C) Synthesis of 12-(2-{2-[2-(2,2-dimethyl-1,1-diphenyl-1-silapropoxy)-ethoxy]-ethoxy}-ethoxy)-dodecanoic Acid (29)

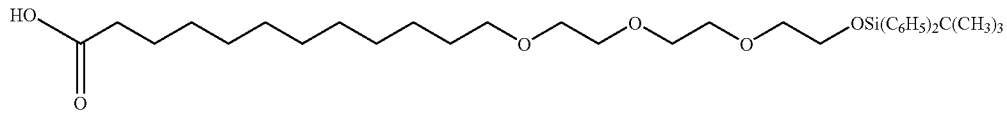

Crude compound 28 (13.6 mmol) was dissolved in methanol (350 mL). Potassium carbonate (1.89 g, 13.7 mmol), dissolved in water (30 mL), was added dropwise over 15 minutes. The reaction was stirred an additional hour at room temperature, then the methanol was evaporated in vacuo. The residue was dissolved in ethyl acetate (300 mL), then washed twice with water (100 mL portions) and then brine (75 mL). The organic layer was dried over anhydrous magnesium sulfate, filtered, and the filtrate was evaporated in vacuo. The crude product was purified by chromatography on silica gel (150 g, gradient of ethyl acetate:hexanes, 20:80 [v/v] to 60:40 [v/v]). The product containing fractions were pooled and evaporated in vacuo to give an oil (3.38 g, 42% yield). $^1$H NMR (300 MHz, DMSO-$d_6$): δ 0.98 (s, 9H), 1.20 (br s, 14H), 1.40–1.49 (m, 4H), 2.16 (t, J=7.5 Hz, 2H), 3.33 (t, J=6.5 Hz, 2H), 3.41–3.44 (m, 2H), 3.49–3.54 (m, 8H), 3.72–3.75 (m, 2H), 7.36–7.46 (m, 6H), 7.63-7.67 (m, 4H), 11.97 (s, 1H). $^{13}$C NMR (75 MHz, DMSO-$d_6$): δ 18.74, 24.49, 25.63, 26.58, 28.56, 28.75, 28.86, 28.90, 28.95, 29.00, 29.21, 33.65, 63.25, 69.52, 69.90, 70.04,

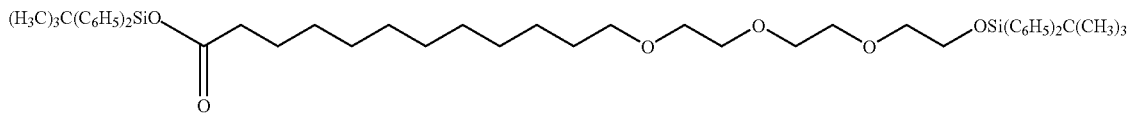

70.30, 71.64, 127.76, 129.72, 133.11, 135.08, 174.43. HRMS (ESI-pos): calcd for $C_{34}H_{54}O_6NaSi$ 609.3587, obsd 609.3586.

D) Synthesis of 12-(2-{2-[2-(2,2-Dimethyl-1,1-diphenyl-1-silapropoxy)-ethoxy]-ethoxy}-ethoxy)-N-[2-({2-[12-(2-{2-[2-(2,2-dimethyl-1,1-diphenyl-1-silapropoxy)-ethoxy]-ethoxy}-ethoxy)-dodecanoylamino]-ethyl}-disulfanyl)-ethyl]-dodecanamide (30)

1.39–1.52 (m, 8H), 2.05 (t, J=7.3 Hz, 4H), 2.75 (t, J=6.8 Hz, 4H), 3.29–3.35 (m, 10H), 3.41–3.44 (m, 4H), 3.48–3.53 (m, 14H), 3.73 (t, J=4.9 Hz, 4H), 7.37–7.45 (m, 12H), 7.62–7.65 (m, 8H), 7.97 (t, J=5.6 Hz, 2H). $^{13}C$ NMR (75 MHz, DMSO-$d_6$): δ 18.73, 25.22, 25.64, 26.57, 28.66, 28.80, 28.88, 28.94, 28.99, 29.02, 29.21, 35.33, 37.39, 37.85, 63.25, 69.52, 69.89, 70.04, 70.30, 71.63, 127.75, 129.71,

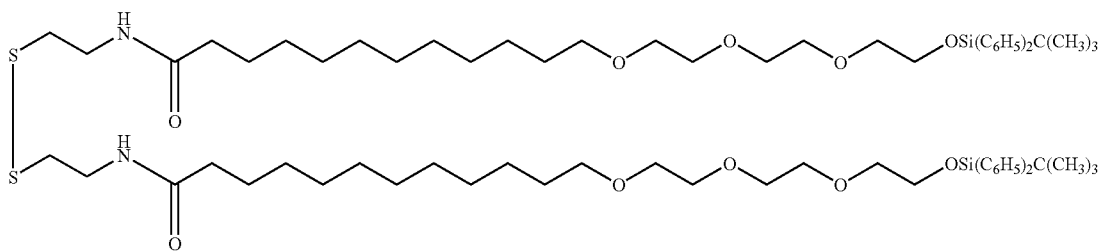

30

Compound 29 (3.30 g, 5.61 mmol) was dissolved in N,N-dimethylformamide (50 mL) and N-hydroxysuccinimide (0.74 g, 6.39 mmol) was added, followed by N,N'-dicyclohexylcarbodiimide (1.31 g, 6.35 mmol). The reaction was stirred at room temperature for 24 hours. N,N-Diisopropyethylamine (5.00 mL, 28.7 mmol) and cystamine dihydrochloride (670 mg, 2.98 mmol) were added, and stirring was continued for 6 hours. The reaction mixture was diluted with ethyl acetate (300 mL) and washed twice with water (150 mL portions) and then brine (75 mL). The organic layer was dried over anhydrous magnesium sulfate, filtered, and evaporated in vacuo. The crude product was purified by chromatography on silica gel (150 g, gradient of dichloromethane to 3% [v/v] methanol in dichloromethane). The product containing fractions were pooled and evaporated in vacuo to give an oil (2.73 g, 75% yield). $^1H$ NMR (300 MHz, DMSO-$d_6$): δ 0.97 (s, 18H), 1.19 (br s, 28H), 133.10, 135.07, 172.27. HRMS (ESI-pos): calcd for $C_{72}H_{16}N_2O_{10}NaSi_2S_2$ 1311.7508, obsd 1311.7471.

E) Synthesis of 12-(2-{2-[2-Hydroxy-ethoxy]-ethoxy}-ethoxy)-N-[2-({2-[12-(2-{2-[2-hydroxy-ethoxy]-ethoxy}-ethoxy)-dodecanoylamino]-ethyl}-disulfanyl)-ethyl]-dodecanamide (31)

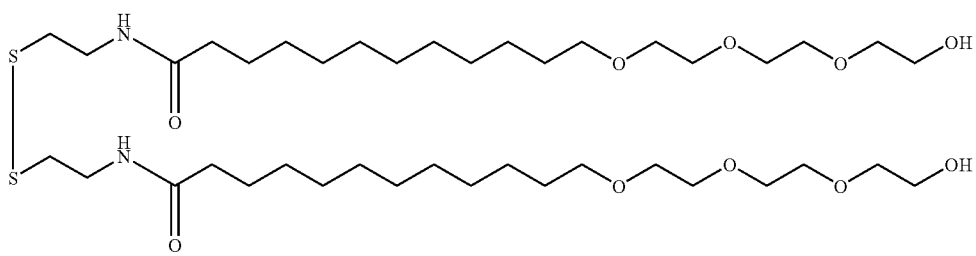

Compound 30 (1.76 g, 1.40 mmol) was dissolved in tetrahydrofuran (50 mL) and terabutylammonium fluoride in tetrahydrofuran (1.0 M, 2.95 mL) was added. The solution was stirred at room temperature for 2 hours. The solvent was evaporated in vacuo. The resulting oil was dissolved in dichloromethane (200 mL) and the solution was washed with aqueous hydrochloric acid (1 N, 100 mL), water (75 mL) and brine (75 mL). The organic layer was dried over anhydrous magnesium sulfate, filtered and evaporated in vacuo. The crude product was used in the next step without further purification.

F) Synthesis of 12-{2-[2-(2-Hydroxy-ethoxy)-ethoxy]-ethoxy}-dodecanoic acid (2-mercapto-ethyl)-amide (32)

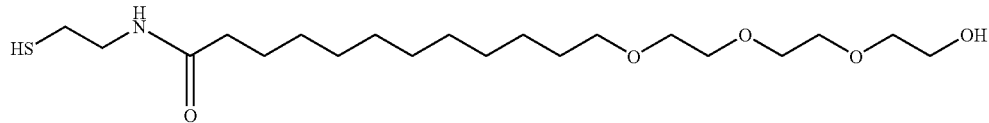

Crude compound 31 (1.40 mmol) was dissolved in methanol (50 mL) and water (10 mL). Tris-carboxyethylphosphine hydrochloride (0.80 g, 2.79 mmol) was added, and the solution was stirred for 24 hours at room temperature. The methanol was removed in vacuo, and dichloromethane (150 mL) was added. The mixture was washed with water (75 mL). The organic layer was dried over anhydrous magnesium sulfate, filtered, and evaporated in vacuo. The crude product was purified by chromatography on silica gel (100 g, gradient of dichloromethane to 3% [v/v] methanol in dichloromethane). The product containing fractions were pooled and evaporated in vacuo to give a white solid (0.92 g, 81% yield). $^1$H NMR (300 MHz, DMSO-d$_6$): δ 1.23 (br s, 14H), 1.46 (m, 4H), 2.04 (t, J=7.3 Hz, 2H), 2.29 (t, J=7.6 Hz, 1H), 2.49 (q, J=7.6 Hz, 2H), 3.17 (q, J=6.7 Hz, 2H), 3.35–3.51 (m, 14H), 4.5 (br s, 1H), 7.92 (t, J=5.4 Hz, 1H). $^{13}$C NMR (75 MHz, DMSO-d$_6$): δ 23.54, 25.25, 25,66 28.66, 28.79, 28.90, 28.95, 28.99, 29.04, 29.22, 35.34, 42.03, 60.22, 69.49, 69.78, 69.81, 69.85, 70.33, 72.36, 172.18. HRMS (ESI-pos): calcd for $C_{20}H_{41}NO_5NaS$ 430.2603, obsd 430.2601.

Example 8

Synthesis of 2-{2-[2-(2-{2-[2-(11-Mercapto-undecyloxy)-ethoxy]-ethoxy}-ethoxy)-ethoxy]-ethoxy}-ethanol (33)

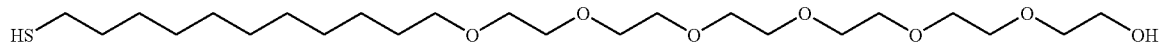

Compound 33 was prepared by the method of Pale-Grosdemange et al. (Pale-Grosdemange, C., Simon, E. S., Prime, K. L. and Whitesides, G. M. (1991) *J. Am. Chem. Soc.* 113, 12–20).

Example 9

General Procedure for Preparation of Unitary Self-Assembled Monolayer Matrix

Six-inch diameter circular glass wafers (thickness 0.3 mm) coated with a film of metallic gold (thickness 50 nm; metallic titanium adhesion layer, thickness 1–2 nm; films deposited in one vacuum cycle using an e-beam evaporator) were obtained from Texas Instruments, Inc.; Dallas, Tex., USA). The gold film on the wafer was cleaned by treatment with ozone and ultraviolet light in a PR-100 UV-Ozone Photoreactor (UVP; Upland, Calif., USA) for 45 minutes, followed immediately by soaking in a bath of absolute ethanol for 20 minutes (to reduce gold oxides formed during the cleaning process). The cleaned wafer was used immediately for SAM deposition.

A solution of thiol compound was prepared at a total thiol concentration of 1.0 mM in absolute ethanol. A cleaned wafer was placed gold-side up in a polypropylene tub of sufficient diameter to allow the wafer to sit horizontally at the bottom. The thiol solution was added (150 to 200 mL) and the tub was covered. The wafer was allowed to sit in the thiol solution for 5 days in the dark. The wafer was then removed from the solution and washed in a vigorous spray of absolute ethanol or N,N-dimethylformamide. Alternatively, the wafer was sonicated in a covered polypropylene container in three changes of either absolute ethanol or N,N-dimethylformamide for 15 minutes each. Finally, the wafer was washed with absolute ethanol and dried under a stream of nitrogen.

Alternatively, the wafer was sawed or scribed into small chips (9.46 mm×4.46 mm) prior to deposition of the mixed SAM. The procedure used for cleaning the chips and depositing the mixed SAM was the same as that for the wafer.

Example 10

General One-Step Procedure for Preparation of Mixed Self-Assembled Monolayer Matrix Six-inch diameter circular glass wafers (thickness 0.3 mm) coated with a film of metallic gold (thickness 50 nm; metallic titanium adhesion layer, thickness 1–2 nm; films deposited in one vacuum cycle using an e-beam evaporator) were obtained from Texas Instruments, Inc.; Dallas, Tex., USA). The gold film on the wafer was cleaned by treatment with ozone and ultraviolet light in a PR-100 UV-Ozone Photoreactor (UVP; Upland, Calif., USA) for 45 minutes, followed immediately by soaking in a bath of absolute ethanol for 20 minutes (to reduce gold oxides formed during the cleaning process). The cleaned wafer was used immediately for SAM deposition.

A solution of thiol compound containing the boronic acid complexing moiety (e.g., compounds of Formulae IIa and IIb such as compound 14, compound 18 and compound 26) and thiol terminating in an uncharged, hydrophilic group (e.g., compounds of Formula VIa and VIb, such as compound 4 and compound 32) in the desired molar ratio was prepared at a total thiol concentration of 1.0 mM in absolute ethanol. A cleaned wafer was placed gold-side up in a polypropylene tub of sufficient diameter to allow the wafer to sit horizontally at the bottom. The mixed thiol solution was added (150 to 200 mL) and the tub was covered. The wafer was allowed to sit in the thiol solution for 5 days in the dark. The wafer was then removed from the solution and washed in a vigorous spray of absolute ethanol or N,N-dimethylformamide. Alternatively, the wafer was sonicated in a covered polypropylene container in three changes of either absolute ethanol or N,N-dimethylformamide for 15 minutes each. Finally, the wafer was washed with absolute ethanol and dried under a stream of nitrogen.

Alternatively, the wafer was sawed or scribed into small chips (9.46 mm×4.46 mm) prior to deposition of the mixed SAM. The procedure used for cleaning the chips and depositing the mixed SAM was the same as that for the wafer.

Example 11

General Two-Step Procedure for Preparation of Mixed Self-Assembled Monolayer Matrix Six-inch diameter circular glass wafers (thickness 0.3 mm) coated with a film of metallic gold (thickness 50 nm; metallic titanium adhesion layer, thickness 1–2 nm; films deposited in one vacuum cycle using an e-beam evaporator) were obtained from Texas Instruments, Inc.; Dallas, Tex., USA). The gold film on the wafer was cleaned by treatment with ozone and ultraviolet light in a PR-100 UV-Ozone Photoreactor (UVP; Upland, Calif., USA) for 45 minutes, followed immediately by soaking in a bath of absolute ethanol for 20 minutes (to reduce gold oxides formed during the cleaning process). Finally, the wafer was rinsed twice with 10:90 [v/v] water:N,N-dimethylformamide (mL). The cleaned wafer was used immediately for SAM deposition.

A solution of thiol compound containing the boronic acid complexing moiety (e.g., compounds of Formulae IIa and IIb such as compound 14, compound 18 and compound 26) was prepared at the desired concentration ("X mM") in 10:90 [v/v] water:N,N-dimethylformamide. A cleaned wafer was placed gold-side up in a polypropylene tub of sufficient diameter to allow the wafer to sit horizontally at the bottom. The thiol solution was added (150 to 200 mL) and the tub was covered. The wafer was allowed to sit in the thiol solution for 15–24 hours in the dark. The wafer was then removed from the solution and rinsed twice with 10:90 [v/v] water:N,N-dimethylformamide. A solution of the thiol compound terminating in an uncharged, hydrophilic group (e.g., compounds of Formula VIa and VIb, such as compound 4 and compound 32) in the desired concentration ("1.0-X mM") was prepared in 10:90 [v/v] water:N,N-dimethylformamide. The once-treated wafer was placed gold-side up in a polypropylene tub of sufficient diameter to allow the wafer to sit horizontally at the bottom. The second thiol solution was added (150 to 200 mL) and the tub was covered. The wafer was allowed to sit in the thiol solution for 2–5 days in the dark. The wafer was then removed from the solution and sonicated in a covered polypropylene container in three changes of N,N-dimethylformamide for 15 minutes each. Finally, the wafer was washed with absolute ethanol and dried under a stream of nitrogen.

Alternatively, the wafer was sawed or scribed into small chips (9.46 mm×4.46 mm) prior to deposition of the mixed SAM. The procedure used for cleaning the chips and depositing the mixed SAM was the same as that for the wafer.

Example 12

Comparison of Thermal Stability of Self-Assembled Monolayers Comprised of Monomers Containing Amide Groups with Self-Assembled Monolayers Comprised of Monomers Lacking Amide Groups The following procedure for measuring the thermal stability of self-assembled monolayers (SAMs) was adapted from Shon, Y.-S. and Lee, T. R. (2000) *J. Phys. Chem. B* 104, 8192–8200.

Figure 5:
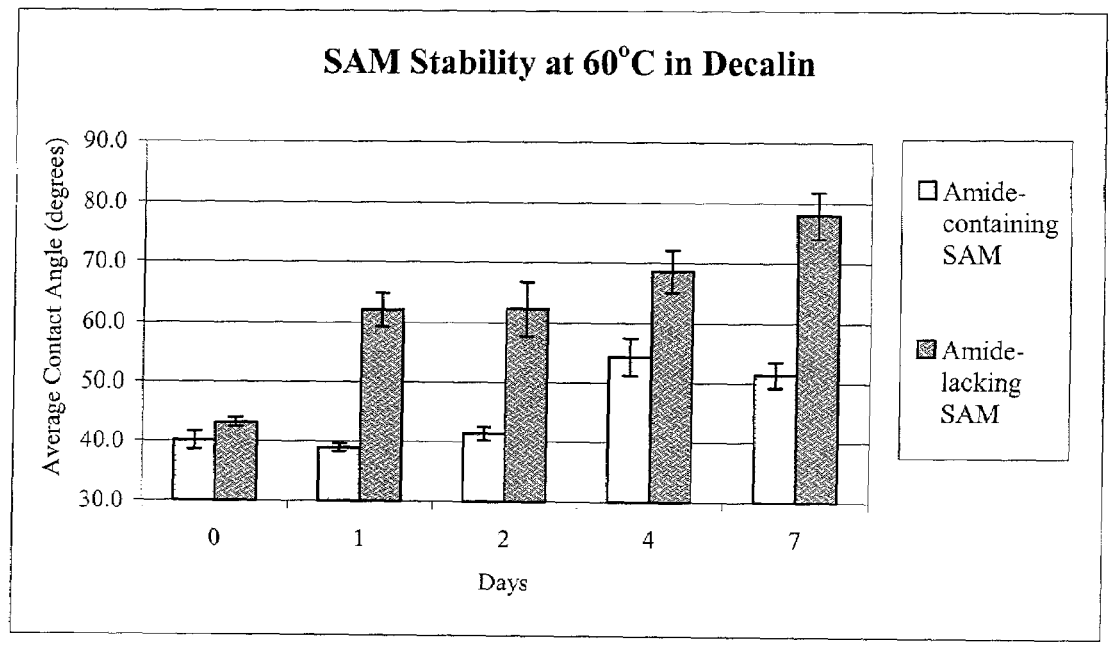
FIG. 5 presents a summary of contact angle data obtained in Example 12.

SAMs were prepared on gold-on-glass chips (mm×mm) according to the procedure of Example 9 using a 1.0 mM solution of either compound 15 (amide-containing; 25 chips) or compound 33 (amide-lacking; 25 chips) in absolute ethanol. Following SAM deposition, the chips were gently wiped with a non-abrasive, lint-free pad moistened with aqueous sodium hydroxide (1 N), then rinsed well with water. The SAM-coated chips were then air-dried. The cleaned, coated chips (5 of each type) were then analyzed for surface wettability using water contact angle measurements obtained with a VCA Optima (AST Products, Inc.; Billerica, Mass., USA). The remaining chips (20 of each type) were individually placed in 2 mL polypropylene microcentrifuge tubes containing 1.5 mL of decalin (decahydronaphthalene). The tubes were then immersed in a water bath at 60° C. Chips were removed from water bath after 1, 2, 4 or 7 (5 chips each) days, rinsed well with 2-propanol and air-dried. The chips were then analyzed for surface wettability using water contact angle measurements. Water contact angles were determined under ambient conditions using standard and well-known procedures. The data is presented below in Table I and summarized in FIG. 5.

TABLE I

|  | Amide-containing SAM (water contact angle, degrees) | | | | | Amide-lacking SAM (water contact angle, degrees) | | | | |
| --- | --- | --- | --- | --- | --- | --- | --- | --- | --- | --- |
|  | 0 day | 1 day | 2 days | 4 days | 7 days | 0 day | 1 day | 2 days | 4 days | 7 days |
|  | 37.8 | 40.0 | 39.7 | 55.4 | 49.2 | 43.4 | 61.8 | 62.5 | 66.7 | 81.9 |
|  | 39.7 | 38.6 | 41.2 | 53.4 | 54.1 | 42.5 | 59.3 | 68.3 | 71.8 | 76.8 |
|  | 40.8 | 38.8 | 42.2 | 59.0 | 51.7 | 42.6 | 66.1 | 62.8 | 72.0 | 79.7 |
|  | 42.5 | 38.3 | 41.3 | 50.4 | 52.7 | 44.4 | 63.1 | 55.8 | 68.4 | 79.8 |
|  | 39.7 | 38.8 | 42.5 | 53.5 | 49.3 | 43.1 | 59.8 | 61.6 | 63.7 | 71.8 |
| Average | 40.1 | 38.9 | 41.4 | 54.3 | 51.4 | 43.1 | 62.0 | 62.2 | 68.5 | 78.0 |
| Std. Dev. | 1.5 | 0.6 | 1.1 | 3.2 | 2.1 | 0.7 | 2.7 | 4.4 | 3.5 | 3.9 |

Water contact angle is an indicator of the wettability of surface. Smaller values of water contact angle indicate a more wettable (i.e., hydrophilic) surface, while larger values indicate a less wettable (i.e., hydrophobic) surface. Intitially, chips with SAMs prepared from either the amide-containing monomer or amide-lacking monomer showed good wettability (contact angle of 40–43 degrees), consistent with the surface presentation of hydrophilic oligo(ethylene glycol) groups (see FIG. 1). However, significant differences were observed between the two SAMs on heating to 60° C. The amide-containing SAMs showed little change in wettablity until between 2 and 4 days of incubation at elevated temperature, and even modest wettablity after 4 days (contact angle of 51–54 degrees), indicating fill to partial retention of the hydrophilic SAM layer. Conversely, the amide-lacking SAMs showed poor wettability (contact angle of 62 degrees) within 1 day of treatment at elevated temperature, indicating significant if not total loss of the hydrophilic SAM layer. As a calibration, the pure gold film (no SAM) exhibited a water contact angle of greater than 60 degrees.

It can be concluded that the amide-containing SAMs (unitary or mixed) that are the subject of the present invention have a significant advantage over amide-lacking SAMs in terms of their stability at elevated temperature. This is presumably due to the ability of the amide-containing SAM monomers to form a strong network of hydrogen bonds among the various amide groups near the surface of the gold film, stabilizing the SAM toward thermal degradation (loss of SAM due to cleavage of the gold-sulfur bond). Formation of such a network of hydrogen bonds is not possible in the prior art amide-lacking SAMs.

Example 13

Preparation of the Spreeta 2000 Sensor

Spreeta 2000 sensors without the gold-on-glass sensing surface were obtained from Texas Instruments. Gold-on-glass chips (9.46 mm×4.46 mm), coated with a matrix of the present invention (unitary or mixed SAM), were prepared as described in Examples 9, 10 and 11 above.

The gold-on-glass chips with the immobilization matrix were affixed to the Spreeta 2000 sensors using optical epoxy (OS 1102; Dexter Corporation; Olean, N.Y., USA). Resin (100 parts by weight) and hardener (35 parts by weight) were measured in to a glass beaker and mixed well (10 minutes minimum) using a wooden spatula. The thoroughly mixed epoxy was then degassed under high vacuum (oil pump) in a vacuum desiccator for 20–30 minutes. A clean 30 mL polypropylene syringe was filled with the degassed epoxy. The syringe was placed in the vacuum desiccator and the epoxy degassed under high vacuum for an additional 20–30 minutes. The syringe was then fitted with a blunt needle (DN-25; Glenmarc Manufacturing, Inc.; Mundelein, Ill., USA) and affixed to a PVT-2000-DT dispensing unit (Glenmarc Manufacturing, Inc.; Mundelein, Ill., USA). Epoxy was applied to the surface of each Spreeta 2000 using argon pressure (10 psi) for 2.7 seconds. The sensors were then placed in a plastic holder designed to maintain the gluing surface of the Spreeta 2000s in a horizontal position, and a gold-on-glass chip carefully applied to each using a tweezers, taking care to ensure that the chip was located completely within the alignment nubs. The assembled Spreeta 2000s were allowed to cure for 48 hours at room temperature in a dust-free environment. Finished sensors were stored at room temperature in the dark in a dust-free container.

Example 14

Preparation of Boronic Acid Conjugated Protein (Alkaline Phosphatase)

Alkaline phosphatase (Sigma; St Louis, Mo., USA) (0.21 g) was placed in a 50 mL polypropylene centrifuge tube and aqueous sodium bicarbonate (0.1 M, pH 8.3, 20 mL) was added. The mixture was gently vortexed until all of the protein had dissolved. The solution was then transferred to dialysis tubing, and dialyzed against aqueous sodium bicarbonate (0.1 M, pH 8.3, 2 L) overnight at 4° C. The next day, the solution was removed from the dialysis tubing and the concentration of protein was determined to be 6.0 mg/mL from the ultraviolet absorbance at 280 nm (El mg/mL=0.77) using an HP8453 UV-VIS spectrophotometer (Agilent; Palo Alto, Calif., USA). 11611 A fresh solution of Versalinx amine modifying reagent ["PDBA-X—NHS"; 6-(3,5-bis-[1,3,2]dioxaborinan-2-yl-benzoylamino)-hexanoic acid 2,5-di-oxo-pyrrolidin-1-yl ester] (Prolinx, Inc.; Bothell, Wash., USA) in anhydrous N,N-dimethylformamide (100 mM, mg/mL) was prepared. An aliquot of this solution (129 mL; 30-fold molar excess over protein) was added to an aliquot of the above protein solution (10 mL) in a 15 mL polypropylene centrifuge tube and vortexed to mix. The reaction was allowed to proceed for 1 hour at 4° C. The solution was then transferred to dialysis tubing, and dialyzed against aqueous sodium bicarbonate (0.1 M, pH 8.3, 2 L) overnight at 4° C. The dialysis buffer was then refreshed and dialysis continued for an additional 24 hours at 4° C. Finally, the purified phenylenediboronic acid-alkaline phosphatase conjugate ("PDBA-AP") was transferred to a 15 mL polypropylene centrifuge tube and stored at 4° C.

Figure 6:
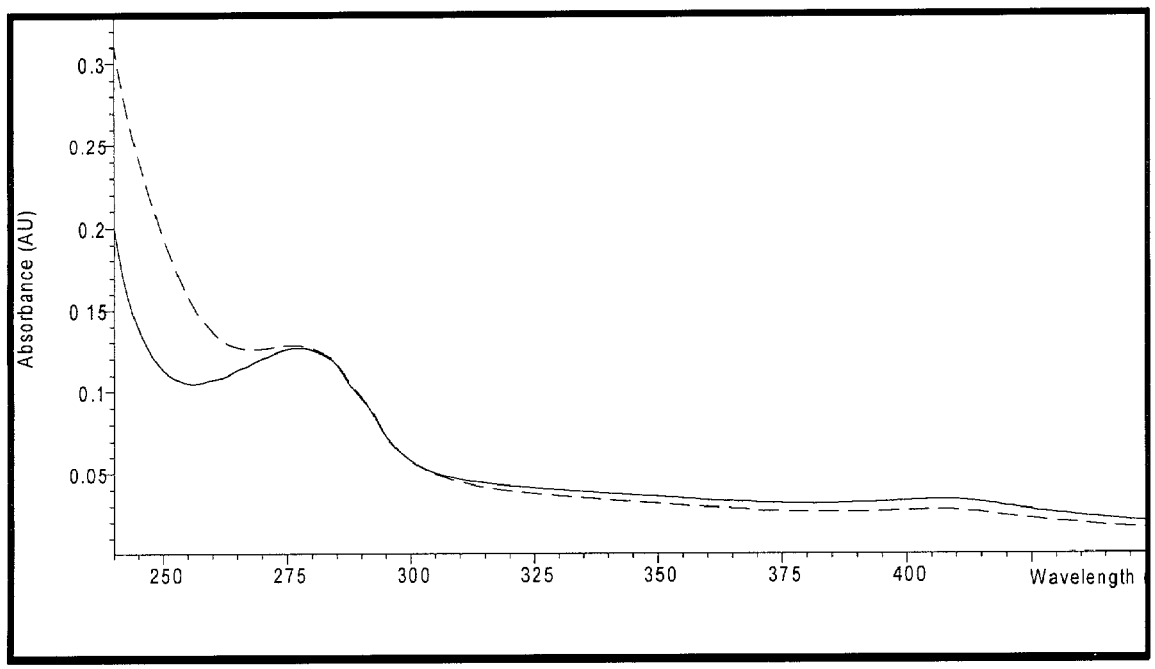
FIG. 6 presents ultraviolet spectra obtained for PDBA-conjugated alkaline phosphatase and unmodified alkaline phosphatase used to determine the extent of modification of PDBA-alkaline phosphatase, as described in Example 14.

The concentration of the PDBA-AP stock solution, as well as the degree of conjugation, were determined using ultraviolet absorbance. PDBA has negligible absorbance at 280 nm, but measurable absorbance at 260 nm. Hence, an aliquot of the PDBA-AP stock solution was used to determine the protein concentration using the ultraviolet absorbance at 280 nm ($\epsilon_{280}$=108,000 $M^{-1}$ $cm^{-1}$ for AP; $\epsilon_{280}$≈0 $M^{-1}$ $cm^{-1}$ for PDBA). Then, solutions of AP and PDBA-AP having equal protein concentrations were prepared by diluting the stock solutions. Ultraviolet spectra from 240 nm to 450 nm were obtained for each solution. These spectra are shown in FIG. 6 (solid trace, AP; dashed trace, PDBA-AP). The difference in absorbance at 260 nm between the PDBA-AP spectrum and the AP spectrum is due to absorbance from conjugated PDBA ($\epsilon_{260}$=4000 $M^{-1}$ $cm^{-1}$). This difference was used to calculate the concentration of PDBA in the PDBA-AP solution, yielding a molar conjugation ration of 8.1 PDBA moieties per protein molecule (on average).

Example 15

Immobilization of Boronic Acid Conjugated Protein (PDBA-AP) on Sensor Surface

A Spreeta 2000 sensor was assembled as described in Example 13, using a gold-on-glass chip with a mixed SAM immobilization matrix prepared as in Example 10. The matrix was prepared using a 1.0 mM solution of compound 14 (8 mole %) and compound 15 (92 mole %) in absolute ethanol. The sensor was then fitted with an aluminum flow cell equipped with a silicone gasket to provide a flow channel obtained from Texas Instruments. The inlet to the flow cell was attached to a six-port liquid chromatography switching valve (Model 9725; Rheodyne. L. P.; Rhonert Park, Calif., USA) which was, in turn, connected to a syringe pump (Model NE-1 000; New Era Pump Systems; Wantagh, N.Y., USA) fitted with a 10 mL glass syringe (Gas-tight; Hamilton, Co.; Reno, Nev., USA). All tubing used was made of PEEK including the sample loop (100 1L) on the switching valve. Samples was introduced into the flow stream by completely filling the sample loop and then switching the loop in line with the flow system. Care was taken not to introduce air bubbles into the flow stream during the sample loading and injection process. The sensor was connected to a custom digital signal processing interface attached to a personal computer. Software to acquire and display the raw sensor data over time was obtained from Texas Instruments (Spreeta software version 3.68).

The sensor was initiated in air prior to use according to instructions received from Texas Instruments. The syringe was then filled with buffer (phosphate-buffered saline [PBS]: 0.14 M sodium chloride, 8 mM disodium hydrogen phosphate, 2 mM sodium dihydrogen phosphate, pH 7.3) and the flow started at 6.0 mL/hour. Data were collected from the sensor using an LED intensity setting of 1 and an integration time of 1.62 msec. Surface plasmon resonance (SPR) curves were obtained from which a sensorgram (plot of refractive index versus time) was calculated and displayed automatically by the software. After obtaining a stable baseline measurement using buffer, an aliquot (100 µL) of PDBA-AP (prepared as in Example 14; 0.25 mg/mL in PBS) was loaded into the sample loop and injected into the flow stream. Data on the immobilization of PDBA-AP to the sensor matrix were then collected.

Figure 7:
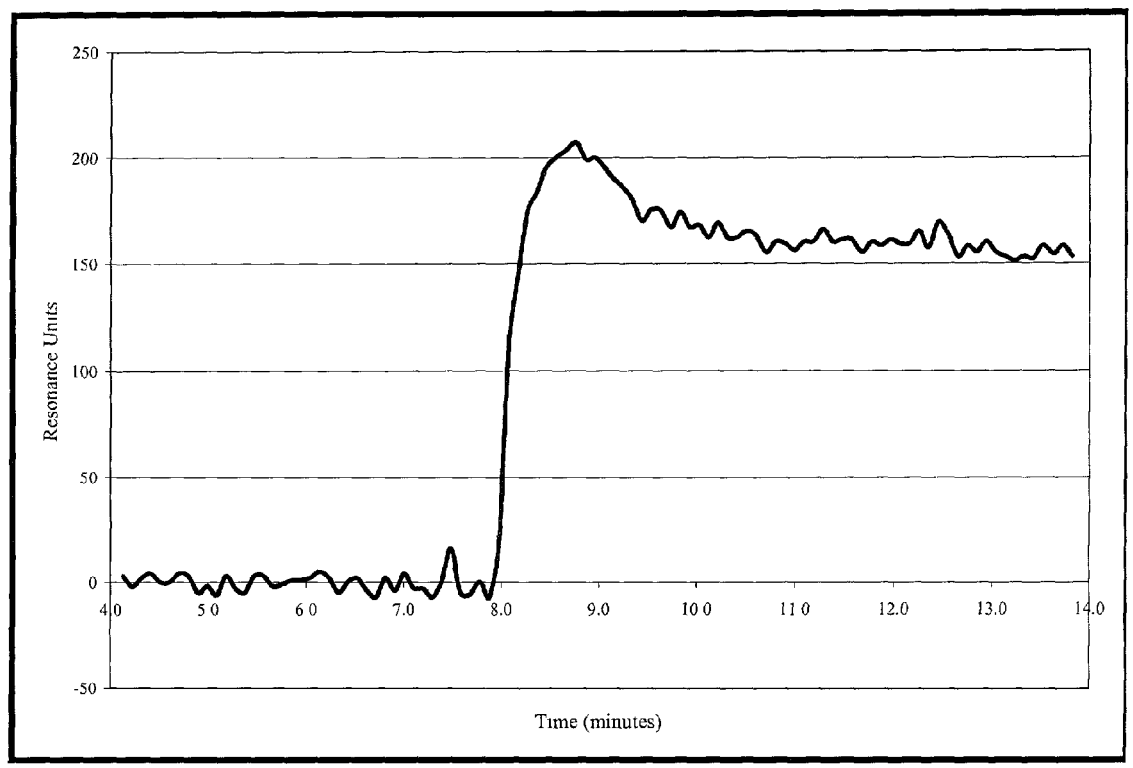
FIG. 7 presents the sensorgram data for the immobilization of PDBA-conjugated alkaline phosphatase on the surface of a Spreeta 2000 sensor according to the compositions and methods of the present invention, as described in Example 15.

FIG. 7 presents the sensorgram data obtained from this experiment. The buffer baseline prior to sample injection was mathematically adjusted to zero by subtracting an average of the raw signal over the time period 5.0 to 7.0 minutes from the entire data set. The y-axis of the plot is given in Resonance Units (RU), which are equivalent to the change in refractive index times $10^6$. Injection of the sample occurred just prior to 8 minutes, where the signal rises quickly in the data. This is due to the increased bulk refractive index of the solution containing protein as well as binding of the PDBA-conjugated protein to the surface matrix. After the 100 µL bolus of protein solution is cleared from the sensor flow cell, the sensor establishes a new buffer baseline position (at approximately 150 RU), due to immobilization of protein on the sensor surface.

Example 16

Demonstration of Low Protein Non-Specific Binding to Sensor Surface

Spreeta 2000 sensors were assembled as described in Example 13, using gold-on-glass chips with either a unitary SAM immobilization matrix prepared as in Example 9 or a mixed SAM immobilization matrix prepared as in Examples 10 and 11. The compositions of the various matrices and methods of preparation are given in Table II. Each sensor was then fitted with an aluminum flow cell equipped with a silicone gasket to provide a flow channel obtained from Texas Instruments. The inlet to the flow cell was attached to a six-port liquid chromatography switching valve (Model 9725; Rheodyne. L. P.; Rhonert Park, Calif., USA) which was, in turn, connected to a syringe pump (Model NE-1000; New Era Pump Systems; Wantagh, N.Y., USA) fitted with a 10 mL glass syringe (Gas-tight; Hamilton, Co.; Reno, Nev., USA). All tubing used was made of PEEK including the sample loop (100 µL) on the switching valve. Sample was introduced into the flow stream by completely filling the sample loop and then switching the loop in line with the flow system. Care was taken not to introduce air bubbles into the flow stream during the sample loading and injection process. Each sensor was connected to a custom digital signal processing interface attached to a personal computer. Software to acquire and display the raw sensor data over time was obtained from Texas Instruments (Spreeta software version 3.68).

Each sensor was initiated in air prior to use according to instructions received from Texas Instruments. The syringe was then filled with buffer (phosphate-buffered saline [PBS]: 0.14 M sodium chloride, 8 mM disodium hydrogen phosphate, 2 mM sodium dihydrogen phosphate, pH 7.3) and the flow started at 6.0 mL/hour. Data were collected from the sensor using an LED intensity setting of 1.0 and an integration time of 1.62 msec. Surface plasmon resonance (SPR) curves were obtained from which a sensorgram (plot of refractive index versus time) was calculated and displayed automatically by the software. After obtaining a stable baseline measurement using buffer, an aliquot (100 µL) of a solution containing four proteins—human fibrinogen, ovalbumin, carbonic anhydrase and lysozyme (each 0.25 mg/mL in PBS)—was injected into the flow stream. Data on the non-specific binding of these four unconjugated proteins to each sensor matrix were then collected.

Table II below presents representative data for the variety of sensor surface matrices. Bare gold is included for reference, since bare gold exhibits significant non-specific binding of proteins. The non-specific binding is calculated as the difference in refractive index (in RU) between the buffer baseline established prior to the injection of the protein solution and the buffer baseline established following injection of the protein solution.

TABLE II

| Sensor Surface Matrix | Non-Specific Binding (RU) | % NSB (relative to bare gold) |
| --- | --- | --- |
| Bare gold | 469 | 100 |
| 100 mole % Compound 6 | 32 | 6.8 |
| 100 mole % Compound 15 | 38 | 8.1 |

TABLE II-continued

| Sensor Surface Matrix | Non-Specific Binding (RU) | % NSB (relative to bare gold) |
|---|---|---|
| 2 mole % Compound 14 + 98 mole % Compound 15 (two-step procedure) | 19 | 4.1 |
| 4 mole % Compound 14 + 96 mole % Compound 15 (one-step procedure) | 64 | 13.6 |
| 4 mole % Compound 14 + 96 mole % Compound 15 (two-step procedure) | 16 | 3.4 |
| 8 mole % Compound 14 + 92 mole % Compound 15 (one-step procedure) | 31 | 6.6 |
| 4 mole % Compound 14 + 96 mole % Compound 15 (one-step procedure) | 26 | 5.5 |
| 20 mole % Compound 14 + 80 mole % Compound 15 (one-step procedure) | 100 | 21.3 |

The data clearly indicate that the unitary and mixed SAMs confer significant protection against non-specific protein binding to the sensor surface.

Example 17

Demonstration of Sequential Immobilization of Increasing Amounts of Protein on Sensor Surface Two Spreeta 2000 sensors were assembled as described in Example 13, using gold-on-glass chips with a mixed SAM immobilization matrix prepared as in Example 10. The matrix was prepared using a 1.0 mM solution of compound 14 (4 mole %) and compound 15 (96 mole %) in absolute ethanol. Each sensor was then fitted with an aluminum flow cell equipped with a silicone gasket to provide a flow channel obtained from Texas Instruments. The inlet to the flow cell was attached to a six-port liquid chromatography switching valve (Model 9725; Rheodyne. L. P.; Rhonert Park, Calif., USA) which was, in turn, connected to a syringe pump (Model NE-1000; New Era Pump Systems; Wantagh, N.Y., USA) fitted with a 10 mL glass syringe (Gas-tight; Hamilton, Co.; Reno, Nev., USA). All tubing used was made of PEEK including the sample loop (100 µL) on the switching valve. Sample was introduced into the flow stream by completely filling the sample loop and then switching the loop in line with the flow system. Care was taken not to introduce air bubbles into the flow stream during the sample loading and injection process. Each sensor was connected to a custom digital signal processing interface attached to a personal computer. Software to acquire and display the raw sensor data over time was obtained from Texas Instruments (Spreeta software version 3.68).

Each sensor was initiated in air prior to use according to instructions received from Texas Instruments. The syringe was then filled with buffer (phosphate-buffered saline [PBS]: 0.14 M sodium chloride, 8 mM disodium hydrogen phosphate, 2 mM sodium dihydrogen phosphate, pH 7.3) and the flow started at 6.0 mL/hour. Data were collected from the sensor using an LED intensity setting of 1.0 and an integration time of 1.62 msec. Surface plasmon resonance (SPR) curves were obtained from which a sensorgram (plot of refractive index versus time) was calculated and displayed automatically by the software. After obtaining a stable baseline measurement using buffer, an aliquot (100 µL) of a solution containing either AP (0.050 mg/mL in PBS) or PDBA-AP (prepared as in Example 14; 0.050 mg/mL in PBS) was injected into the flow stream. Data on the binding of the protein to the sensor matrix were then collected until the buffer baseline had re-stabilized. Then, a fresh aliquot (100 µL) of a solution containing either AP (0.100 mg/mL in PBS) or PDBA-AP (0.100 mg/mL in PBS) was injected into the flow stream, and data were again collected until the baseline had re-stabilized. This procedure was repeated twice more with aliquots of AP (0.200 and 0.400 mg/mL in PBS) or PDBA-AP (0.200 and 0.400 mg/mL in PBS).

Figure 8:
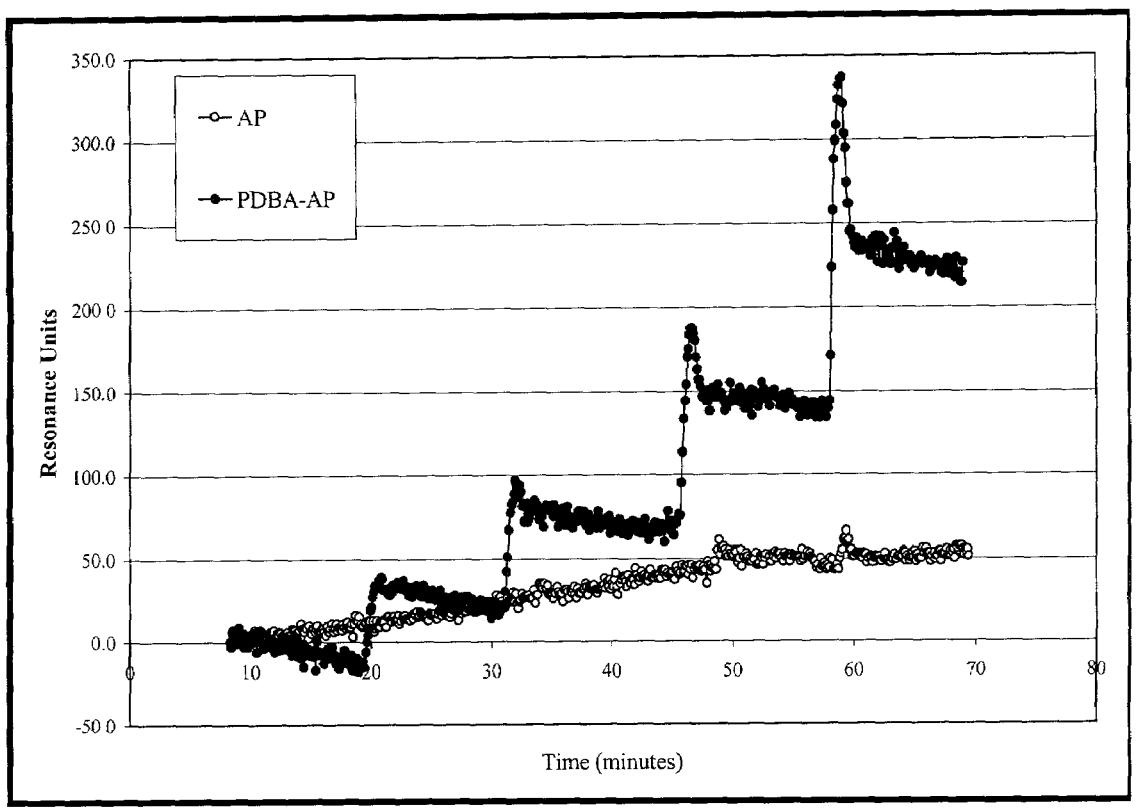
FIG. 8 presents the sensorgram data for the sequential immobilization of increasing amounts of PDBA-conjugated alkaline phosphatase on the surface of a Spreeta 2000 sensor according to the compositions and methods of the present invention, as described in Example 17.

FIG. 8 presents the sensorgram data from this experiment. The buffer baseline prior to the initial sample injection on each sensor was mathematically adjusted to zero by subtracting an average of the raw signal over the time period 8.0 to 10.0 minutes from the entire data set. The y-axis of the plot is given in Resonance Units (RU), which are equivalent to the change in refractive index times $10^6$. The open circles represent data obtained from the binding (non-specific) of AP to the sensor surface matrix. Even at very high protein loads (0.4 mg/mL), non-specific binding is small ($\leq 50$ RU). The closed circles represent data obtained from the immobilization (specific binding) of PDBA-AP to the sensor surface matrix. A titration is observed, as increasing amounts of protein are added to the surface. The spikes around 32, 47 and 60 minutes are due to the increased bulk refractive index of the solution containing protein. After each 100 µL bolus of protein solution is cleared from the sensor flow cell, the sensor establishes a new buffer baseline position (at approximately 40, 75, 150 and 225 RU), due to immobilization of increasing amounts protein on the sensor surface.

The data clearly indicate that the amount of protein that may be immobilized on the sensor surface matrix of the present invention can be varied by simply adding more PDBA-conjugated protein, up to the limit of the binding capacity of the matrix.

Example 18

Demonstration of Regeneration of Sensor Surface

A Spreeta 2000 sensor was assembled as described in Example 13, using a gold-on-glass chip with a mixed SAM immobilization matrix prepared as in Example 10. The matrix was prepared using a 1.0 mM solution of compound 14 (4 mole %) and compound 15 (96 mole %) in 10:90 (v/v) water:N,N-dimethylformamide. The sensor was then fitted with an aluminum flow cell equipped with a silicone gasket to provide a flow channel obtained from Texas Instruments. The inlet to the flow cell was attached to a six-port liquid chromatography switching valve (Model 9725; Rheodyne. L. P.; Rhonert Park, Calif., USA) which was, in turn, connected to a syringe pump (Model NE-1 000; New Era Pump Systems; Wantagh, N.Y., USA) fitted with a 10 mL glass syringe (Gas-tight; Hamilton, Co.; Reno, Nev., USA). All tubing used was made of PEEK including the sample loop (100 μL) on the switching valve. Samples was introduced into the flow stream by completely filling the sample loop and then switching the loop in line with the flow system. Care was taken not to introduce air bubbles into the flow stream during the sample loading and injection process. The sensor was connected to a custom digital signal processing interface attached to a personal computer. Software to acquire and display the raw sensor data over time was obtained from Texas Instruments (Spreeta software version 3.68).

The sensor was initiated in air prior to use according to instructions received from Texas Instruments. The syringe was then filled with buffer (phosphate-buffered saline [PBS]: 0.14 M sodium chloride, 8 mM disodium hydrogen phosphate, 2 mM sodium dihydrogen phosphate, pH 7.3) and the flow started at 6.0 mL/hour. Data were collected from the sensor using an LED intensity setting of 1 and an integration time of 1.62 msec. Surface plasmon resonance (SPR) curves were obtained from which a sensorgram (plot of refractive index versus time) was calculated and displayed automatically by the software. After obtaining a stable baseline measurement using buffer, an aliquot (100 μL) of PDBA-AP (prepared as in Example 14; final conjugation ratio 3.2:1 PDBA:AP; 0.05 mg/mL in PBS) was loaded into the sample loop and injected into the flow stream. Data on the immobilization of PDBA-AP to the sensor matrix were then collected. After the buffer baseline had been re-established, an aliquot of aqueous sodium hydroxide (1 N; 100 μL) was loaded into the sample loop and injected into the flow stream. After the buffer baseline had been re-established, the process was repeated once more.

Figure 9:
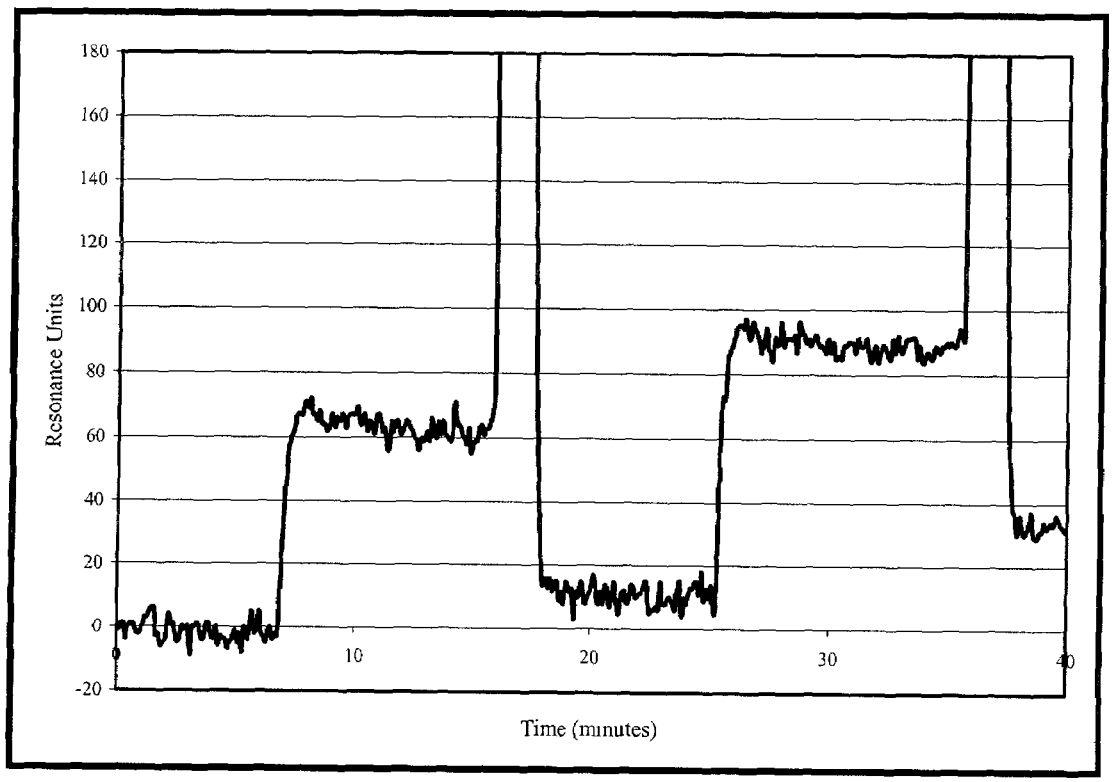
FIG. 9 presents the sensorgram data for the sequential immobilization and release of PDBA-conjugated alkaline phosphatase on the surface of a Spreeta 2000 sensor according to the compositions and methods of the present invention, as described in Example 18.

FIG. 9 presents the sensorgram data obtained from this experiment. The buffer baseline prior to sample injection was mathematically adjusted to zero by subtracting an average of the raw signal over the time period 2.0 to 5.0 minutes from the entire data set. The y-axis of the plot is given in Resonance Units (RU), which are equivalent to the change in refractive index times $10^6$. Injection of the sample occurred just prior to 7 minutes, where the signal rises quickly in the data. This is due to the increased bulk refractive index of the solution containing protein as well as binding of the PDBA-conjugated protein to the surface matrix. After the 100 μL bolus of protein solution is cleared from the sensor flow cell, the sensor establishes a new buffer baseline position (at approximately 65 RU), due to immobilization of protein on the sensor surface. Injection of aqueous sodium hydroxide (1 N) serves to break the bonds holding the boronic acid complex together, removing the immobilized protein from the sensor surface. This happens essentially quantitatively, as following buffer re-equilibration of the sensor surface matrix (time points 18 to 25 minutes), an equivalent amount of PDBA-AP can again be immobilized (time points 25 to 35 minutes; approximately 80 RU).

The data clearly indicate that immobilization of ligand on a sensor surface by means of the present invention can be reversed to regenerate native sensor surface matrix. This regenerated matrix can then be used again to immobilize a fresh aliquot of ligand in an essentially quantitative manner.

Example 19

Typical Sensing Application—Specific Antibody Binding to its Antigen Immobilized on Sensor Surface A Spreeta 2000 sensor was assembled as described in Example 13, using a gold-on-glass chip with a mixed SAM immobilization matrix prepared as in Example 10. The matrix was prepared using a 1.0 mM solution of compound 14 (8 mole %) and compound 15 (92 mole %) in absolute ethanol. The sensor was then fitted with an aluminum flow cell equipped with a silicone gasket to provide a flow channel obtained from Texas Instruments. The inlet to the flow cell was attached to a six-port liquid chromatography switching valve (Model 9725; Rheodyne. L. P.; Rhonert Park, Calif., USA) which was, in turn, connected to a syringe pump (Model NE-1000; New Era Pump Systems; Wantagh, N.Y., USA) fitted with a 10 mL glass syringe (Gas-tight; Hamilton, Co.; Reno, Nev., USA). All tubing used was made of PEEK including the sample loop (100 μL) on the switching valve. Sample was introduced into the flow stream by completely filling the sample loop and then switching the loop in line with the flow system. Care was taken not to introduce air bubbles into the flow stream during the sample loading and injection process. The sensor was connected to a custom digital signal processing interface attached to a personal computer. Software to acquire and display the raw sensor data over time was obtained from Texas Instruments (Spreeta software version 3.68).

The sensor was initiated in air prior to use according to instructions received from Texas Instruments. The syringe was then filled with buffer phosphate-buffered saline [PBS]: 0.14 M sodium chloride, 8 mM disodium hydrogen phosphate, 2 mM sodium dihydrogen phosphate, pH 7.3) and the flow started at 6.0 mL/hour. Data were collected from the sensor using an LED intensity setting of 1.0 and an integration time of 1.62 msec. Surface plasmon resonance (SPR) curves were obtained from which a sensorgram (plot of refractive index versus time) was calculated and displayed automatically by the software. After obtaining a stable baseline measurement using buffer, an aliquot (100 1L) of PDBA-AP (prepared as in Example 14; 0.25 mg/mL in PBS) was loaded into the sample loop and injected into the flow stream. The PDBA-AP was immobilized to the surface matrix as described in Example 15. Approximately 140 RU of PDBA-AP was immobilized. Data collection was started, and the sensor was washed with PBS buffer until a stable baseline was re-established. Then, an aliquot (100 μL) of a polyclonal antibody against AP (anti-AP; Rockland, Inc.; Gilbertsville, Pa., USA; 3.0 1M in PBS) was injected into the flow stream. The sensor was washed with PBS buffer until a stable baseline was re-established. Then, an aliquot (100 μL) of aqueous sodium hydroxide (0.1 N) was injected to dissociate the bound antibody from the AP, and the sensor was washed with PBS buffer until a stable baseline was re-established. This procedure (injection of antibody solution, washing, dissociation with sodium hydroxide and washing) was repeated once more.

Figure 10:
FIG. 10 presents the sensorgram data for the binding of an antibody to alkaline phosphatase to immobilized PDBA-conjugated alkaline phosphatase on the surface of a Spreeta 2000 sensor, as described in Example 19.

FIG. 10 presents the sensorgram data from this experiment. The buffer baseline prior to antibody injection was mathematically adjusted to zero by subtracting an average of the raw signal over the time period 5.0 to 7.0 minutes from the entire data set. The y-axis of the plot is given in Resonance Units (RU), which are equivalent to the change in refractive index times $10^6$. Injection of the first antibody aliquot occurred at about 4.5 minutes, where the signal rises quickly in the data. After the 100 μL bolus of antibody solution is cleared from the sensor flow cell, the sensor establishes a new buffer baseline position (at approximately 110 RU), due to binding of the analyte (antibody) to the immobilized ligand (AP) on the sensor surface. Since the molecular masses of the two proteins, PDBA-AP (about 140,000 daltons) and anti-AP (about 150,000 daltons) are similar, the response due to antibody binding (110 RU) is expected to be similar to the initial amount of PDBA-AP immobilized (140 RU), assuming a 1:1 interaction between the two proteins. The fact that the antibody binding response is slightly less than anticipated may mean either that some fraction of antibody species is binding simultaneously to two PDBA-AP molecules (each antibody has two potential binding sites), or that some fraction of the PDBA-AP is immobilized in such a way that the antibody recognition site (epitope) is not available for antibody binding.

The first injection of sodium hydroxide occurred at about 10 minutes, as indicated by the rapid drop in refractive index to a point below zero (this is due to the lower refractive index of the sodium hydroxide solution relative to the PBS buffer). Following washing with PBS buffer, the baseline re-stabilized at about 5–10 RU, indicating that the antibody had been nearly completely stripped from the immobilized PDBA-AP. Repetition of the cycle yielded the same result within experimental accuracy.

The data clearly indicate that immobilization of ligand on a sensor surface by means of the present invention provides an active ligand capable of binding analyte with good efficiency. Additionally, the immobilization of ligand on a sensor surface by means of the present invention is sufficiently stable to allow multiple ligand regeneration and analyte binding cycles.

Example 20

Typical Sensing Application—Specific Binding of IgG to Protein A Immobilized on Sensor Surface A Spreeta 2000 sensor was assembled as described in Example 13, using a gold-on-glass chip with a mixed SAM immobilization matrix prepared as in Example 11. The matrix was prepared using a 1.0 mM solution of compound 14 (4 mole %) and compound 15 (96 mole %) in 10:90 (v/v) water:N,N-dimethylformamide. The sensor was then fitted with an aluminum flow cell equipped with a silicone gasket to provide a flow channel obtained from Texas Instruments. The inlet to the flow cell was attached to a six-port liquid chromatography switching valve (Model 9725; Rheodyne. L. P.; Rhonert Park, Calif., USA) which was, in turn, connected to a syringe pump (Model NE-1000; New Era Pump Systems; Wantagh, N.Y., USA) fitted with a 10 mL glass syringe (Gas-tight; Hamilton, Co.; Reno, Nev., USA). All tubing used was made of PEEK including the sample loop (100 μL) on the switching valve. Sample was introduced into the flow stream by completely filling the sample loop and then switching the loop in line with the flow system. Care was taken not to introduce air bubbles into the flow stream during the sample loading and injection process. The sensor was connected to a custom digital signal processing interface attached to a personal computer. Software to acquire and display the raw sensor data over time was obtained from Texas Instruments (Spreeta software version 3.68).

The sensor was initiated in air prior to use according to instructions received from Texas Instruments. The syringe was then filled with buffer (phosphate-buffered saline plus surfactant [PBSS]: 0.14 M sodium chloride, 8 mM disodium hydrogen phosphate, 2 mM sodium dihydrogen phosphate, pH 7.3 plus 0.1% [v/v] lauryl dimethylpropyl betaine) and the flow started at 6.0 mL/hour. Data were collected from the sensor using an LED intensity setting of 1.0 and an integration time of 1.62 msec. Surface plasmon resonance (SPR) curves were obtained from which a sensorgram (plot of refractive index versus time) was calculated and displayed automatically by the software. After obtaining a stable baseline measurement using buffer, an aliquot (100 μL) of PDBA-Protein A (Protein A from Prozyme, San Leandro, Calif., USA; prepared as in Example 14, using a 15:1 molar input ratio of PDBA-X-NHS to Protein A, final conjugation ratio 4:1 PDBA:Protein A; 1.0 mg/mL in PBSS) was loaded into the sample loop and injected into the flow stream. The PDBA-Protein A was immobilized to the surface matrix as described in Example 15. Approximately 38 RU of PDBA-Protein A was immobilized. Data collection was started, and the sensor was washed with PBSS buffer until a stable baseline was re-established. Then, an aliquot (100 μL) of a polyclonal IgG (Jackson Immunoresearch, West Grove, Pa., USA; 0.05 mg/mL in PBSS) was injected into the flow stream. The sensor was then washed with PBSS buffer until a stable baseline was re-established.

Figure 11:
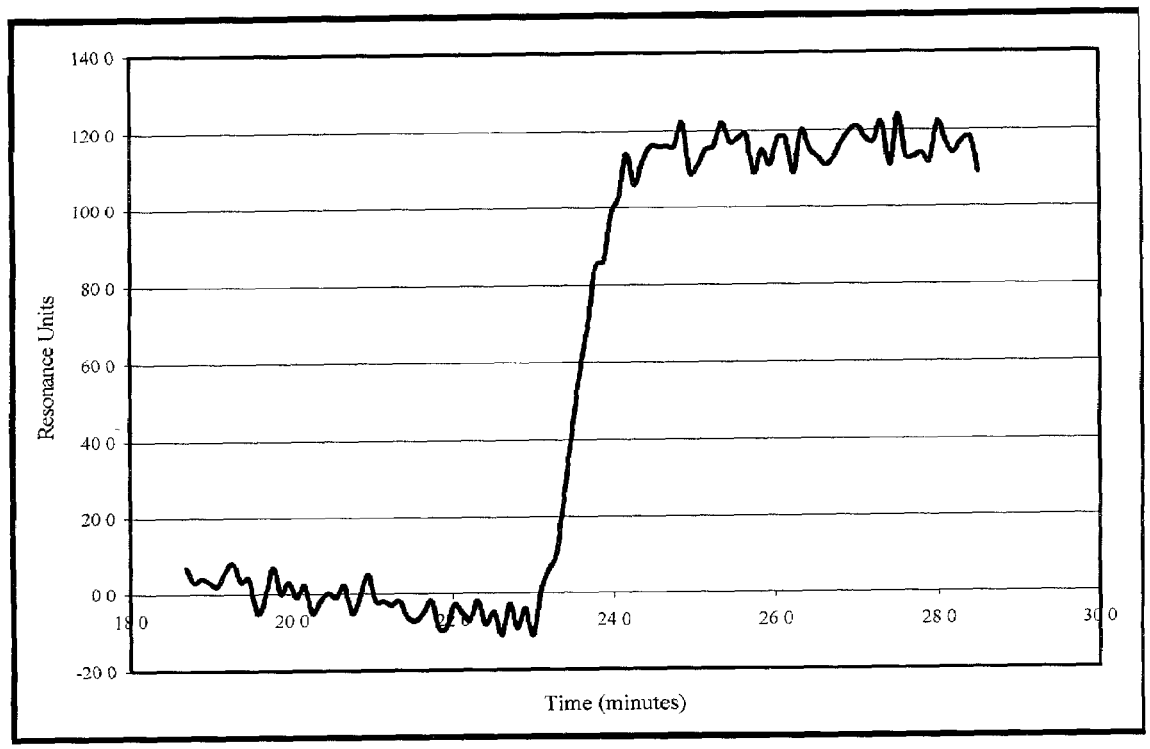
FIG. 11 presents the sensorgram data for the binding of a human IgG to immobilized PDBA-conjugated Protein A on the surface of a Spreeta 2000 sensor, as described in Example 20.

FIG. 11 presents the sensorgram data from this experiment. The buffer baseline prior to antibody injection was mathematically adjusted to zero by subtracting an average of the raw signal over the time period 20.0 to 22.0 minutes from the entire data set. The y-axis of the plot is given in Resonance Units (RU), which are equivalent to the change in refractive index times $10^6$. Injection of the antibody aliquot occurred at about 23.0 minutes, where the signal rises quickly in the data. After the 100 μL bolus of antibody solution is cleared from the sensor flow cell, the sensor establishes a new buffer baseline position (at approximately 115 RU), due to binding of the analyte (IgG) to the immobilized ligand (Protein A) on the sensor surface.

The data clearly indicate that immobilization of ligand on a sensor surface by means of the present invention provides an active ligand capable of binding analyte with good efficiency.

It should be noted that, although the above examples describe specific implementations and manipulations of the sensor surface matrix of the present invention, those skilled in the art will readily understand that many alternative implementations and manipulations may be had. For example, instrumentation for the detection of molecular interactions using surface plasmon resonance other than the Spreeta 2000 could be fitted with surfaces comprising a matrix of the present invention. Additionally, other modes of detection (e.g., fluorescence) could be used. Also, regeneration of the matrix as demonstrated in Example 18 can be accomplished not only at high pH (with aqueous base), but also at low pH (with aqueous acid), at elevated temperature (50–60° C.), and by the use of competitive binding agents.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A sensor surface for detecting the interaction of a biological binding pair, said sensor surface comprising:
   a substrate coated with a free electron metal;
   a matrix layer disposed on said free electron metal, said matrix layer comprising an organic compound, wherein said organic compound has a boronic acid complexing moiety;
   a boronic acid moiety complexed to said boronic acid complexing moiety; and
   a first member of said binding pair conjugated to said boronic acid moiety, wherein said first member binds to a second member of said binding pair such that a detectable response is elicited.

2. The sensor surface of claim 1, wherein said matrix is a self-assembled monolayer, a mixed self-assembled monolayer, or combinations thereof.

3. The sensor surface of claim 2, wherein said matrix is a mixed self-assembled monolayer.

4. The sensor surface of claim 2, wherein said free electron metal is a member selected from the group consisting of copper, silver, aluminum, platinum and gold.

5. The sensor surface of claim 4, wherein said free electron metal is gold.

6. The sensor surface of claim 1, wherein said organic compound having said boronic acid complexing moiety is of the formula:

X—R—Y     (I)

wherein:
   X is an anchor group that forms a complex with said free-electron metal;
   R is an optionally substituted alkylene group optionally interrupted by one or more members selected from the group consisting of a heteroatom, an amido group and combinations thereof; and
   Y is a boronic acid complexing moiety.

7. The sensor surface of claim 6, wherein said organic compound having said boronic acid complexing moiety is of the formula:

X(CH$_2$)$_n$C(O)NHR'-(NSBI)$_m$-Y     (IIa)

X(CH$_2$)$_n$NHC(O)R'-(NSBI)$_m$-Y     (IIb)

wherein:
   n is an integer from about 1 to 5;
   R' is an optionally substituted alkylene group optionally interrupted by a heteroatom;
   NSBI is a nonspecific binding inhibitor;
   m is 0 or 1; and
   Y is a boronic acid complexing moiety.

8. The sensor surface of claim 7, wherein R' is an optionally substituted alkylene group, which is optionally interrupted by a heteroatom and which is at least about 8 carbon atoms in length.

9. The sensor surface of claim 7, wherein said nonspecific binding inhibitor is a member selected from the group consisting of an oligo(ethylene glycol), a poly(ethylene glycol), a branched OEG, a branched PEG, an oligo(peptide), an oligo(propylene sulfoxide), a sugar, a sugar alcohol, and a dendrimer.

10. The sensor surface of claim 7, wherein R is an optionally substituted alkylene group, which is optionally interrupted by a heteroatom and which is between about 8 carbon atoms to about 40 carbon atoms in length.

11. The sensor surface of claim 7, wherein m is 1.

12. The sensor surface of claim 7, wherein Y has the formula:

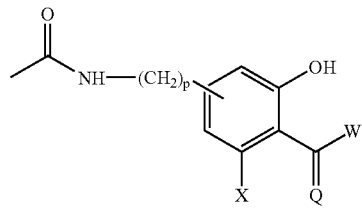

wherein:
   W is a member selected from the group consisting of H, OH, NH$_2$, NHCH$_3$, NHOH and NHOCH$_3$;
   Q is a member selected from the group consisting of O, S and NH;
   X is a member selected from the group consisting of H or OH; and
   p is 0 to 3.

13. The sensor surface of claim 12, wherein said organic compound having said boronic acid complexing moiety is of the formula HS(CH$_2$)$_n$C(O)NHR'-(NSBI)-SHA     (IV)

wherein:
   n is an integer from 1 to about 5;
   R' is an optionally substituted alkylene group, which is optionally interrupted by a heteroatom;
   NSBI is a nonspecific binding inhibitor;
   x is 0 or 1; and
   SHA is a salicyihydroxamic acid.

14. The sensor surface of claim 13, wherein R' is an optionally substituted alkylene group, which is optionally interrupted by a heteroatom and which is at least about 8 carbon atoms in length.

15. The sensor surface of claim 13, wherein said nonspecific binding inhibitor is a member selected from the group consisting of an oligo(ethylene glycol), a poly(ethylene glycol), a branched OEG, a branched PEG, an oligo(peptide), an oligo(propylene sulfoxide), a sugar, a sugar alcohol, and a dendrimer.

16. The sensor surface of claim 13, wherein R' is an optionally substituted alkylene group, which is optionally interrupted by a heteroatom and which is between about 8 carbon atoms to about 40 carbon atoms in length.

17. The sensor surface of claim 12, wherein said organic compound having said boronic acid complexing moiety is of the formula:

HS(CH$_2$)$_2$C(O)NHR'-(NSBI)-DHBHA     (V)

wherein:
   n is an integer from 1 to about 5;
   R' is an optionally substituted alkylene group, which is optionally interrupted by a heteroatom;
   NSBI is a nonspecific binding inhibitor; and
   DHBHA is a dihydroxybenzohydroxamic acid.

18. The sensor surface of claim 3, wherein said matrix comprises an organic compound of the formula:

X—(CH$_2$)$_n$C(O)NHR'-(NSBI)$_m$-Z     (VIa)

or

X—(CH$_2$)$_n$C(O)NHR'-(NSBI)$_m$-Z     (VIb)

wherein:
X is an anchor group that forms a complex with a free electron metal;
n is an integer from 1 to 5;
R' is an optionally substituted alkylene group, which is optionally interrupted by a heteroatom;
NSB is a nonspecific binding inhibitor;
m is 0 or 1; and
Z is an unreactive, uncharged chain-terminating group.

19. The sensor surface of claim 18, wherein said nonspecific binding inhibitor is a member selected from the group consisting of an oligo(ethylene glycol), a poly(ethylene glycol), a branched OEG, a branched PEG, an oligo(peptide), an oligo(propylene sulfoxide), a sugar, a sugar alcohol, and a dendrimer.

20. The sensor surface of claim 18, wherein Z is a member selected from the group consisting of H, $CH_3$, OH, $OCH_3$, $CO_2CH_3$, $C(O)NH_2$, $C(O)NHCH_3$, $C(O)N(CH_3)_2$ or $SO_2NH_2$.

21. The sensor surface of claim 18, wherein said matrix layer comprises a combination of polymers having the formula:
$SCH_2C(O)NH(CH_2)_{11}(OCH_2CH_2)_{11}OC(O)Y$ (Polymer A), wherein Y is a boronic acid complexing moiety; and $—SCH_2C(O)NH—(CH_2)_{11}(COCH_2CH_2)_3OH$ (Polymer B).

22. The sensor surface of claim 21, wherein the mole percent of Polymer A is less than about 10% of the total mole percent of Polymer A and Polymer B.

23. The sensor surface of claim 21, wherein the mole percent of the Polymer A is less than about 5% of the total mole percent of Polymer A and Polymer B.

24. The sensor surface of claim 18, wherein R' is an optionally substituted alkylene group, which is optionally interrupted by a heteroatom and which is at least about 8 carbon atoms in length.

25. The sensor surface of claim 18, wherein R' is an optionally substituted alkylene group, which is optionally interrupted by a heteroatom and which is between about 8 carbon atoms to about 40 carbon atoms in length.

26. The sensor surface of claim 1, wherein said boronic acid moiety comprises a bioactive species.

27. The sensor surface of claim 26, wherein said boronic acid moiety is of the formula:

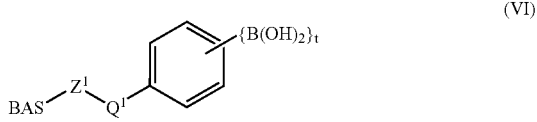

(VI)

wherein:
BAS is a bioactive species, selected from the group consisting of a protein, a polypeptide, a polypeptide fragment, a nucleic acid, a carbohydrate, a receptor, a hormone, a toxin, a vesicle, a liposome and a cell;
$Z^1$ is a member selected from the group consisting of a saturated or unsaturated aliphatic chain up to about 0 to 6 carbon equivalents in length, an unbranched saturated or unsaturated aliphatic chain of from about 6 to 18 carbon equivalents in length with at least one intermediate amide or disulfide moiety, and a polyethylene glycol chain of from about 3 to 12 carbon equivalents in length;
$Q^1$ is a member selected from the group consisting of an amide, methyl amide, methylene, ether, thioether, methylene ether and methylene thioether moieties; and
t is an integer from 1 to 3.

28. The sensor surface of claim 27 wherein said protein is selected from the group consisting of a capture protein, an antigen, an antibody, protein A, protein G, protein A/G, an enzyme, a lectin, and avidin.

29. The sensor surface of claim 27, wherein said boronic acid moiety has the formula:

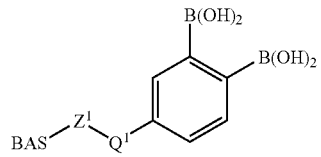

wherein:
BAS is a protein;
$Z^1$ is $C_1$–$C_4$ alkylene; and
$Q^1$ is an amide.

30. The sensor surface of claim 27, wherein said boronic acid moiety has the formula:

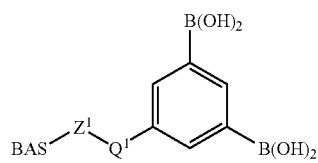

wherein:
BAS is a protein;
$Z^1$ is $C_1$–$C_4$ alkylene; and
$Q^1$ is an amide.

31. The sensor surface of claim 27, wherein said boronic acid moiety has the formula:

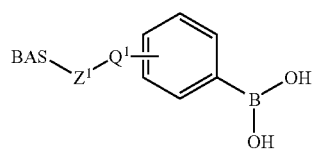

wherein:
BAS is a protein;
$Z^1$ is $C_1$–$C_4$ alkylene; and
$Q^1$ is an amide.

32. The sensor surface of claim 1, wherein said sensor surface is an array of sensor surfaces.

33. The sensor surface of claim 1, wherein said sensor surface is part of a surface plasmon resonance sensing apparatus or a potentiometric sensing apparatus.

34. A sensor surface, said sensor surface comprising:
a substrate coated with a free electron metal;
a matrix layer disposed on said free electron metal, said matrix layer comprising an organic compound, wherein said organic compound has the formula

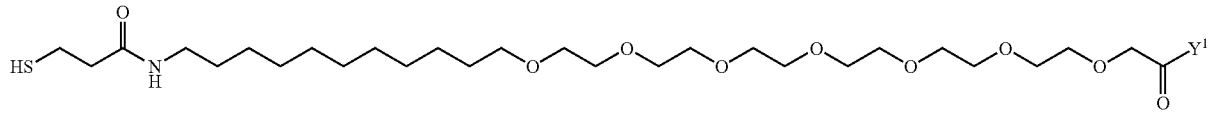

wherein:
  $Y^1$ is a member selected from the group consisting of a boronic acid complexing moiety, a binding partner, a cell, a receptor, a liposome, a vesicle, an artificial membrane, a protein, a polypeptide, a protein fragment, a polypeptide fragment, a peptide hormone, a nucleic acid, a toxin, a hapten, a hormone, a sugar, biotin, a vitamin, and combinations thereof.

35. A process for immobilizing a ligand on a sensor surface, said process comprising:
  admixing a boronic acid reagent having a reactive group with a ligand to form a boronic acid-ligand conjugate; and
  incubating said boronic acid-ligand conjugate with said sensor surface wherein said sensor surface comprises:
    a substrate coated with a free electron metal;
    a matrix layer disposed on said free electron metal, said matrix layer comprising an organic compound, wherein said organic compound has a boronic acid complexing moiety complexed to the boronic acid-ligand conjugate, thereby immobilizing said ligand.

36. The process for immobilizing a ligand of claim 35, further comprising washing said boronic acid-ligand conjugate complexed to said boronic acid complexing moiety.

37. The process for immobilizing a ligand of claim 35, wherein said sensor surface comprises an array of sensor surfaces.

* * * * *